US009545528B2

(12) United States Patent
Gall et al.

(10) Patent No.: US 9,545,528 B2
(45) Date of Patent: Jan. 17, 2017

(54) CONTROLLING PARTICLE THERAPY

(71) Applicant: Mevion Medical Systems, Inc., Littleton, MA (US)

(72) Inventors: Kenneth P. Gall, Harvard, MA (US); Stanley Rosenthal, Wayland, MA (US); Thomas C. Sobczynski, Arlington, MA (US); Adam C. Molzahn, Leominster, MA (US); Charles D. O'Neal, III, Bolton, MA (US); James Cooley, Andover, MA (US)

(73) Assignee: Mevion Medical Systems, Inc., Littleton, MA (US)

( * ) Notice: Subject to any disclaimer, the term of this patent is extended or adjusted under 35 U.S.C. 154(b) by 56 days.

(21) Appl. No.: 14/038,888

(22) Filed: Sep. 27, 2013

(65) Prior Publication Data
US 2014/0094643 A1 Apr. 3, 2014

Related U.S. Application Data

(60) Provisional application No. 61/707,624, filed on Sep. 28, 2012.

(51) Int. Cl.
*H05H 15/00* (2006.01)
*A61N 5/10* (2006.01)
(Continued)

(52) U.S. Cl.
CPC ........... *A61N 5/1081* (2013.01); *A61N 5/1049* (2013.01); *A61N 5/1071* (2013.01); *A61N 5/1077* (2013.01);
(Continued)

(58) Field of Classification Search
None
See application file for complete search history.

(56) References Cited

U.S. PATENT DOCUMENTS

| 498,915 A | 6/1893 | Heimann |
|---|---|---|
| 2,280,606 A | 4/1942 | Van et al. |

(Continued)

FOREIGN PATENT DOCUMENTS

| CA | 2629333 | 5/2007 |
|---|---|---|
| CN | 1377521 | 10/2002 |

(Continued)

OTHER PUBLICATIONS

US 8,581,524, 11/2013, O'Neal et al. (withdrawn)
(Continued)

*Primary Examiner* — Douglas W Owens
*Assistant Examiner* — Srinivas Sathiraju
(74) *Attorney, Agent, or Firm* — Choate, Hall & Stewart LLP

(57) ABSTRACT

An example particle therapy system includes the following: a gantry that is rotatable relative to a patient position; a particle accelerator mounted to the gantry, where the particle accelerator is for outputting a particle beam essentially directly to the patient position; and a control system to receive a prescription and to generate machine instructions for configuring one or more operational characteristics of the particle therapy system. At least one of the operational characteristics relates to a rotational angle of the gantry relative to the patient position.

24 Claims, 34 Drawing Sheets

(51) Int. Cl.
  *H05H 7/12* (2006.01)
  *H05H 13/02* (2006.01)
  *H05H 7/00* (2006.01)
(52) U.S. Cl.
  CPC .............. *H05H 7/12* (2013.01); *H05H 13/02* (2013.01); *A61N 2005/1095* (2013.01); *H05H 2007/004* (2013.01)

(56) References Cited

U.S. PATENT DOCUMENTS

| | | |
|---|---|---|
| 2,492,324 A | 12/1949 | Salisbury |
| 2,615,129 A | 10/1952 | McMillan |
| 2,616,042 A | 10/1952 | Weeks |
| 2,626,351 A | 1/1953 | Powell |
| 2,659,000 A | 11/1953 | Salisbury |
| 2,701,304 A | 2/1955 | Dickinson |
| 2,789,222 A | 4/1957 | Martin |
| 2,812,463 A | 11/1957 | Teng et al. |
| 3,024,379 A | 3/1962 | Verster |
| 3,175,131 A | 3/1965 | Burleigh et al. |
| 3,432,721 A | 3/1969 | Naydan et al. |
| 3,582,650 A | 6/1971 | Avery |
| 3,679,899 A | 7/1972 | Dimeff |
| 3,689,847 A | 9/1972 | Verster |
| 3,757,118 A | 9/1973 | Hodge et al. |
| 3,868,522 A | 2/1975 | Bigham et al. |
| 3,883,761 A | 5/1975 | Hendry |
| 3,886,367 A | 5/1975 | Castle |
| 3,925,676 A | 12/1975 | Bigham et al. |
| 2,958,327 A | 5/1976 | Marancik et al. |
| 3,955,089 A | 5/1976 | McIntyre et al. |
| 3,958,327 A | 5/1976 | Marancik et al. |
| 3,992,625 A | 11/1976 | Schmidt et al. |
| 4,038,622 A | 7/1977 | Purcell |
| 4,047,068 A | 9/1977 | Ress et al. |
| 4,095,201 A | 6/1978 | Kervizic |
| 4,112,306 A | 9/1978 | Nunan |
| 4,129,784 A | 12/1978 | Tschunt et al. |
| 4,139,777 A | 2/1979 | Rautenbach |
| 4,197,510 A | 4/1980 | Szu |
| 4,220,866 A | 9/1980 | Symmons et al. |
| 4,230,129 A | 10/1980 | LeVeen |
| 4,256,966 A | 3/1981 | Heinz |
| 4,293,772 A | 10/1981 | Stieber |
| 4,336,505 A | 6/1982 | Meyer |
| 4,342,060 A | 7/1982 | Gibson |
| 4,345,210 A | 8/1982 | Tran |
| 4,353,033 A | 10/1982 | Karasawa |
| 4,425,506 A | 1/1984 | Brown et al. |
| 4,490,616 A | 12/1984 | Cipollina et al. |
| 4,507,614 A | 3/1985 | Prono et al. |
| 4,507,616 A | 3/1985 | Blosser et al. |
| 4,589,126 A | 5/1986 | Augustsson et al. |
| 4,598,208 A | 7/1986 | Brunelli et al. |
| 4,628,523 A | 12/1986 | Heflin |
| 4,633,125 A | 12/1986 | Blosser et al. |
| 4,641,057 A | 2/1987 | Blosser et al. |
| 4,641,104 A | 2/1987 | Blosser et al. |
| 4,651,007 A | 3/1987 | Perusek et al. |
| 4,680,565 A | 7/1987 | Jahnke |
| 4,705,955 A | 11/1987 | Mileikowsky |
| 4,710,722 A | 12/1987 | Jahnke |
| 4,726,046 A | 2/1988 | Nunan |
| 4,734,653 A | 3/1988 | Jahnke |
| 4,737,727 A | 4/1988 | Yamada et al. |
| 4,739,173 A | 4/1988 | Blosser et al. |
| 4,745,367 A | 5/1988 | Dustmann et al. |
| 4,754,147 A | 6/1988 | Maughan et al. |
| 4,763,483 A | 8/1988 | Olsen |
| 4,767,930 A | 8/1988 | Stieber et al. |
| 4,769,623 A | 9/1988 | Marsing et al. |
| 4,771,208 A | 9/1988 | Jongen et al. |
| 4,783,634 A | 11/1988 | Yamamoto et al. |
| 4,808,941 A | 2/1989 | Marsing |
| 4,812,658 A | 3/1989 | Koehler |
| 4,843,333 A | 6/1989 | Marsing et al. |
| 4,845,371 A | 7/1989 | Stieber |
| 4,865,284 A | 9/1989 | Gosis et al. |
| 4,868,843 A | 9/1989 | Nunan |
| 4,868,844 A | 9/1989 | Nunan |
| 4,870,287 A | 9/1989 | Cole et al. |
| 4,880,985 A | 11/1989 | Jones |
| 4,894,541 A | 1/1990 | Ono |
| 4,896,206 A | 1/1990 | Denham |
| 4,902,993 A | 2/1990 | Krevet |
| 4,904,949 A | 2/1990 | Wilson |
| 4,905,267 A | 2/1990 | Miller et al. |
| 4,917,344 A | 4/1990 | Prechter et al. |
| 4,943,781 A | 7/1990 | Wilson et al. |
| 4,945,478 A | 7/1990 | Merickel et al. |
| 4,968,915 A | 11/1990 | Wilson et al. |
| 4,987,309 A | 1/1991 | Klasen et al. |
| 4,992,744 A | 2/1991 | Fujita et al. |
| 4,996,496 A | 2/1991 | Kitamura et al. |
| 5,006,759 A | 4/1991 | Krispel |
| 5,010,562 A | 4/1991 | Hernandez et al. |
| 5,012,111 A | 4/1991 | Ueda |
| 5,017,789 A | 5/1991 | Young et al. |
| 5,017,882 A | 5/1991 | Finlan |
| 5,036,290 A | 7/1991 | Sonobe et al. |
| 5,039,057 A | 8/1991 | Prechter et al. |
| 5,039,867 A | 8/1991 | Nishihara et al. |
| 5,046,078 A | 9/1991 | Hernandez et al. |
| 5,072,123 A | 12/1991 | Johnsen |
| 5,111,042 A | 5/1992 | Sullivan et al. |
| 5,111,173 A | 5/1992 | Matsuda et al. |
| 5,117,194 A | 5/1992 | Nakanishi et al. |
| 5,117,212 A | 5/1992 | Yamamoto et al. |
| 5,117,829 A | 6/1992 | Miller et al. |
| 5,148,032 A | 9/1992 | Hernandez |
| 5,166,531 A | 11/1992 | Huntzinger |
| 5,189,687 A | 2/1993 | Bova et al. |
| 5,191,706 A | 3/1993 | Cosden |
| 5,240,218 A | 8/1993 | Dye |
| 5,260,579 A | 11/1993 | Yasuda et al. |
| 5,260,581 A | 11/1993 | Lesyna et al. |
| 5,278,533 A | 1/1994 | Kawaguchi |
| 5,285,166 A | 2/1994 | Hiramoto et al. |
| 5,317,164 A | 5/1994 | Kurokawa |
| 5,336,891 A | 8/1994 | Crewe |
| 5,341,104 A | 8/1994 | Anton et al. |
| 5,349,198 A | 9/1994 | Takanaka |
| 5,365,742 A | 11/1994 | Boffito et al. |
| 5,374,913 A | 12/1994 | Pissantezky et al. |
| 5,382,914 A | 1/1995 | Hamm et al. |
| 5,401,973 A | 3/1995 | McKeown et al. |
| 5,405,235 A | 4/1995 | Lebre et al. |
| 5,434,420 A | 7/1995 | McKeown et al. |
| 5,440,133 A | 8/1995 | Moyers et al. |
| 5,451,794 A | 9/1995 | McKeown et al. |
| 5,461,773 A | 10/1995 | Kawaguchi |
| 5,463,291 A | 10/1995 | Carroll et al. |
| 5,464,411 A | 11/1995 | Schulte et al. |
| 5,492,922 A | 2/1996 | Palkowitz |
| 5,511,549 A | 4/1996 | Legg et al. |
| 5,521,469 A | 5/1996 | Laisne |
| 5,538,942 A | 7/1996 | Koyama et al. |
| 5,549,616 A | 8/1996 | Schulte et al. |
| 5,561,697 A | 10/1996 | Takafuji et al. |
| 5,585,642 A | 12/1996 | Britton et al. |
| 5,633,747 A | 5/1997 | Nikoonahad |
| 5,635,721 A | 6/1997 | Bardi et al. |
| 5,668,371 A | 9/1997 | Deasy et al. |
| 5,672,878 A | 9/1997 | Yao |
| 5,691,679 A | 11/1997 | Ackermann et al. |
| 5,717,371 A | 2/1998 | Crow |
| 5,726,448 A | 3/1998 | Smith et al. |
| 5,727,554 A | 3/1998 | Kalend et al. |
| 5,730,745 A | 3/1998 | Schulte et al. |
| 5,751,781 A | 5/1998 | Brown et al. |
| 5,778,047 A | 7/1998 | Mansfield et al. |
| 5,783,914 A | 7/1998 | Hiramoto et al. |
| 5,784,431 A | 7/1998 | Kalend et al. |

(56) References Cited

U.S. PATENT DOCUMENTS

| | | |
|---|---|---|
| 5,797,924 A | 8/1998 | Schulte et al. |
| 5,811,944 A | 9/1998 | Sampayan et al. |
| 5,818,058 A | 10/1998 | Nakanishi et al. |
| 5,821,705 A | 10/1998 | Caporaso et al. |
| 5,825,845 A | 10/1998 | Blair et al. |
| 5,841,237 A | 11/1998 | Alton |
| 5,846,043 A | 12/1998 | Spath |
| 5,851,182 A | 12/1998 | Sahadevan |
| 5,866,912 A | 2/1999 | Slater et al. |
| 5,874,811 A | 2/1999 | Finlan et al. |
| 5,895,926 A | 4/1999 | Britton et al. |
| 5,920,601 A | 7/1999 | Nigg et al. |
| 5,929,458 A | 7/1999 | Nemezawa et al. |
| 5,963,615 A | 10/1999 | Egley et al. |
| 5,993,373 A | 11/1999 | Nonaka et al. |
| 6,008,499 A | 12/1999 | Hiramoto et al. |
| 6,034,377 A | 3/2000 | Pu |
| 6,057,655 A | 5/2000 | Jongen |
| 6,061,426 A | 5/2000 | Linders et al. |
| 6,064,807 A | 5/2000 | Arai et al. |
| 6,066,851 A | 5/2000 | Madono et al. |
| 6,080,992 A | 6/2000 | Nonaka et al. |
| 6,087,670 A | 7/2000 | Hiramoto et al. |
| 6,094,760 A | 8/2000 | Nonaka et al. |
| 6,118,848 A | 9/2000 | Reiffel |
| 6,140,021 A | 10/2000 | Nakasuji et al. |
| 6,144,875 A | 11/2000 | Schweikard et al. |
| 6,158,708 A | 12/2000 | Egley et al. |
| 6,207,952 B1 | 3/2001 | Kan et al. |
| 6,219,403 B1 | 4/2001 | Nishihara |
| 6,222,905 B1 | 4/2001 | Yoda et al. |
| 6,241,671 B1 | 6/2001 | Ritter et al. |
| 6,246,066 B1 | 6/2001 | Yuehu |
| 6,256,591 B1 | 7/2001 | Yoda et al. |
| 6,265,837 B1 | 7/2001 | Akiyama et al. |
| 6,268,610 B1 | 7/2001 | Pu |
| 6,278,239 B1 | 8/2001 | Caporaso et al. |
| 6,279,579 B1 | 8/2001 | Riaziat et al. |
| 6,307,914 B1 | 10/2001 | Kunieda et al. |
| 6,316,776 B1 | 11/2001 | Hiramoto et al. |
| 6,366,021 B1 | 4/2002 | Meddaugh et al. |
| 6,369,585 B2 | 4/2002 | Yao |
| 6,380,545 B1 | 4/2002 | Yan |
| 6,407,505 B1 | 6/2002 | Bertsche |
| 6,417,634 B1 | 7/2002 | Bergstrom |
| 6,433,336 B1 | 8/2002 | Jongen et al. |
| 6,433,349 B2 | 8/2002 | Akiyama et al. |
| 6,433,494 B1 | 8/2002 | Kulish et al. |
| 6,441,569 B1 | 8/2002 | Janzow |
| 6,443,349 B1 | 9/2002 | Van Der Burg |
| 6,465,957 B1 | 10/2002 | Whitham et al. |
| 6,472,834 B2 | 10/2002 | Hiramoto et al. |
| 6,476,403 B1 | 11/2002 | Dolinskii et al. |
| 6,492,922 B1 | 12/2002 | New |
| 6,493,424 B2 | 12/2002 | Whitham |
| 6,498,444 B1 | 12/2002 | Hanna et al. |
| 6,501,961 B1 | 12/2002 | Kirkpatrick |
| 6,501,981 B1 | 12/2002 | Schweikard et al. |
| 6,519,316 B1 | 2/2003 | Collins |
| 6,593,696 B2 | 7/2003 | Ding et al. |
| 6,594,336 B2 | 7/2003 | Nishizawa et al. |
| 6,600,164 B1 | 7/2003 | Badura et al. |
| 6,617,598 B1 | 9/2003 | Matsuda |
| 6,621,889 B1 | 9/2003 | Mostafavi |
| 6,639,234 B1 | 10/2003 | Badura et al. |
| 6,646,383 B2 | 11/2003 | Bertsche et al. |
| 6,670,618 B1 | 12/2003 | Hartmann et al. |
| 6,683,318 B1 | 1/2004 | Haberer et al. |
| 6,683,426 B1 | 1/2004 | Kleeven |
| 6,693,283 B2 | 2/2004 | Eickhoff et al. |
| 6,710,362 B2 | 3/2004 | Kraft et al. |
| 6,713,773 B1 | 3/2004 | Lyons et al. |
| 6,713,976 B1 | 3/2004 | Zumoto et al. |
| 6,717,162 B1 | 4/2004 | Jongen |
| 6,736,831 B1 | 5/2004 | Hartmann et al. |
| 6,745,072 B1 | 6/2004 | Badura et al. |
| 6,769,806 B2 | 8/2004 | Moyers |
| 6,774,383 B2 | 8/2004 | Norimine et al. |
| 6,777,689 B2 | 8/2004 | Nelson |
| 6,777,700 B2 | 8/2004 | Yanagisawa et al. |
| 6,780,149 B1 | 8/2004 | Schulte |
| 6,794,868 B1 | 9/2004 | Wong et al. |
| 6,799,068 B1 | 9/2004 | Hartmann et al. |
| 6,800,866 B2 | 10/2004 | Amemiya et al. |
| 6,803,591 B2 | 10/2004 | Muramatsu et al. |
| 6,814,694 B1 | 11/2004 | Pedroni |
| 6,822,244 B2 | 11/2004 | Beloussov et al. |
| 6,853,142 B2 | 2/2005 | Chistyakov |
| 6,853,703 B2 | 2/2005 | Svatos et al. |
| 6,864,770 B2 | 3/2005 | Nemoto et al. |
| 6,865,254 B2 | 3/2005 | Nafstadius |
| 6,873,123 B2 | 3/2005 | Marchand et al. |
| 6,891,177 B1 | 5/2005 | Kraft et al. |
| 6,891,924 B1 | 5/2005 | Yoda et al. |
| 6,894,300 B2 | 5/2005 | Reimoser et al. |
| 6,897,451 B2 | 5/2005 | Kaercher et al. |
| 6,914,396 B1 | 7/2005 | Symons et al. |
| 6,936,832 B2 | 8/2005 | Norimine et al. |
| 6,953,943 B2 | 10/2005 | Yanagisawa et al. |
| 6,965,116 B1 | 11/2005 | Wagner et al. |
| 6,969,194 B1 | 11/2005 | Nafstadius |
| 6,979,832 B2 | 12/2005 | Yanagisawa et al. |
| 6,984,835 B2 | 1/2006 | Harada |
| 6,992,312 B2 | 1/2006 | Yanagisawa et al. |
| 6,993,112 B2 | 1/2006 | Hesse |
| 7,008,105 B2 | 3/2006 | Amann et al. |
| 7,011,447 B2 | 3/2006 | Moyers |
| 7,012,267 B2 | 3/2006 | Moriyama et al. |
| 7,014,361 B1 | 3/2006 | Ein-Gal |
| 7,026,636 B2 | 4/2006 | Yanagisawa et al. |
| 7,038,403 B2 | 5/2006 | Mastrangeli et al. |
| 7,041,479 B2 | 5/2006 | Swartz et al. |
| 7,045,781 B2 | 5/2006 | Adamec et al. |
| 7,049,613 B2 | 5/2006 | Yanagisawa et al. |
| 7,053,389 B2 | 5/2006 | Yanagisawa et al. |
| 7,054,801 B2 | 5/2006 | Sakamoto et al. |
| 7,060,997 B2 | 6/2006 | Norimine et al. |
| 7,071,479 B2 | 7/2006 | Yanagisawa et al. |
| 7,073,508 B2 | 7/2006 | Moyers |
| 7,081,619 B2 | 7/2006 | Bashkirov et al. |
| 7,084,410 B2 | 8/2006 | Beloussov et al. |
| 7,091,478 B2 | 8/2006 | Haberer |
| 7,102,144 B2 | 9/2006 | Matsuda et al. |
| 7,122,811 B2 | 10/2006 | Matsuda et al. |
| 7,122,966 B2 | 10/2006 | Norling et al. |
| 7,122,978 B2 | 10/2006 | Nakanishi et al. |
| 7,135,678 B2 | 11/2006 | Wang et al. |
| 7,138,771 B2 | 11/2006 | Bechthold et al. |
| 7,154,107 B2 | 12/2006 | Yanagisawa et al. |
| 7,154,108 B2 | 12/2006 | Tadokoro et al. |
| 7,154,991 B2 | 12/2006 | Earnst et al. |
| 7,162,005 B2 | 1/2007 | Bjorkholm |
| 7,173,264 B2 | 2/2007 | Moriyama et al. |
| 7,173,265 B2 | 2/2007 | Miller et al. |
| 7,173,385 B2 | 2/2007 | Caporaso et al. |
| 7,186,991 B2 | 3/2007 | Kato et al. |
| 7,193,227 B2 | 3/2007 | Hiramoto et al. |
| 7,199,382 B2 | 4/2007 | Rigney et al. |
| 7,208,748 B2 | 4/2007 | Sliski et al. |
| 7,212,608 B2 | 5/2007 | Nagamine et al. |
| 7,212,609 B2 | 5/2007 | Nagamine et al. |
| 7,221,733 B1 | 5/2007 | Takai et al. |
| 7,227,161 B2 | 6/2007 | Matsuda et al. |
| 7,247,869 B2 | 7/2007 | Tadokoro et al. |
| 7,257,191 B2 | 8/2007 | Sommer |
| 7,259,529 B2 | 8/2007 | Tanaka |
| 7,262,424 B2 | 8/2007 | Moriyama et al. |
| 7,262,565 B2 | 8/2007 | Fujisawa |
| 7,274,018 B2 | 9/2007 | Adamec et al. |
| 7,280,633 B2 | 10/2007 | Cheng et al. |
| 7,295,649 B2 | 11/2007 | Johnsen |
| 7,297,967 B2 | 11/2007 | Yanagisawa et al. |
| 7,301,162 B2 | 11/2007 | Matsuda et al. |
| 7,307,264 B2 | 12/2007 | Brusasco et al. |

(56) References Cited

U.S. PATENT DOCUMENTS

| | | |
|---|---|---|
| 7,318,805 B2 | 1/2008 | Schweikard et al. |
| 7,319,231 B2 | 1/2008 | Moriyama et al. |
| 7,319,336 B2 | 1/2008 | Bauer et al. |
| 7,331,713 B2 | 2/2008 | Moyers |
| 7,332,880 B2 | 2/2008 | Ina et al. |
| 7,345,291 B2 | 3/2008 | Kats |
| 7,345,292 B2 | 3/2008 | Moriyama et al. |
| 7,348,557 B2 | 3/2008 | Armit |
| 7,348,579 B2 | 3/2008 | Pedroni |
| 7,351,988 B2 | 4/2008 | Naumann et al. |
| 7,355,189 B2 | 4/2008 | Yanagisawa et al. |
| 7,368,740 B2 | 5/2008 | Beloussov et al. |
| 7,372,053 B2 | 5/2008 | Yamashita et al. |
| 7,378,672 B2 | 5/2008 | Harada |
| 7,381,979 B2 | 6/2008 | Yamashita et al. |
| 7,397,054 B2 | 7/2008 | Natori et al. |
| 7,397,901 B1 | 7/2008 | Johnsen |
| 7,398,309 B2 | 7/2008 | Baumann et al. |
| 7,402,822 B2 | 7/2008 | Guertin et al. |
| 7,402,823 B2 | 7/2008 | Guertin et al. |
| 7,402,824 B2 | 7/2008 | Guertin et al. |
| 7,402,963 B2 | 7/2008 | Sliski |
| 7,405,407 B2 | 7/2008 | Hiramoto et al. |
| 7,425,717 B2 | 9/2008 | Matsuda et al. |
| 7,432,516 B2 | 10/2008 | Peggs et al. |
| 7,439,528 B2 | 10/2008 | Nishiuchi et al. |
| 7,446,328 B2 | 11/2008 | Rigney et al. |
| 7,446,490 B2 | 11/2008 | Jongen et al. |
| 7,449,701 B2 | 11/2008 | Fujimaki et al. |
| 7,453,076 B2 | 11/2008 | Welch et al. |
| 7,465,944 B2 | 12/2008 | Ueno et al. |
| 7,466,085 B2 | 12/2008 | Nutt |
| 7,468,506 B2 | 12/2008 | Rogers et al. |
| 7,473,913 B2 | 1/2009 | Hermann et al. |
| 7,476,867 B2 | 1/2009 | Fritsch et al. |
| 7,476,883 B2 | 1/2009 | Nutt |
| 7,482,606 B2 | 1/2009 | Groezinger et al. |
| 7,492,556 B2 | 2/2009 | Atkins et al. |
| 7,507,975 B2 | 3/2009 | Mohr |
| 7,525,104 B2 | 4/2009 | Harada |
| 7,541,905 B2 | 6/2009 | Antaya |
| 7,547,901 B2 | 6/2009 | Guertin et al. |
| 7,554,096 B2 | 6/2009 | Ward et al. |
| 7,554,097 B2 | 6/2009 | Ward et al. |
| 7,555,103 B2 | 6/2009 | Johnsen |
| 7,557,358 B2 | 7/2009 | Ward et al. |
| 7,557,359 B2 | 7/2009 | Ward et al. |
| 7,557,360 B2 | 7/2009 | Ward et al. |
| 7,557,361 B2 | 7/2009 | Ward et al. |
| 7,560,715 B2 | 7/2009 | Pedroni |
| 7,560,717 B2 | 7/2009 | Matsuda et al. |
| 7,567,694 B2 | 7/2009 | Lu et al. |
| 7,574,251 B2 | 8/2009 | Lu et al. |
| 7,576,499 B2 | 8/2009 | Caporaso et al. |
| 7,579,603 B2 | 8/2009 | Birgy et al. |
| 7,579,610 B2 | 8/2009 | Grozinger et al. |
| 7,582,866 B2 | 9/2009 | Furuhashi et al. |
| 7,582,885 B2 | 9/2009 | Katagiri et al. |
| 7,582,886 B2 | 9/2009 | Trbojevic |
| 7,586,112 B2 | 9/2009 | Chiba et al. |
| 7,598,497 B2 | 10/2009 | Yamamoto et al. |
| 7,609,009 B2 | 10/2009 | Tanaka et al. |
| 7,609,809 B2 | 10/2009 | Kapatoes et al. |
| 7,609,811 B1 | 10/2009 | Siljamaki et al. |
| 7,615,942 B2 | 11/2009 | Sanders et al. |
| 7,626,347 B2 | 12/2009 | Sliski et al. |
| 7,629,598 B2 | 12/2009 | Harada |
| 7,639,853 B2 | 12/2009 | Olivera et al. |
| 7,639,854 B2 | 12/2009 | Schnarr et al. |
| 7,643,661 B2 | 1/2010 | Ruchala et al. |
| 7,656,258 B1 | 2/2010 | Antaya et al. |
| 7,659,521 B2 | 2/2010 | Pedroni |
| 7,659,528 B2 | 2/2010 | Uematsu |
| 7,668,291 B2 | 2/2010 | Nord et al. |
| 7,672,429 B2 | 3/2010 | Urano et al. |
| 7,679,073 B2 | 3/2010 | Urano et al. |
| 7,682,078 B2 | 3/2010 | Rietzel |
| 7,692,166 B2 | 4/2010 | Muraki et al. |
| 7,692,168 B2 | 4/2010 | Moriyama et al. |
| 7,696,499 B2 | 4/2010 | Miller et al. |
| 7,696,847 B2 | 4/2010 | Antaya |
| 7,701,677 B2 | 4/2010 | Schultz et al. |
| 7,709,818 B2 | 5/2010 | Matsuda et al. |
| 7,710,051 B2 | 5/2010 | Caporaso et al. |
| 7,718,982 B2 | 5/2010 | Sliski |
| 7,728,311 B2 | 6/2010 | Gall |
| 7,746,978 B2 | 6/2010 | Cheng et al. |
| 7,755,305 B2 | 7/2010 | Umezawa et al. |
| 7,759,642 B2 | 7/2010 | Nir |
| 7,763,867 B2 | 7/2010 | Birgy et al. |
| 7,767,988 B2 | 8/2010 | Kaiser et al. |
| 7,770,231 B2 | 8/2010 | Prater et al. |
| 7,772,577 B2 | 8/2010 | Saito et al. |
| 7,773,723 B2 | 8/2010 | Nord et al. |
| 7,773,788 B2 | 8/2010 | Lu et al. |
| 7,778,488 B2 | 8/2010 | Nord et al. |
| 7,783,010 B2 | 8/2010 | Clayton |
| 7,784,127 B2 | 8/2010 | Kuro et al. |
| 7,786,451 B2 | 8/2010 | Ward et al. |
| 7,786,452 B2 | 8/2010 | Ward et al. |
| 7,789,560 B2 | 9/2010 | Moyers |
| 7,791,051 B2 | 9/2010 | Beloussov et al. |
| 7,796,731 B2 | 9/2010 | Nord et al. |
| 7,801,269 B2 | 9/2010 | Cravens et al. |
| 7,801,270 B2 | 9/2010 | Nord et al. |
| 7,801,988 B2 | 9/2010 | Baumann et al. |
| 7,807,982 B2 | 10/2010 | Nishiuchi et al. |
| 7,809,107 B2 | 10/2010 | Nord et al. |
| 7,812,319 B2 | 10/2010 | Diehl et al. |
| 7,812,326 B2 | 10/2010 | Grozinger et al. |
| 7,816,657 B2 | 10/2010 | Hansmann et al. |
| 7,817,778 B2 | 10/2010 | Nord et al. |
| 7,817,836 B2 | 10/2010 | Chao et al. |
| 7,834,334 B2 | 11/2010 | Grozinger et al. |
| 7,834,336 B2 | 11/2010 | Boeh et al. |
| 7,835,494 B2 | 11/2010 | Nord et al. |
| 7,835,502 B2 | 11/2010 | Spence et al. |
| 7,839,972 B2 | 11/2010 | Ruchala et al. |
| 7,839,973 B2 | 11/2010 | Nord et al. |
| 7,848,488 B2 | 12/2010 | Mansfield |
| 7,857,756 B2 | 12/2010 | Warren et al. |
| 7,860,216 B2 | 12/2010 | Jongen et al. |
| 7,860,550 B2 | 12/2010 | Saracen et al. |
| 7,868,301 B2 | 1/2011 | Diehl |
| 7,875,801 B2 | 1/2011 | Tsotsis |
| 7,875,861 B2 | 1/2011 | Huttenberger et al. |
| 7,875,868 B2 | 1/2011 | Moriyama et al. |
| 7,881,431 B2 | 2/2011 | Aoi et al. |
| 7,894,574 B1 | 2/2011 | Nord et al. |
| 7,906,769 B2 | 3/2011 | Blasche et al. |
| 7,914,734 B2 | 3/2011 | Livingston |
| 7,919,765 B2 | 4/2011 | Timmer |
| 7,920,040 B2 | 4/2011 | Antaya et al. |
| 7,920,675 B2 | 4/2011 | Lomax et al. |
| 7,928,415 B2 | 4/2011 | Bert et al. |
| 7,934,869 B2 | 5/2011 | Ivanov et al. |
| 7,940,881 B2 | 5/2011 | Jongen et al. |
| 7,943,913 B2 | 5/2011 | Balakin |
| 7,947,969 B2 | 5/2011 | Pu |
| 7,949,096 B2 | 5/2011 | Cheng et al. |
| 7,950,587 B2 | 5/2011 | Henson et al. |
| 7,960,710 B2 | 6/2011 | Kruip et al. |
| 7,961,844 B2 | 6/2011 | Takeda et al. |
| 7,977,648 B2 | 7/2011 | Westerly et al. |
| 7,977,656 B2 | 7/2011 | Fujimaki et al. |
| 7,982,198 B2 | 7/2011 | Nishiuchi et al. |
| 7,982,416 B2 | 7/2011 | Tanaka et al. |
| 7,984,715 B2 | 7/2011 | Moyers |
| 7,986,768 B2 | 7/2011 | Nord et al. |
| 7,987,053 B2 | 7/2011 | Schaffner |
| 7,989,785 B2 | 8/2011 | Emhofer et al. |
| 7,990,524 B2 | 8/2011 | Jureller et al. |
| 7,997,553 B2 | 8/2011 | Sloan et al. |
| 8,002,466 B2 | 8/2011 | Von Neubeck et al. |

(56) References Cited

U.S. PATENT DOCUMENTS

| | | | |
|---|---|---|---|
| 8,003,964 B2 | 8/2011 | Stark et al. | |
| 8,009,803 B2 | 8/2011 | Nord et al. | |
| 8,009,804 B2 | 8/2011 | Siljamaki et al. | |
| 8,039,822 B2 | 10/2011 | Rietzel | |
| 8,041,006 B2 | 10/2011 | Boyden et al. | |
| 8,044,364 B2 | 10/2011 | Yamamoto | |
| 8,049,187 B2 | 11/2011 | Tachikawa | |
| 8,053,508 B2 | 11/2011 | Korkut et al. | |
| 8,053,739 B2 | 11/2011 | Rietzel | |
| 8,053,745 B2 | 11/2011 | Moore | |
| 8,053,746 B2 | 11/2011 | Timmer et al. | |
| 8,067,748 B2 | 11/2011 | Balakin | |
| 8,069,675 B2 | 12/2011 | Radovinsky et al. | |
| 8,071,966 B2 | 12/2011 | Kaiser et al. | |
| 8,080,801 B2 | 12/2011 | Safai | |
| 8,085,899 B2 | 12/2011 | Nord et al. | |
| 8,089,054 B2 | 1/2012 | Balakin | |
| 8,093,564 B2 | 1/2012 | Balakin | |
| 8,093,568 B2 | 1/2012 | Mackie et al. | |
| 8,111,125 B2 | 2/2012 | Antaya et al. | |
| 8,129,699 B2 * | 3/2012 | Balakin | A61N 5/1049 |
| | | | 250/396 R |
| 8,144,832 B2 | 3/2012 | Balakin | |
| 8,153,989 B2 | 4/2012 | Tachikawa et al. | |
| 8,173,981 B2 | 5/2012 | Trbojevic | |
| 8,188,688 B2 * | 5/2012 | Balakin | H05H 7/04 |
| | | | 250/298 |
| 8,198,607 B2 | 6/2012 | Balakin | |
| 8,222,613 B2 | 7/2012 | Tajiri et al. | |
| 8,227,768 B2 | 7/2012 | Smick et al. | |
| 8,232,536 B2 | 7/2012 | Harada | |
| 8,278,634 B2 | 10/2012 | Vanderberg et al. | |
| 8,288,742 B2 | 10/2012 | Balakin | |
| 8,291,717 B2 | 10/2012 | Radovinsky et al. | |
| 8,294,127 B2 | 10/2012 | Tachibana | |
| 8,304,725 B2 | 11/2012 | Komuro et al. | |
| 8,304,750 B2 | 11/2012 | Preikszas et al. | |
| 8,309,941 B2 | 11/2012 | Balakin | |
| 8,330,132 B2 | 12/2012 | Guertin et al. | |
| 8,334,520 B2 | 12/2012 | Otaka et al. | |
| 8,335,397 B2 | 12/2012 | Takane et al. | |
| 8,344,340 B2 | 1/2013 | Gall | |
| 8,350,214 B2 | 1/2013 | Otaki et al. | |
| 8,368,038 B2 | 2/2013 | Balakin | |
| 8,368,043 B2 | 2/2013 | Havelange et al. | |
| 8,373,143 B2 | 2/2013 | Balakin | |
| 8,373,145 B2 | 2/2013 | Balakin | |
| 8,373,146 B2 * | 2/2013 | Balakin | H05H 7/10 |
| | | | 250/396 R |
| 8,378,299 B2 | 2/2013 | Frosien | |
| 8,378,321 B2 | 2/2013 | Balakin | |
| 8,382,943 B2 | 2/2013 | Clark | |
| 8,389,949 B2 | 3/2013 | Harada et al. | |
| 8,399,866 B2 | 3/2013 | Balakin | |
| 8,405,042 B2 | 3/2013 | Honda et al. | |
| 8,405,056 B2 | 3/2013 | Amaldi et al. | |
| 8,415,643 B2 | 4/2013 | Balakin | |
| 8,416,918 B2 | 4/2013 | Nord et al. | |
| 8,421,041 B2 | 4/2013 | Balakin | |
| 8,426,833 B2 | 4/2013 | Trbojevic | |
| 8,436,323 B2 | 5/2013 | Iseki et al. | |
| 8,440,987 B2 | 5/2013 | Stephani et al. | |
| 8,445,872 B2 | 5/2013 | Behrens et al. | |
| 8,466,441 B2 | 6/2013 | Iwata et al. | |
| 8,472,583 B2 | 6/2013 | Star-Lack et al. | |
| 8,483,357 B2 | 7/2013 | Siljamaki et al. | |
| 8,487,278 B2 | 7/2013 | Balakin | |
| 8,502,173 B2 | 8/2013 | Vanderberg et al. | |
| 8,552,406 B2 | 10/2013 | Phaneuf et al. | |
| 8,552,408 B2 | 10/2013 | Hanawa et al. | |
| 8,569,717 B2 | 10/2013 | Balakin | |
| 8,575,563 B2 * | 11/2013 | Cameron | A61N 5/10 |
| | | | 250/396 ML |
| 8,581,125 B2 | 11/2013 | Chen | |
| 8,581,215 B2 | 11/2013 | Balakin | |
| 8,581,523 B2 | 11/2013 | Gall et al. | |
| 8,581,525 B2 | 11/2013 | Antaya et al. | |
| 8,637,833 B2 * | 1/2014 | Balakin | A61N 5/10 |
| | | | 250/396 R |
| 8,643,314 B2 | 2/2014 | Touchi | |
| 8,653,314 B2 | 2/2014 | Pelati et al. | |
| 8,653,473 B2 | 2/2014 | Yajima | |
| 8,791,435 B2 * | 7/2014 | Balakin | A61N 5/10 |
| | | | 250/396 R |
| 8,791,656 B1 | 7/2014 | Zwart et al. | |
| 8,901,509 B2 * | 12/2014 | Balakin | G21K 1/087 |
| | | | 250/396 ML |
| 8,927,950 B2 | 1/2015 | Gall et al. | |
| 8,963,112 B1 * | 2/2015 | Balakin | A61N 5/1049 |
| | | | 250/396 R |
| 8,975,816 B2 * | 3/2015 | Scheitrum | H01J 23/38 |
| | | | 315/5.16 |
| 8,975,836 B2 | 3/2015 | Bromberg et al. | |
| 9,012,866 B2 * | 4/2015 | Benna | A61N 5/1077 |
| | | | 250/396 ML |
| 9,044,600 B2 * | 6/2015 | Balakin | A61N 5/10 |
| 9,056,199 B2 * | 6/2015 | Balakin | A61N 5/10 |
| 2002/0172317 A1 | 11/2002 | Maksimchuk et al. | |
| 2003/0048080 A1 | 3/2003 | Amemiya et al. | |
| 2003/0125622 A1 | 7/2003 | Schweikard et al. | |
| 2003/0136924 A1 | 7/2003 | Kraft et al. | |
| 2003/0152197 A1 | 8/2003 | Moyers | |
| 2003/0163015 A1 | 8/2003 | Yanagisawa et al. | |
| 2003/0183779 A1 | 10/2003 | Norimine et al. | |
| 2003/0234369 A1 | 12/2003 | Glukhoy | |
| 2004/0000650 A1 | 1/2004 | Yanagisawa et al. | |
| 2004/0017888 A1 | 1/2004 | Seppi et al. | |
| 2004/0056212 A1 | 3/2004 | Yanagisawa et al. | |
| 2004/0061077 A1 | 4/2004 | Muramatsu et al. | |
| 2004/0061078 A1 | 4/2004 | Muramatsu et al. | |
| 2004/0085023 A1 | 5/2004 | Chistyakov | |
| 2004/0098445 A1 | 5/2004 | Baumann et al. | |
| 2004/0111134 A1 | 6/2004 | Muramatsu et al. | |
| 2004/0118081 A1 | 6/2004 | Reimoser et al. | |
| 2004/0149934 A1 | 8/2004 | Yanagisawa et al. | |
| 2004/0159795 A1 | 8/2004 | Kaercher et al. | |
| 2004/0173763 A1 | 9/2004 | Moriyama et al. | |
| 2004/0174958 A1 | 9/2004 | Moriyama et al. | |
| 2004/0183033 A1 | 9/2004 | Moriyama et al. | |
| 2004/0183035 A1 | 9/2004 | Yanagisawa et al. | |
| 2004/0200982 A1 | 10/2004 | Moriyama et al. | |
| 2004/0200983 A1 | 10/2004 | Fujimaki et al. | |
| 2004/0213381 A1 | 10/2004 | Harada | |
| 2004/0227104 A1 | 11/2004 | Matsuda et al. | |
| 2004/0232356 A1 | 11/2004 | Norimine et al. | |
| 2004/0240626 A1 | 12/2004 | Moyers | |
| 2005/0058245 A1 | 3/2005 | Ein-Gal | |
| 2005/0089141 A1 | 4/2005 | Brown | |
| 2005/0161618 A1 | 7/2005 | Pedroni | |
| 2005/0184686 A1 | 8/2005 | Caporaso et al. | |
| 2005/0228255 A1 | 10/2005 | Saracen et al. | |
| 2005/0234327 A1 | 10/2005 | Saracen et al. | |
| 2005/0247890 A1 | 11/2005 | Norimine et al. | |
| 2006/0017015 A1 * | 1/2006 | Sliski | A61N 5/1077 |
| | | | 250/492.3 |
| 2006/0067468 A1 | 3/2006 | Rietzel | |
| 2006/0126792 A1 | 6/2006 | Li | |
| 2006/0145088 A1 | 7/2006 | Ma | |
| 2006/0175991 A1 | 8/2006 | Fujisawa | |
| 2006/0284562 A1 | 12/2006 | Hruby et al. | |
| 2007/0001128 A1 | 1/2007 | Sliski et al. | |
| 2007/0013273 A1 | 1/2007 | Albert et al. | |
| 2007/0014654 A1 | 1/2007 | Haverfield et al. | |
| 2007/0023699 A1 | 2/2007 | Yamashita et al. | |
| 2007/0029510 A1 | 2/2007 | Hermann et al. | |
| 2007/0051904 A1 | 3/2007 | Kaiser et al. | |
| 2007/0092812 A1 | 4/2007 | Caporaso et al. | |
| 2007/0114945 A1 | 5/2007 | Mattaboni et al. | |
| 2007/0145916 A1 * | 6/2007 | Caporaso | H05H 9/02 |
| | | | 315/505 |
| 2007/0171015 A1 | 7/2007 | Antaya | |
| 2007/0181519 A1 | 8/2007 | Khoshnevis | |
| 2007/0284548 A1 | 12/2007 | Kaiser et al. | |

(56) References Cited

U.S. PATENT DOCUMENTS

| | | |
|---|---|---|
| 2008/0067452 A1 | 3/2008 | Moriyama et al. |
| 2008/0078937 A1 | 4/2008 | Tsuchiya et al. |
| 2008/0093567 A1 | 4/2008 | Gall |
| 2008/0218102 A1 | 9/2008 | Sliski |
| 2009/0096179 A1 | 4/2009 | Stark et al. |
| 2009/0140671 A1 | 6/2009 | O'Neal et al. |
| 2009/0140672 A1 | 6/2009 | Gall et al. |
| 2009/0200483 A1 | 8/2009 | Gall et al. |
| 2010/0045213 A1 | 2/2010 | Sliski et al. |
| 2010/0051833 A1 | 3/2010 | Guertin et al. |
| 2010/0230617 A1 | 9/2010 | Gall |
| 2010/0308235 A1 | 12/2010 | Sliski |
| 2011/0240874 A1 | 10/2011 | Iwata |
| 2011/0284760 A1 | 11/2011 | Balakin et al. |
| 2011/0299919 A1 | 12/2011 | Stark |
| 2012/0014501 A1 | 1/2012 | Pelc et al. |
| 2012/0019085 A1 | 1/2012 | Koga et al. |
| 2012/0081041 A1 | 4/2012 | Cheung et al. |
| 2012/0142538 A1 | 6/2012 | Antaya et al. |
| 2013/0009571 A1 | 1/2013 | Antaya |
| 2013/0053616 A1 | 2/2013 | Gall |
| 2013/0127375 A1 | 5/2013 | Sliski |
| 2013/0131424 A1 | 5/2013 | Sliski |
| 2013/0237425 A1 | 9/2013 | Leigh et al. |
| 2013/0249443 A1 | 9/2013 | Antaya et al. |
| 2014/0028220 A1 | 1/2014 | Bromberg et al. |
| 2014/0042934 A1 | 2/2014 | Tsutsui |
| 2014/0091734 A1 | 4/2014 | Gall et al. |
| 2014/0094371 A1 | 4/2014 | Zwart et al. |
| 2014/0094637 A1 | 4/2014 | Zwart et al. |
| 2014/0094638 A1 | 4/2014 | Gall et al. |
| 2014/0094639 A1 | 4/2014 | Zwart et al. |
| 2014/0094640 A1 | 4/2014 | Gall et al. |
| 2014/0094641 A1 | 4/2014 | Gall et al. |
| 2014/0094643 A1 | 4/2014 | Gall et al. |
| 2014/0097920 A1 | 4/2014 | Goldie et al. |
| 2014/0320006 A1 | 10/2014 | Abs et al. |
| 2014/0371511 A1 | 12/2014 | Zwart et al. |
| 2015/0161793 A1* | 6/2015 | Takahashi ............ A61N 5/1049 600/1 |

FOREIGN PATENT DOCUMENTS

| | | |
|---|---|---|
| CN | 1537657 A | 10/2004 |
| CN | 1816243 A | 8/2006 |
| CN | 1988933 A | 6/2007 |
| CN | 101361156 A | 2/2009 |
| CN | 101932361 | 12/2010 |
| CN | 101933405 | 12/2010 |
| CN | 101933406 | 12/2010 |
| CN | 101061759 | 5/2011 |
| CN | 102214494 A | 10/2011 |
| CN | 104244562 A | 12/2014 |
| CN | 104812443 A | 7/2015 |
| CN | 104812444 | 7/2015 |
| CN | 104822417 | 8/2015 |
| DE | 2753397 | 6/1978 |
| DE | 31 48 100 | 6/1983 |
| DE | 35 30 446 | 8/1984 |
| DE | 41 01 094 C1 | 5/1992 |
| DE | 4411171 | 10/1995 |
| EP | 0 194 728 | 9/1986 |
| EP | 0276123 | 7/1988 |
| EP | 0 277 521 | 8/1988 |
| EP | 0 208 163 | 1/1989 |
| EP | 0 222 786 | 7/1990 |
| EP | 0 221 987 | 1/1991 |
| EP | 0 499 253 | 8/1992 |
| EP | 0 306 966 | 4/1995 |
| EP | 0 388 123 | 5/1995 |
| EP | 0 465 597 | 5/1997 |
| EP | 0 911 064 | 6/1998 |
| EP | 0 864 337 | 9/1998 |
| EP | 0 776 595 | 12/1998 |
| EP | 1 069 809 | 1/2001 |
| EP | 1 153 398 | 4/2001 |
| EP | 1 294 445 | 3/2003 |
| EP | 1 348 465 | 10/2003 |
| EP | 1 358 908 | 11/2003 |
| EP | 1 371 390 | 12/2003 |
| EP | 1 402 923 | 3/2004 |
| EP | 1 430 932 | 6/2004 |
| EP | 1 454 653 | 9/2004 |
| EP | 1 454 654 | 9/2004 |
| EP | 1 454 655 | 9/2004 |
| EP | 1 454 656 | 9/2004 |
| EP | 1 454 657 | 9/2004 |
| EP | 1 477 206 | 11/2004 |
| EP | 1 738 798 | 1/2007 |
| EP | 1 826 778 | 8/2007 |
| EP | 1 949 404 | 7/2008 |
| EP | 2183753 | 7/2008 |
| EP | 1949404 | 6/2009 |
| EP | 2394498 | 2/2010 |
| EP | 2232961 | 9/2010 |
| EP | 2232962 | 9/2010 |
| EP | 2227295 | 5/2011 |
| EP | 1 605 742 | 6/2011 |
| EP | 2363170 | 9/2011 |
| EP | 2363171 | 9/2011 |
| EP | 1826778 | 5/2014 |
| EP | 2814304 | 12/2014 |
| EP | 2900324 | 8/2015 |
| EP | 2900325 | 8/2015 |
| EP | 2900326 | 8/2015 |
| FR | 2 560 421 | 8/1985 |
| FR | 2911843 | 8/2008 |
| GB | 0 957 342 | 5/1964 |
| GB | 1360085 | 7/1974 |
| GB | 1485329 | 9/1977 |
| GB | 2 015 821 | 9/1979 |
| GB | 1583400 | 1/1981 |
| GB | 2 361 523 | 10/2001 |
| JP | 43-23267 | 10/1968 |
| JP | U48-108098 | 12/1973 |
| JP | 57-162527 | 10/1982 |
| JP | 58-141000 | 8/1983 |
| JP | 61-80800 | 4/1986 |
| JP | 61-225798 | 10/1986 |
| JP | 62-150804 | 7/1987 |
| JP | 62-186500 | 8/1987 |
| JP | 10-071213 | 3/1988 |
| JP | 63-149344 | 6/1988 |
| JP | 63-218200 | 9/1988 |
| JP | 63-226899 | 9/1988 |
| JP | 64-89621 | 4/1989 |
| JP | 01-276797 | 11/1989 |
| JP | 01-302700 | 12/1989 |
| JP | 4-94198 | 3/1992 |
| JP | 04-128717 | 4/1992 |
| JP | 04-129768 | 4/1992 |
| JP | 04-273409 | 9/1992 |
| JP | 04-337300 | 11/1992 |
| JP | 05-341352 | 12/1993 |
| JP | 06-233831 | 8/1994 |
| JP | 06-036893 | 10/1994 |
| JP | 07-260939 | 10/1995 |
| JP | 07-263196 | 10/1995 |
| JP | 08-173890 | 7/1996 |
| JP | 08-264298 | 10/1996 |
| JP | 09-162585 | 6/1997 |
| JP | 11-47287 | 2/1999 |
| JP | 11-102800 | 4/1999 |
| JP | 11-243295 | 9/1999 |
| JP | 2000-243309 | 9/2000 |
| JP | 2000-294399 | 10/2000 |
| JP | 2001-6900 | 1/2001 |
| JP | 2001-009050 | 1/2001 |
| JP | 2001-129103 | 5/2001 |
| JP | 2001-346893 | 12/2001 |
| JP | 2002-164686 | 6/2002 |
| JP | A2003-504628 | 2/2003 |
| JP | 2003-517755 | 5/2003 |

(56) References Cited

FOREIGN PATENT DOCUMENTS

| | | |
|---|---|---|
| JP | 2004-031115 A | 1/2004 |
| JP | 2005-526578 | 9/2005 |
| JP | 2006-032282 | 2/2006 |
| JP | 2007-319439 | 12/2007 |
| JP | 2008-012121 | 1/2008 |
| JP | 05-046928 | 3/2008 |
| JP | 2008-507826 | 3/2008 |
| JP | 2008-089341 | 4/2008 |
| JP | 2009-515671 | 4/2009 |
| JP | 2009-516905 | 4/2009 |
| JP | 2010-204020 | 9/2010 |
| JP | 2010-536130 | 11/2010 |
| JP | 2011-505191 | 2/2011 |
| JP | 2011-505670 | 2/2011 |
| JP | 2011-507151 | 3/2011 |
| JP | 2011-521425 | 7/2011 |
| JP | 2011-224342 | 11/2011 |
| SU | 300137 | 11/1969 |
| SU | 569 635 | 8/1977 |
| TW | 200930160 | 7/2009 |
| TW | 200934682 | 8/2009 |
| TW | 200939908 | 9/2009 |
| TW | 200940120 | 10/2009 |
| TW | 201422278 | 6/2014 |
| TW | 201422279 | 6/2014 |
| TW | 201424466 | 6/2014 |
| TW | 201429514 | 8/2014 |
| TW | 201433331 | 9/2014 |
| TW | 201434508 | 9/2014 |
| TW | 201438787 | 10/2014 |
| WO | WO 86/07229 | 12/1986 |
| WO | WO 90/12413 | 10/1990 |
| WO | WO 92/03028 | 2/1992 |
| WO | WO 93/02536 | 2/1993 |
| WO | WO 98/17342 | 4/1998 |
| WO | WO 99/39385 | 8/1999 |
| WO | WO 00/40064 | 7/2000 |
| WO | WO 00/49624 | 8/2000 |
| WO | WO 01/26230 | 4/2001 |
| WO | WO 01/26569 | 4/2001 |
| WO | WO 02/07817 | 1/2002 |
| WO | WO 03/039212 | 5/2003 |
| WO | WO 03/092812 | 11/2003 |
| WO | WO 2004/026401 | 4/2004 |
| WO | WO 2004/101070 | 11/2004 |
| WO | WO 2006-012467 | 2/2006 |
| WO | WO2007/061937 | 5/2007 |
| WO | WO 2007/061937 | 5/2007 |
| WO | WO 2007/084701 | 7/2007 |
| WO | WO 2007/130164 | 11/2007 |
| WO | WO 2007/145906 | 12/2007 |
| WO | WO 2008/030911 | 3/2008 |
| WO | WO 2008/081480 | 10/2008 |
| WO | WO 2009/048745 | 4/2009 |
| WO | WO 2009/070173 | 6/2009 |
| WO | WO 2009/070588 | 6/2009 |
| WO | WO 2009/073480 | 6/2009 |
| WO | WO 2009/080080 | 7/2009 |
| WO | WO 2010/089574 | 8/2010 |
| WO | WO 2012/044957 | 4/2012 |
| WO | WO 2013/079311 | 6/2013 |
| WO | WO 2013/098089 | 7/2013 |
| WO | WO 2013/142409 | 9/2013 |
| WO | WO 2014/018706 | 1/2014 |
| WO | WO 2014/018876 | 1/2014 |
| WO | WO 2014/052708 | 4/2014 |
| WO | WO 2014/052716 | 4/2014 |
| WO | WO2014/052718 | 4/2014 |
| WO | WO 2014/052719 | 4/2014 |
| WO | WO 2014/052722 | 4/2014 |
| WO | WO 2014/052734 | 4/2014 |

OTHER PUBLICATIONS

International Search Report and Written Opinion mailed Feb. 12, 2014 from counterpart PCT application No. PCT/US2013/062137 (13 pages).

Invitation to pay additional fees and, where applicable, protest fees mailed Nov. 28, 2013 from counterpart PCT application No. PCT/US2013/062137 (6 pages) (includes attached search report).

International Preliminary Report on Patentability issued in PCT application PCT/US2013/062137 on Apr. 9, 2015 (9 pages).

"Beam Delivery and Properties," *Journal of the ICRU*, 2007, 7(2):20 pages.

"510(k) Summary Ion Beam Applications S.A.", FDA, Jul. 12, 2001, 5 pages.

"510(k) Summary Optivus Proton Beam Therapy System", Jul. 21, 2000, 5 pages.

"An Accelerated Collaboration Meets with Beaming Success," Lawrence Livermore National Laboratory, Apr. 12, 2006, S&TR, Livermore, California, pp. 1-3, http://www.llnl.gov/str/April06/Caporaso.html.

"CPAC Highlights Its Proton Therapy Program at ESTRO Annual Meeting", TomoTherapy Incorporated, Sep. 18, 2008, Madison, Wisconsin, pp. 1-2.

"Indiana's mega-million proton therapy cancer center welcomes its first patients" [online] Press release, Health & Medicine Week, 2004, retrieved from NewsRx.com, Mar. 1, 2004, pp. 119-120.

"LLNL, UC Davis Team Up to Fight Cancer,"Lawrence Livermore National Laboratory, Apr. 28, 2006, SF-06-04-02, Livermore, California, pp. 1-4.

"Patent Assignee Search 'Paul Scherrer Institute," Library Services at Fish & Richardson P.C., Mar. 20, 2007, 40 pages.

"Patent Prior Art Search for 'Proton Therapy System'," Library Services at Fish & Richardson P.C., Mar. 20, 2007, 46 pages.

"Superconducting Cyclotron Contract" awarded by Paul Scherrer Institute (PSI), Villigen, Switzerland, http://www.accel.de/News/superconducting_cyclotron_contract.htm, Jan. 2009, 1 page.

"The Davis 76-Inch Isochronous Cyclotron", Beam On: Crocker Nuclear Laboratory, University of California, 2009, 1 page.

"The K100 Neutron-therapy Cyclotron," National Superconducting Cyclotron Laboratory at Michigan State University (NSCL), retrieved from: http://www.nscl.msu.edu/tech/accelerators/k100, Feb. 2005, 1 page.

"The K250 Proton therapy Cyclotron," National Superconducting Cyclotron Laboratory at Michigan State University (NSCL), retrieved from: http://www.nscl.msu.edu/tech/accelerators/k250.html, Feb. 2005, 2 pages.

"The K250 Proton-therapy Cyclotron Photo Illustration," National Superconducting Cyclotron Laboratory at Michigan State University (NSCl), retrieved from: http://www.nscl.msu.edu/media/image/experimental-equipment-technology/250.html, Feb. 2005, 1 page.

$18^{th}$ Japan Conference on Radiation and Radioisotopes [Japanese], Nov. 25-27, 1987, 9 pages.

Abrosimov et al., "1000MeV Proton Beam Therapy facility at Petersburg Nuclear Physics Institute Synchrocyclotron," Medical Radiology (Moscow) 32, 10 (1987) revised in Journal of Physics, Conference Series 41, 2006, pp. 424-432, Institute of Physics Publishing Limited.

Abrosimov et al., "Neutron Time-of-flight Spectrometer Gneis at the Gatchina 1 GeV Protron Syncrhocyclotron", Mar. 9, 1985 and revised form Jul. 31, 1985, Lemingrad Nuclear Physics Institute, Gatchina, 188350, USSR (15 pages).

Adachi et al., "A 150MeV FFAG Synchrotron with "Return-Yoke Free" Magent," *Proceedings of the 2001 Particle Accelerator Conference*, Chicago, 2001, 3 pages.

Ageyev et al., "The IHEP Accelerating and Storage Complex (UNK) Status Report," *11th International Conference on High-Energy Accelerators*, 1980, pp. 60-70.

Agosteo et al., "Maze Design of a gantry room for proton therapy,"*Nuclear Instruments & Methods in Physics Research*, 1996, Section A, 382, pp. 573-582.

Alexeev et al., "R4 Design of Superconducting Magents for Proton Synchrotrons," *Proceedings of the Fifth International Cryogenic Engineering Conference*, 1974, pp. 531-533.

(56) References Cited

OTHER PUBLICATIONS

Allardyce et al., "Performance and Prospects of the Reconstructed CERN 600 MeV Synchrocyclotron," *IEEE Transactions on Nuclear Science USA*, Jun. 1977, ns-24:(3)1631-1633.
Alonso, "Magnetically Scanned Ion Beams for Radiation Therapy," Accelerator & Fusion Research Division, Lawrence Berkeley Laboratory, Berkeley, CA, Oct. 1988, 13 pages.
Amaldi et al., "The Italian project for a hadrontherapy centre" *Nuclear Instruments and Methods in Physics Research A*, 1995, 360, pp. 297-301.
Amaldi, "Overview of the world landscape of Hadrontherapy and the projects of the TERA foundation," Physica Medica, An International journal Devoted to the Applications of Physics to Medicine and Biology, Jul. 1998, vol. XIV, Supplement 1, 6th Workshop on Heavy Charged Particles in Biology and Medicine, Instituto Scientific Europeo (ISE), Sep. 29-Oct. 1, 1977, Baveno, pp. 76-85.
Anferov et al., "Status of the Midwest Proton Radiotherapy Institute," Proceedings of the 2003 Particle Accelerator Conference, 2003, pp. 699-701.
Anferov et al., "The Indiana University Midwest Proton Radiation Institute," Proceedings of the 2001 Particle Accelerator Conference, 2001, Chicago, pp. 645-647.
Appun, "Various problems of magnet fabrication for high-energy accelerators," *Journal for All Engineers Interested in the Nuclear Field*, 1967, pp. 10-16 (1967) [Lang.: German], English bibliographic information (http://www.osti.gov/energycitations/product.biblio.jsp?osti_id=4442292).
Arduini et al. "Physical specifications of clinical proton beams from a synchrotron," *Med. Phys*, Jun. 1996, 23 (6): 939-951.
Badano et al., "Proton-Ion Medical Machine Study (PIMMS) Part I," PIMMS, Jan. 1999, 238 pages.
Beeckman et al., "Preliminary design of a reduced cost proton therapy facility using a compact, high field isochronous cyclotron," *Nuclear Instruments and Methods in Physics Research B56/57*, 1991, pp. 1201-1204.
Bellomo et al., "The Superconducting Cyclotron Program at Michigan State University," *Bulletin of the American Physical Society*, Sep. 1980, 25(7):767.
Benedikt and Carli, "Matching to Gantries for Medical Synchrotrons" *IEEE Proceedings of the 1997 Particle Accelerator Conference*, 1997, pp. 1379-1381.
Bieth et al., "A Very Compact Protontherapy Facility Based on an Extensive Use of High Temperature Superconductors (HTS)" *Cyclotrons and their Applications 1998*, Proceedings of the Fifteenth International Conference on Cyclotrons and their Applications, Caen, Jun. 14-19, 1998, pp. 669-672.
Bigham, "Magnetic Trim Rods for Superconducting Cyclotrons," Nuclear Instruments and Methods (North-Holland Publishing Co.), 1975, 141:223-228.
Bimbot, "First Studies of the External Beam from the Orsay S.C. 200 MeV," Institut de Physique Nucleaire, BP 1, Orsay, France, *IEEE*, 1979, pp. 1923-1926.
Blackmore et al., "Operation of the Triumf Proton Therapy Facility," *IEEE Proceedings of the 1997 Particle Accelerator Conference*, May 12-16, 1997 3:3831-3833.
Bloch, "The Midwest Proton Therapy Center," Application of Accelerators in Research and Industry, Proceedings of the Fourteenth Int'l. Conf., Part Two, Nov. 1996, pp. 1253-1255.
Blosser et al., "Problems and Accomplishments of Superconducting Cyclotrons," Proceedings of the 14th International Conference, Cyclotrons and Their Applications, Oct. 1995, pp. 674-684.
Blosser et al., "Superconducting Cyclotrons", Seventh International Conference on Cyclotrons and their Applications, Aug. 19-22, 1975, pp. 584-594.
Blosser et al., "Progress toward an experiment to study the effect of RF grounding in an internal ion source on axial oscillations of the beam in a cyclotron," National Superconducting Cyclotron Laboratory, Michigan State University, Report MSUCL-760, CP600, Cyclotrons and their Applications 2011, Sixteenth International Conference, 2001, pp. 274-276.
Blosser et al., "A Compact Superconducting Cyclotron for the Production of High Intensity Protons," Proceedings of the 1997 Particle Accelerator Conference, May 12-16, 1997, 1:1054-1056.
Blosser et al., "Advances in Superconducting Cyclotrons at Michigan State University," Proceedings of the 11th International Conference on Cyclotrons and their Applications, Oct. 1986, pp. 157-167, Tokyo.
Blosser et al., "Characteristics of a 400 (Q2/A) MeV Super-Conducting Heavy-Ion Cyclotron," Bulletin of the American Physical Society, Oct. 1974, p. 1026.
Blosser et al., "Medical Accelerator Projects at Michigan State Univ." IEEE Proceedings of the 1989 Particle Accelerator Conference, Mar. 20-23, 1989, 2:742-746.
Blosser et al., "Superconducting Cyclotron for Medical Application", *IEEE Transactions on Magnetics*, Mar. 1989, 25(2): 1746-1754.
Blosser, "Application of Superconductivity in Cyclotron Construction," *Ninth International Conference on Cyclotrons and their Applications*, Sep. 1981, pp. 147-157.
Blosser, "Applications of Superconducting Cyclotrons," Twelfth International Conference on Cyclotrons and Their Applications, May 8-12, 1989, pp. 137-144.
Blosser, "Future Cyclotrons," AIP, *The Sixth International Cyclotron Conference*, 1972, pp. 16-32.
Blosser, "Medical Cyclotrons," *Physics Today*, Special Issue Physical Review Centenary, Oct. 1993, pp. 70-73.
Blosser, "Preliminary Design Study Exploring Building Features Required for a Proton Therapy Facility for the Ontario Cancer Institute", Mar. 1991, MSUCL-760a, 53 pages.
Blosser, "Progress on the Coupled Superconducting Cyclotron Project," *Bulletin of the American Physical Society*, Apr. 1981, 26(4):558.
Blosser, "Synchrocyclotron Improvement Programs," *IEEE Transactions on Nuclear Science USA*, Jun. 1969, 16(3):Part I, pp. 405-414.
Blosser, "The Michigan State University Superconducting Cyclotron Program," *Nuclear Science*, Apr. 1979, NS-26(2):2040-2047.
Blosser, H., Present and Future Superconducting Cyclotrons, *Bulletin of the American Physical Society*, Feb. 1987, 32(2):171 Particle Accelerator Conference, Washington, D.C.
Blosser, H.G., "Superconducting Cyclotrons at Michigan State University", Nuclear Instruments & Methods in Physics Research, 1987,vol. B 24/25, part II, pp. 752-756.
Botha et al., "A New Multidisciplinary Separated-Sector Cyclotron Facility," *IEEE Transactions on Nuclear Science*, 1977, NS-24(3):1118-1120.
Chichili et al., "Fabrication of Nb3Sn Shell-Type Coils with Pre-Preg Ceramic Insulation," American Institute of Physics Conference Proceedings, AIP USA, No. 711, (XP-002436709, ISSN: 0094-243X), 2004, pp. 450-457.
Chong et al., Radiology Clinic North American 7, 3319, 1969, 27 pages.
Chu et al., "Performance Specifications for Proton Medical Facility," Lawrence Berkeley Laboratory, University of California, Mar. 1993, 128 pages.
Chu et al., "Instrumentation for Treatment of Cancer Using Proton and Light-ion Beams," Review of Scientific Instruments, Aug. 1993, 64 (8):2055-2122.
Chu, "Instrumentation in Medical Systems," Accelerator and Fusion Research Division, Lawrence Berkeley Laboratory, University of California, Berkeley, CA, May 1995, 9 pages.
Cole et al., "Design and Application of a Proton Therapy Accelerator," Fermi National Accelerator Laboratory, *IEEE*, 1985, 5 pages.
Collins, et al., "The Indiana University Proton Therapy System," Proceedings of EPAC 2006, Edinburgh, Scotland, 2006, 3 pages.
Conradi et al., "Proposed New Facilities for Proton Therapy at iThemba Labs," *Proceedings of EPAC*, 2002, pp. 560-562.
C/E Source of Ions for Use in Sychro-Cyclotrons Search, Jan. 31, 2005, 9 pages.

(56) References Cited

OTHER PUBLICATIONS

Source Search "Cites of U.S. and Foreign Patents/Published applications in the name of Mitsubishi Denki Kabushiki Kaisha and Containing the Keywords (Proton and Synchrocyclotron)," Jan. 2005, 8 pages.
Cosgrove et al., "Microdosimetric Studies on the Orsay Proton Synchrocyclotron at 73 and 200 MeV," *Radiation Protection Dosimetry*, 1997, 70(1-4):493-496.
Coupland, "High-field (5 T) pulsed superconducting dipole magnet," *Proceedings of the Institution of Electrical Engineers*, Jul. 1974, 121(7):771-778.
Coutrakon et al. "Proton Synchrotrons for Cancer Therapy," Application of Accelerators in Research and Industry—Sixteenth International Conf., American Institute of Physics, Nov. 1-5, 2000, vol. 576, pp. 861-864.
Coutrakon et al., "A prototype beam delivery system for the proton medical accelerator at Loma Linda," *Medical Physics*, Nov./Dec. 1991, 18(6):1093-1099.
Cuttone, "Applications of a Particle Accelerators in Medical Physics," Istituto Nazionale di Fisica Nucleare-Laboratori Nazionali del Sud, V.S. Sofia, 44 Cantania, Italy, Jan. 2010, 17 pages.
Dahl P, "Superconducting Magnet System," American Institute of Physics, AIP Conference Proceedings, 1987-1988, 2: 1329-1376.
Dialog Search, Jan. 31, 2005, 17 pages.
Dugan et al., "Tevatron Status" IEEE, Particle Accelerator Conference, Accelerator Science & Technology, 1989, pp. 426-430.
Eickhoff et al., "The Proposed Accelerator Facility for Light Ion Cancer Therapy in Heidelberg," Proceedings of the 1999 Particle Accelerator Conference, New York, 1999, pp. 2513-2515.
Enchevich et al., "Minimizing Phase Losses in the 680 MeV Synchrocyclotron by Correcting the Accelerating Voltage Amplitude," *Atomnaya Energiya*, 1969, 26:(3):315-316.
Endo et al., "Compact Proton and Carbon Ion Synchrotrons for Radiation Therapy," Proceedings of EPAC 2002, Paris France, 2002, pp. 2733-2735.
Flanz et al., "Treating Patients with the NPTC Accelerator Based Proton Treatment Facility," Proceedings of the 2003 Particle Accelerator Conference, 2003, pp. 690-693.
Flanz et al., "Large Medical Gantries," Particle Accelerator Conference, Massachusetts General Hospital, 1995, pp. 1-5.
Flanz et al., "Operation of a Cyclotron Based Proton Therapy Facility", Massachusetts General Hospital, Boston, MA 02114, pp. 1-4, retrieved from Internet in 2009.
Flanz et al., "The Northeast Proton Therapy Center at Massachusetts General Hospital," Fifth Workshop on Heavy Charge Particles in Biology and Medicine, GSI, Darmstadt, Aug. 1995, 11 pages.
Flood and Frazier, "The Wide-Band Driven RF System for the Berkeley 88-Inch Cyclotron," American Institute of Physics, Conference Proceedings., No. 9, 1972, 459-466.
Foster and Kashikhin, "Superconducting Superferric Dipole Magent with Cold Iron Core for the VLHC," *IEEE Transactions on Applied Superconductivity*, Mar. 2002, 12(1):111-115.
Friesel et al., "Design and Construction Progress on the IUCF Midwest Proton Radiation Institute," Proceedings of EPAC 2002, 2002, pp. 2736-2738.
Fukumoto et al., "A Proton Therapy Facility Plan" Cyclotrons and their Applications, Proceedings of the 13th International Conference, Vancouver, Canada, Jul. 6-10, 1992, pp. 258-261.
Fukumoto, "Cyclotron Versus Synchrotron for Proton Beam Therapy," KEK Prepr., No. 95-122, Oct. 1995, pp. 533-536.
Goto et al., "Progress on the Sector Magnets for the Riken SRC," American Institute of Physics, CP600, Cyclotrons and Their Applications 2001, Sixteenth International Conference, 2001, pp. 319-323.
Graffman et al., "Design Studies for a 200 MeV Proton Clinic for Radiotherapy," AIP Conference Proceedings: Cyclotrons—1972, 1972, No. 9, pp. 603-615.
Graffman et al., *Acta Radiol. Therapy Phys. Biol.* 1970, 9, 1 (1970).
Graffman, et al "Proton radiotherapy with the Uppsala cyclotron. Experience and plans" *Strahlentherapie*, 1985, 161(12):764-770.

Hede, "Research Groups Promoting Proton Therapy "Lite,"" Journal of the National Cancer Institute, Dec. 6, 2006, 98(23):1682-1684.
Heinz, "Superconducting Pulsed Magnetic Systems for High-Energy Synchrotrons," *Proceedings of the Fourth International Cryogenic Engineering Conference*, May 24-26, 1972, pp. 55-63.
Hentschel et al., "Plans for the German National Neutron Therapy Centre with a Hospital-Based 70 MeV Proton Cyclotron at University Hospital Essen/Germany," Cyclotrons and their Applications, Proceedings of the Fifteenth International Conference on Cyclotrons and their Applications, Caen, Franco, Jun. 14-19, 1998, pp. 21-23.
Hepburn et al., "Superconducting Cyclotron Neutron Source for Therapy," *International Journal of Radiation Oncology Biology Physics*, vol. 3 complete, 1977, pp. 387-391.
Hirabayashi, "Development of Superconducting Magnets for Beam Lines and Accelerator at KEK," *IEEE Transaction on Magnetics*, Jan. 1981, Mag-17(1):728-731.
Ishibashi and McInturff, "Winding Design Study of Superconducting 10 T Dipoles for a Synchrotron," *IEEE Transactions on Magnetics*, May 1983, Mag-19(3):1364-1367.
Ishibashi and McInturff, "Stress Analysis of Superconducting 10T Magnets for Synchrotron," Proceedings of the Ninth International Cryogenic Engineering Conference, May 11-14, 1982, pp. 513-516.
Jahnke et al., "First Superconducting Prototype Magnets for a Compact Synchrotron Radiation Source in Operation," *IEEE Transactions on Magnetics*, Mar. 1988, 24(2):1230-1232.
Jones and Dershem, "Synchrotron Radiation from Proton in a 20 TEV, 10 TESLA Superconducting Super Collide,r" *Proceedings of the 12th International Conference on High-Energy Accelerator*, Aug. 11-16, 1983, pp. 138-140.
Jones and Mills, "The South African National Accelerator Centre: Particle Therapy and Isotope Production Programmes," *Radiation Physics and Chemistry*, Apr.-Jun. 1998, 51(4-6):571-578.
Jones et al., "Status Report of the NAC Particle Therapy Programme," *Stralentherapie und Onkologie*, vol. 175, Suppl. II, Jun. 1999, pp. 30-32.
Jones, "Progress with the 200 MeV Cyclotron Facility at the National Accelerator Centre," Commission of the European Communities Radiation Protection Proceedings, Fifth Symposium on Neutron Dosimetry, Sep. 17-21, 1984, vol. II, pp. 989-998.
Jones, "Present Status and Future Trends of Heavy Particle Radiotherapy," Cyclotrons and their Applications 1998, Proceedings of the Fifteenth International Conference on Cyclotrons and their Applications, Jun. 14-19, 1998, pp. 13-20.
Jongen et al., "Development of a Low-cost Compact Cyclotron System for Proton Therapy," *National Institute of Radiol. Sci*,1991, No. 81, pp. 189-200.
Jongen et al., "Progress report on the IBA-SHI small cyclotron for cancer therapy" *Nuclear Instruments and Methods in Physics Research*, Section B, vol. 79, issue 1-4, 1993, pp. 885-889.
Jongen et al., "The proton therapy system for the NPTC: Equipment Description and progress report," *Nuclear Instruments and methods in physics research*, 1996, Section B, 113(1): 522-525.
Jongen et al., "The proton therapy system for MGH's NPTC: equipment description and progress report," *Bulletin du Cancer/Radiotherapie, Proceedings of the meeting of the European Heavy Particle Therapy Group*, 1996, 83(Suppl. 1):219-222.
Kanai et al., "Three-dimensional Beam Scanning for Proton Therapy," Nuclear Instruments and Methods in Physic Research, Sep. 1, 1983, The Netherlands, 214(23):491-496.
Karlin et al., "Medical Radiology" (Moscow), 1983, 28, 13.
Karlin et al., "The State and Prospects in the Development of the Medical Proton Tract on the Synchrocyclotron in Gatchina," *Med. Radiol.*, Moscow, 28(3):28-32 (Mar. 1983)(German with English Abstract on end of p. 32).
Kats and Druzhinin, "Comparison of Methods for Irradiation Prone Patients," *Atomic Energy*, Feb. 2003, 94(2):120-123.
Kats and Onosovskii, "A Simple, Compact, Flat System for the Irradiation of a Lying Patient with a Proton Beam from Different Directions," *Instruments and Experimental Techniques*, 1996, 39(1): 132-134.

(56) References Cited

OTHER PUBLICATIONS

Kats and Onosovskii, "A Planar Magnetooptical System for the Irradiation of a Lying Patient with a Proton Beam from Various Directions," *Instruments and Experimental Techniques*, 1996, 39(1):127-131.
Khoroshkov et al.,"Moscow Hospital-Based Proton Therapy Facility Design," *Am. Journal Clinical Oncology: CCT*, Apr. 1994, 17(2):109-114.
Kim and Blosser, "Optimized Magnet for a 250 MeV Proton Radiotherapy Cyclotron," Cyclotrons and Their Applications 2001, May 2001, *Sixteenth International Conference*, pp. 345-347.
Kim and Yun, "A Light-Ion Superconducting Cyclotron System for Multi-Disciplinary Users," *Journal of the Korean Physical Society*, Sep. 2003, 43(3):325-331.
Kim et al., "Construction of 8T Magnet Test Stand for Cyclotron Studies," *IEEE Transactions on Applied Superconductivity*, Mar. 1993, 3(1):266-268.
Kim et al., "Design Study of a Superconducting Cyclotron for Heavy Ion Therapy," *Cyclotrons and Their Applications 2001, Sixteenth International Conference*, May 13-17, 2001, pp. 324-326.
Kim et al., "Trim Coil System for the Riken Cyclotron Ring Cyclotron," *Proceedings of the 1997 Particle Accelerator Conference, IEEE*, Dec. 1981, vol. 3, pp. 214-235 or 3422-3424, 1998.
Kim, "An Eight Tesla Superconducting Magnet for Cyclotron Studies," Ph.D. Dissertation, Michigan State University, Department of Physics and Astronomy, 1994, 138 pages.
Kimstrand, "Beam Modelling for Treatment Planning of Scanned Proton Beams," Digital Comprehensive Summaries of Uppsala dissertations from the Faculty of Medicine 330, Uppsala Universitet, 2008, 58 pages.
Kishida and Yano, "Beam Transport System for the RIKEN SSC (II)," *Scientific Papers of the Institute of Physical and Chemical Research*, Dec. 1981, 75(4):214-235.
Koehler et al., "Range Modulators for Protons and Heavy Ions," *Nuclear Instruments and Methods*, 1975, vol. 131, pp. 437-440.
Koto and Tsujii, "Future of Particle Therapy," Japanese *Journal of Cancer Clinics*, 2001, 47(1):95-98 [Lang.: Japanese], English abstract (http://sciencelinksjp/j-east/article/200206/000020020601A0511453.php).
Kraft et al., "Hadrontherapy in Oncology," U. Amaldi and Larrsson, editors Elsevier Science, 1994, 390 pages.
Krevet et al., "Design of a Strongly Curved Superconducting Bending Magnet for a Compact Synchrotron Light Source," *Advances in Cryogenic Engineering*, 1988, vol. 33, pp. 25-32.
Laisne et al., "The Orsay 200 MeV Synchrocyclotron," *IEEE Transactions on Nuclear Science*, Apr. 1979, NS-26(2):1919-1922.
Larsson et al., *Nature*, 1958, 182:1222.
Larsson, "Biomedical Program for the Converted 200-MeV Synchrocyclotron at the Gustaf Werner Institute," *Radiation Research*, 1985, 104:S310-S318.
Lawrence et al., "Heavy particles in acromegaly and Cushing's Disease," in Endocrine and Norendocrine Hormone Producing Tumors (Year Book Medical Chicago, 1973, pp. 29-61.
Lawrence et al., "Successful Treatment of Acromegaly: Metabolic and Clinical Studies in 145 Patients," *The Journal of Clinical Endrocrinology and Metabolism*, Aug. 1970, 31(2), 21 pages.
Lawrence et al., "Treatment of Pituitary Tumors," (Excerpta medica, Amsterdam/American Elsevier, New York, 1973, pp. 253-262.
Lawrence, *Cancer*, 1957, 10:795.
Lecroy et al., "Viewing Probe for High Voltage Pulses," *Review of Scientific Instruments USA*, Dec. 1960, 31(12):1354.
Lin et al., "Principles and 10 Year Experience of the Beam Monitor System at the PSI Scanned Proton Therapy Facility", Center for Proton Radiation Therapy, Paul Scherrer Institute, CH-5232, Villigen PSI, Switzerland, 2007, 21 pages.
Linfoot et al., "Acromegaly," in Hormonal Proteins and Peptides, edited by C.H. Li, 1975, pp. 191-246.
Literature Author and Keyword Search, Feb. 14, 2005, 44 pages.
Literature Keyword Search, Jan. 24, 2005, 98 pages.

Literature Search and Keyword Search for Synchrocyclotron, Jan. 25, 2005, 68 pages.
Literature Search by Company Name/Component Source, Jan. 24, 2005, 111 pages.
Literature Search, Jan. 26, 2005, 37 pages.
Livingston et al., "A capillary ion source for the cyclotron," *Review Science Instruments*, Feb. 1939, 10:63.
Mandrillon, "High Energy Medical Accelerators," *EPAC 90, 2nd European Particle Accelerator Conference*, Jun. 12-16, 1990, 2:54-58.
Marchand et at, "IBA Proton Pencil Beam Scanning: an Innovative Solution for Cancer Treatment," Proceedings of EPAC 2000, Vienna, Austria, 3 pages.
Marti et al., "High Intensity Operation of a Superconducting Cyclotron," *Proceedings of the 14the International Conference, Cyclotrons and Their Applications*, Oct. 1995, pp. 45-48 (Oct. 1995).
Martin, "Operational Experience with Superconducting Synchrotron Magnets" *Proceedings of the 1987 IEEE Particle Accelerator Conference*, Mar. 16-19, 1987, vol. 3 of 3:1379-1382.
Meote et al., "ETOILE Hadrontherapy Project, Review of Design Studies" *Proceedings of EPAC 2002*, 2002, pp. 2745-2747.
Miyamoto et al., "Development of the Proton Therapy System," *The Hitachi Hyoron*, 79(10):775-779 (1997) [Lang: Japanese], English abstract (http://www.hitachi.com/rev/1998/revfeb98/rev4706.htm).
Montelius et al., "The Narrow Proton Beam Therapy Unit at the Svedberg Laboratory in Uppsala," *ACTA Oncologica*, 1991, 30:739-745.
Moser et al., "Nonlinear Beam Optics with Real Fields in Compact Storage Rings," Nuclear Instruments & Methods in Physics Research/Section B, B30, Feb. 1988, No. 1, pp. 105-109.
Moyers et al., "A Continuously Variable Thickness Scatterer for Proton Beams Using Self-compensating Dual Linear Wedges" Lorna Linda University Medical Center, Dept. of Radiation Medicine, Lorna Linda, CA, Nov. 2, 1992, 21 pages.
National Cancer Institute Funding (Senate—Sep. 21, 1992) (www.thomas.loc.gov/cgi-bin/query/z?r102:S21SE2-712 (2 pages).
Nicholson, "Applications of Proton Beam Therapy," *Journal of the American Society of Radiologic Technologists*, May/Jun. 1996, 67(5): 439-441.
Nolen et al., "The Integrated Cryogenic—Superconducting Beam Transport System Planned for MSU," *Proceedings of the 12th International Conference on High-Energy Accelerators*, Aug. 1983, pp. 549-551.
Norimine et al., "A Design of a Rotating Gantry with Easy Steering for Proton Therapy," *Proceedings of EPAC 2002*, 2002, pp. 2751-2753.
Ogino, Takashi, "Heavy Charged Particle Radiotherapy-Proton Beam", Division of Radiation Oncology, National Cancer Hospital East, Kashiwa, Japan, Dec. 2003, 7 pages.
Okumura et al., "Overview and Future Prospect of Proton Radiotherapy," *Japanese Journal of Cancer Clinics*, 1997, 43(2):209-214 [Lang.: Japanese].
Okumura et al., "Proton Radiotherapy" *Japanese Journal of Cancer and Chemotherapy*, 1993, 10. 20(14):2149-2155 [Lang.: Japanese].
Outstanding from Search Reports, "Accelerator of Polarized Portons at Fermilab," 2005, 20 pages.
Paganetti et al., "Proton Beam Radiotherapy—The State of the Art," Springer Verlag, Heidelberg, ISBN 3-540-00321-5, Oct. 2005,36 pages.
Palmer and Tollestrup, "Superconducting Magnet Technology for Accelerators," *Annual Review of Nuclear and Particle Science*, 1984, vol. 34, pp. 247-284.
Patent Assignee and Keyword Searches for Synchrocyclotron, Jan. 25, 2005, 78 pages.
Pavlovic, "Beam-optics study of the gantry beam delivery system for light-ion cancer therapy," *Nuclear Instruments and Methods in Physics Research*, Section A, Nov. 1997, 399(2):439-454(16).
Pedroni and Enge, "Beam optics design of compact gantry for proton therapy" *Medical & Biological Engineering & Computing*, May 1995, 33(3):271-277.
Pedroni and Jermann, "SGSMP: Bulletin Mar. 2002 Proscan Project, Progress Report on the PROSCAN Project of PSI" [online] retrieved from www.sgsmp.ch/protA23.htm, Mar. 2002, 5 pages.

(56) References Cited

OTHER PUBLICATIONS

Pedroni et al., "A Novel Gantry for Proton Therapy at the Paul Scherrer Institute," *Cycloctrons and Their Applications 2001: Sixteenth International Conference. AIP Conference Proceedings*, 2001, 600:13-17.
Pedroni et al., "The 200-MeV proton therapy project at the Paul Scherrer Institute: Conceptual design and practical realization," *Medical Physics*, Jan. 1995, 22(1):37-53.
Pedroni, "Accelerators for Charged Particle Therapy: Performance Criteria from the User Point of View," *Cyclotrons and their Applications, Proceedings of the 13th International Conference*, Jul. 6-10, 1992, pp. 226-233.
Pedroni, "Latest Developments in Proton Therapy" *Proceedings of EPAC 2000*, pp. 240-244, 2000.
Pedroni, "Status of Proton Therapy: results and future trends," Paul Scherrer Institute, Division of Radiation Medicine, 1994, 5 pages.
Peggs et al., "A Survey of Hadron Therapy Accelerator Technologies," Particle Accelerator Conference, Jun. 25-29, 2007, 7 pages.
Potts et al., "MPWP6-Therapy III: Treatment Aids and Techniques" *Medical Physics*, Sep./Oct. 1988, 15(5):798.
Pourrahimi et al., "Powder Metallurgy Processed Nb3 Sn(Ta) Wire for High Field NMR magnets," *IEEE Transactions on Applied Superconductivity*, Jun. 1995, 5(2):1603-1606.
Prieels et al., "The IBA State-of-the-Art Proton Therapy System, Performances and Recent Results," *Application of Accelerators in Research and industry—Sixteenth Int'l. Conf., American Institute of Physics*, Nov. 1-5, 2000, 576:857-860.
Rabin et al., "Compact Designs for Comprehensive Proton Beam Clinical Facilities," *Nuclear Instruments & Methods in Physics Research*, Apr. 1989, Section B, vol. 40-41, Part II, pp. 1335-1339.
*Research & Development Magazine*, "Proton Therapy Center Nearing Completion," Aug. 1999. 41(9):2 pages. (www.rdmag.com).
Resmini, "Design Characteristics of the K=800 Superconducting Cyclotron at M.S.U.," Cyclotron Laboratory, Michigan State University, East Lansing, Michigan 48824, IEEE Transaction on Nuclear Science, vol. NS-26, No. 2, Apr. 1979, 8 pages.
RetroSearch "Berkeley 88-Inch Cyclotron 'RF' or 'Frequency Control'," Jan. 21, 2005, 36 pages.
RetroSearch "Berkeley 88-Inch Cyclotron," Jan. 24, 2005, 170 pages.
RetroSearch "Bernard Gottschalk, Cyclotron, Beams, Compensated Upstream Modulator, Compensated Scatter," Jan. 21, 2005, 20 pages.
RetroSearch "Cyclotron with 'RF' or 'Frequency Control'," Jan. 21, 2005, 49 pages.
RetroSearch Gottschalk, Bernard, Harvard Cyclotron Wheel, Jan. 21, 2005, 20 pages.
RetroSearch "Loma Linda University Beam Compensation," Jan. 21, 2005, 60 pages.
RetroSearch "Loma Linda University, Beam Compensation Foil Wedge," Jan. 21, 2005, 15 pages.
Revised Patent Keyword Search, Jan. 25, 2005, 88 pages.
Rifuggiato et, al., "Status Report of the LNS Superconducting Cyclotron" *Nukleonika*, 2003, 48: S131-S134, Supplement 2.
Rode, "Tevatron Cryogenic System," *Proceedings of the 12th International Conference on High-energy Accelerators, Fermilab*, Aug. 11-16, 1983, pp. 529-535.
Salzburger et al., "Superconducting Synchrotron Magnets Supraleitende Synchrotronmagnete," Siemens A.G., Erlangen (West Germany). Abteilung Technische Physik, Report No. BMFT-FB-T-75-25, Oct. 1975, p. 147, Journal Announcement: GRAI7619; STAR1415, Subm-Sponsored by Bundesmin. Fuer Forsch. U. Technol. In German; English Summary.
Schillo et al,. "Compact Superconducting 250 MeV Proton Cyclotron for the PSI Proscan Proton Therapy Project," *Cyclotrons and Their Applications 2001, Sixteenth International Conference*, 2001, pp. 37-39.
Schneider et al., "Nevis Synchrocyclotron Conversion Program—RF System," *IEEE Transactions on Nuclear Science USA*, Jun. 1969, ns. 16(3): 430-433.

Schneider et al., "Superconducting Cyclotrons," IEEE Transactions on Magnetics, vol. MAG-11, No. 2, Mar. 1975, New York, pp. 443-446.
Schreuder et al., "The Non-orthogonal Fixed Beam Arrangement for the Second Proton Therapy Facility at the National Accelerator Centre," *Application of Accelerators in Research and Industry, American Institute of Physics, Proceedings of the Fifteenth International Conference*, Nov. 1998, Part Two, pp. 963-966.
Schreuder, "Recent Developments in Superconducting Cyclotrons," *Proceedings of the 1995 Particle Accelerator Conference*, May 1-5, 1995, vol. 1, pp. 317-321.
Schubert and Blosser, "Conceptual Design of a High Field Ultra-Compact Cyclotron for Nuclear Physics Research," *Proceedings of the 1997 Particle Accelerator Conference*, May 12-16, 1997, vol. 1, 3 pages 1060-1062.
Schubert, "Extending the Feasibility Boundary of the Isochronous Cyclotron," Dissertation submitted to Michigan State University, 1997, Abstract http://adsabs.harvard.edu/abs/1998PhDT.......147S.
Shelaev et al., "Design Features of a Model Superconducting Synchrotron of JINR," *Proceedings of the 12th International Conference on High-energy Accelerators*, Aug. 11-16, 1983, pp. 416-418.
Shintomi et. Al, "Technology and Materials for the Superconducting Super Collider (SSC) Project," [Lang.: Japanese], The Iron and Steel Institute of Japan 00211575, 78(8): 1305-1313, 1992, http://ci.nii.ac.jp/naid/110001493249/en/.
Sisterson, "World Wide Proton Therapy Experience in 1997," *The American Insitute of Physics, Applications of Accelerators in Research and Industry, Proceedings of the Fifteenth International Conference*, Part Two, Nov. 1998, pp. 959-962.
Sisterson, "Clinical use of proton and ion beams from a world-wide perspective," *Nuclear Instruments and Methods in Physics Research*, Section B, 1989, 40-41:1350-1353.
Slater et al., "Developing a Clinical Proton Accelerator Facility: Consortium-Assisted Technology Transfer," *Conference Record of the 1991 IEEE Particle Accelerator Conference: Accelerator Science and Technology*, vol. 1, May 6-9, 1991, pp. 532-536.
Slater et al., "Development of a Hospital-Based Proton Beam Treatment Center," *International Journal of Radiation Oncology Biology Physics*, Apr. 1988, 14(4):761-775.
Smith et al., "The Northeast Proton Therapy Center at Massachusetts General Hospital" *Journal of Brachytherapy International*, Jan. 1997, pp. 137-139.
Snyder and Marti, "Central region design studies for a proposed 250 MeV proton cyclotron," *Nuclear Instruments and Methods in Physics Research*, Section A, 1995, vol. 355, pp. 618-623.
Soga, "Progress of Particle Therapy in Japan," Application of Accelerators in Research and Industry, American Institute of Physics, Sixteenth International Conference, Nov. 2000, pp. 869-872.
Spiller et al., "The GSI Synchrotron Facility Proposal for Acceleration of High Intensity Ion and Proton Beams" *Proceedings of the 2003 Particle Accelerator Conference*, May 12-16, 2003, vol. 1, pp. 589-591.
Stanford et al., "Method of Temperature Control in Microwave Ferroelectric Measurements," Sperry Microwave Electronics Company, Clearwater, Florida, Sep. 19, 1960, 1 page.
Tadashi et al., "Large superconducting super collider (SSC) in the planning and materials technology,"78(8):1305-1313, The Iron and Steel Institute of Japan 00211575, Aug. 1992.
Takada, "Conceptual Design of a Proton Rotating Gantry for Cancer Therapy," *Japanese Journal of Medical Physics*, 1995, 15(4):270-284.
Takayama et al., "Compact Cyclotron for Proton Therapy," *Proceedings of the 8th Symposium on Accelerator Science and Technology*, Japan, Nov. 25-27, 1991, pp. 380-382.
Teng, "The Fermilab Tevatron," Coral Gables 1981, Proceedings, Gauge Theories, Massive Neutrinos, and Proton Decay, 1981, pp. 43-62.
The Journal of Practical Pharmacy, 1995, 46(1):97-103 [Japanese].
Tilly, et al., "Development and verification of the pulsed scanned proton beam at The Svedberg Laboratory in Uppsala", Physics in Medicine and Biology, Phys. Med. Biol. 52, pp. 2741-2454, 2007.
Tobias et al., *Cancer Research*,1958, 18, 121 (1958).

(56) References Cited

OTHER PUBLICATIONS

Tom, "The Use of Compact Cyclotrons for Producing Fast Neutrons for Therapy in a Rotatable Isocentric Gantry," *IEEE Transaction on Nuclear Science*, Apr. 1979, 26(2):2294-2298.
Toyoda, "Proton Therapy System", Sumitomo Heavy Industries, Ltd., 2000, 5 pages.
Trinks et. al., "The Tritron: A Superconducting Separated-Orbit Cyclotron," *Nuclear Instruments and Methods in Physics Research*, Section A, 1986, vol. 244, pp. 273-282.
Tsuji, "The Future and Progress of Proton Beam Radiotherapy," *Journal of Japanese Society for Therapeutic Radiology and Oncology*, 1994, 6(2):63-76.
UC Davis School of Medicine, "Unlikely Partners Turn Military Defense into Cancer Offense", Current Issue Summer 2008, Sacramento, California, pp. 1-2.
Umegaki et al., "Development of an Advanced Proton Beam Therapy System for Cancer Treatment" *Hitachi Hyoron*, 2003, 85(9):605-608 [Lang.: Japanese], English abstract, http://www.hitachi.com/ICSFiles/afieldfile/2004/06/01/r2003_04_104.pdf or http://www.hitachi.com/rev/archive/2003/2005649_12606.html (full text) [Hitachi, 52(4), Dec. 2003].
Umezawa et al., "Beam Commissioning of the new Proton Therapy System for University of Tsukuba," *Proceedings of the 2001 Particle Accelerator Conference*, vol. 1, Jun. 18-22, 2001, pp. 648-650.
van Steenbergen, "Superconducting Synchroton Development at BNL," *Proceedings of the 8th International Conference on High-Energy Accelerators CERN 1971*, 1971, pp. 196-198.
van Steenbergen, "The CMS, a Cold Magnet Synchrotron to Upgrade the Proton Energy Range of the BNL Facility," *IEEE Transactions on Nuclear Science*, Jun. 1971, 18(3):694-698.
Vandeplassche et al., "235 MeV Cyclotron for MGH's Northeast Proton Therapy Center (NPTC): Present Status," EPAC 96, *Fifth European Partical Accelerator Conference*, vol. 3, Jun. 10-14, 1996, pp. 2650-2652.
Vorobiev et al., "Concepts of a Compact Achromatic Proton Gantry with a Wide Scanning Field", *Nuclear Instruments and Methods in Physics Research*, Section A., 1998, 406(2):307-310.
Vrenken et al., "A Design of a Compact Gantry for Proton Therapy with 2D-Scanning," *Nuclear Instruments and Methods in Physics Research*, Section A, 1999, 426(2):618-624.
Wikipedia, "Cyclotron" http://en.wikipedia.org/wiki/Cyclotron (originally visited Oct. 6, 2005, revisited Jan. 28, 2009), 7pages.
Wikipedia, "Synchrotron" http://en.wikipedia.org/wiki/Synchrotron (originally visited Oct. 6, 2005, revisited Jan. 28, 2009), 7 pages.
Worldwide Patent Assignee Search, Jan. 24, 2005, 224 pages.
Worldwide Patent Keyword Search, Jan. 24, 2005, 94 pages.
Wu, "Conceptual Design and Orbit Dynamics in a 250 MeV Superconducting Synchrocyclotron," Ph.D. Dissertation, Michigan State University, Department of Physics and Astronomy, 1990, 172 pages.
York et al., "Present Status and Future Possibilities at NSCL-MSU," EPAC 94, Fourth European Particle Accelerator Conference, pp. 554-556, Jun. 1994.
York et al., "The NSCL Coupled Cyclotron Project—Overview and Status,"*Proceedings of the Fifteenth International Conference on Cyclotrons and their Applications*, Jun. 1998, pp. 687-691.
Yudelev et al., "Hospital Based Superconducting Cyclotron for Neutron Therapy: Medical Physics Perspective," *Cyclotrons and their applications 2001, 16th International Conference. American Institute of Physics Conference Proceedings*, vol. 600, May 13-17, 2001, pp. 40-43.
Zherbin et al., "Proton Beam Therapy at the Leningrad Synchrocyclotron (Clinicomethodological Aspects and Therapeutic Results)", Aug. 1987, 32(8):17-22, (German with English abstract on pp. 21-22).
U.S. Appl. No. 61/676,377 filed Jul. 27, 2012, including the electronic file for U.S. Appl. No. 61/676,377 downloaded on Apr. 2, 2014.
U.S. Appl. No. 13/949,459 filed on Jul. 24, 2013, including the electronic file for U.S. Appl. No. 13/949,459 downloaded on Apr. 2, 2014.
U.S. Appl. No. 13/830,792 filed on Mar. 14, 2013, including the electronic file for U.S. Appl. No. 13/830,792 downloaded on Apr. 2, 2014.
European Communication issued in corresponding European application No. 13783422.2 on Jun. 12, 2015 (2 pages).
Response to European Communication issued in corresponding European application No. 13783422.2 on Jun. 12, 2015, filed on Dec. 8, 2015 (19 pages).
Japanese office action issued in corresponding Japanese application 2015-534733 on Mar. 18, 2016 (6 pages). Note: English translation has not been received from Associate.
International Search Report and Written Opinion from PCT application No. PCT/US2013/062119 mailed on Nov. 26, 2013 (9 pages).
International Preliminary Report on Patentability from PCT application No. PCT/US2013/062119 mailed on Apr. 9, 2015 (7 pages).
European Communication issued in corresponding European application No. 13774886.9 on Jun. 12, 2015 (2 pages).
Response to European Communication issued in corresponding European application No. 13774886.9 on Jun. 12, 2015, filed on Jun. 1, 2015 (18 pages).
Japanese office action issued in corresponding Japanese application 2015-534728 on Mar. 28, 2016 (6 pages). Note: English translation has not been received from Associate.
European Communication issued in corresponding European application No. 13779442.6 on Jun. 10, 2015 (2 pages).
Response to European Communication issued in corresponding European application No. 13779442.6 on Jun. 12, 2015, filed on Jun. 1, 2015 (24 pages).
Japanese office action with English translation issued in corresponding Japanese application 2015-534726 on Mar. 7, 2016 (7 pages).
N. F. Verster: "Regenerative Beam Extraction from the 150-MeV Synchrocyclotron at the Laboratoire Curie", Proceedings of Sector-Focused Cyclotrons 1959, 1959, pp. 224-229 (6 pages).
Elo, Don, et al., "Mechanical Design of Regenerative Deflector for the Berkeley 88-Inch Cyclotron", Proceedings of the International Conference on Isochronous Cyclotrons, Gatlinburg, Tennessee, Aug. 1966 (7 pages).
Rainwater, James, "Status of the Nevis Synchrocyclotron Modification", AIP Conference Proceedings No. 9, 1972 (14 pages).
Cohen, R. et al., "Nevis Synchrocyclotron Conversion Project", IEEE Transactions on Nuclear Science, IEEE Service Center, New York, NY, US, vol. 16, No. 3, Jun. 1, 1969, pp. 421-425, XP011351570, ISSN: 0018-9499, DOI: 10.1109/TNS.1969. 4325264 abstract; figures 1-4a Chap. 1, p. 421-2; chap. 11 from p. 423, col. 2 to p. 425, col. 1. (5 pages).
Ormrod, J.H., et al., "The Chalk-River Superconducting Cyclotron", Proceedings of $8^{th}$ International Conference on Cyclotrons and their applications '79, 1979 (6 pages).
Ormrod, J.H., et al, "Status of the Chalk-River Superconducting Heavy-Ion Cyclotron", Proceedings of $9^{th}$ International Conference on Cyclotrons and their Applications '81, 1981 (9 pages).
Dey, M.K., et al., "Coil Centering for the Kolkata Superconducting Cyclotron Magnet", Cyclotrons and their applications, Proceedings, $18^{th}$ International Conference, Cyclotrons 2007, Giardini Naxo, Italy, Oct. 1-5, 2007 (3 pages).
Office Action in counterpart Chinese application No. 20138062102. X, dated Sep. 14, 2016 (Chinese language).
Office Action in counterpart Chinese application No. 201380062102.X, dated Sep. 14, 2016 (English translation).

* cited by examiner

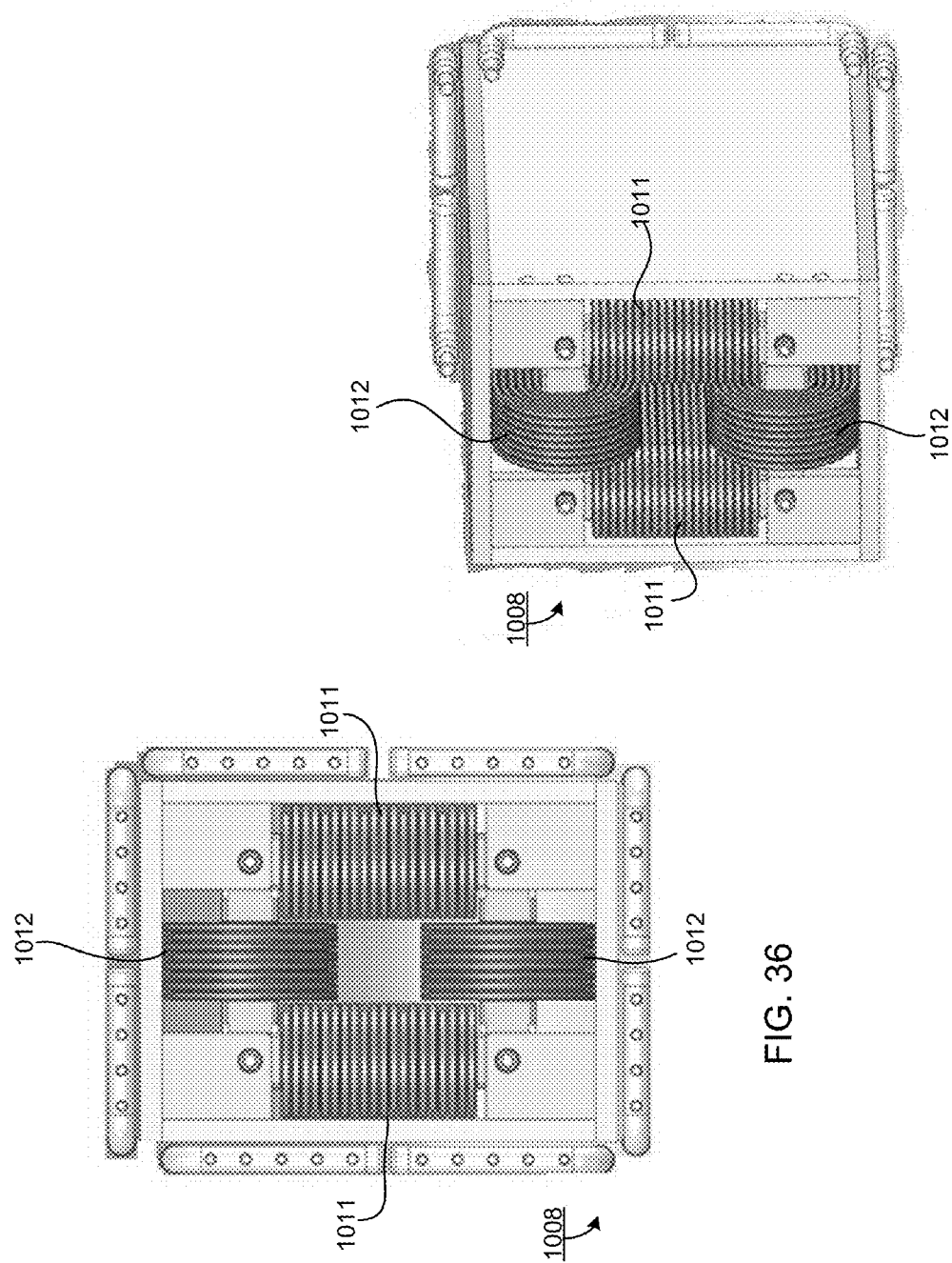

CONTROLLING PARTICLE THERAPY

CROSS-REFERENCE TO RELATED APPLICATION

Priority is hereby claimed to U.S. Provisional Application No. 61/707,624, which was filed on Sep. 28, 2012. The contents of U.S. Provisional Application No. 61/707,624 are hereby incorporated by reference into this disclosure.

TECHNICAL FIELD

This disclosure relates generally to controlling particle therapy.

BACKGROUND

Particle therapy systems use an accelerator to generate a particle beam for treating afflictions, such as tumors. In operation, the particle beam is accelerated inside a cavity of the particle accelerator, and removed from the cavity through an extraction channel. Various elements are used to focus the particle beam and apply it to appropriate areas of a patient.

Different patients may require different treatment plans. A prescription defines various operational characteristics of a particle therapy system, which may be used to implement a treatment plan. Information in the prescription is translated into various machine instructions that are used to configure to the particle therapy system to achieve the operational characteristics required by the prescription.

SUMMARY

An example particle therapy system includes the following: a gantry that is rotatable relative to a patient position; a particle accelerator mounted to the gantry, where the particle accelerator is for outputting a particle beam essentially directly to the patient position; and a control system to receive a prescription and to generate machine instructions for configuring one or more operational characteristics of the particle therapy system. At least one of the operational characteristics relates to, or is affected by, a rotational angle of the gantry relative to the patient position. The example particle therapy system may include one or more of the following features, either alone or in combination.

The particle therapy may include a particle source to provide pulses of ionized plasma to a cavity. A pulse of the particle source may have a pulse width corresponding to a duration of operation of the particle source to produce the pulse. The at least one operational characteristic may be a multiplier that is based on a rotational position of the gantry and that that is applied to the pulse width.

At least one of the operational characteristics may be a dosage of particles output by the particle accelerator.

At least one of the operational characteristics may be a dose rate of particles output by the particle accelerator. The example particle therapy system may include the following: a particle source to provide pulses of ionized plasma to a cavity, where each pulse of the particle source has a pulse width that corresponds to a duration of operation of the particle source to produce the corresponding pulse; and a modulator wheel having different thicknesses, where each thickness extends across a different circumferential length of the modulator wheel. Configuring the dose rate may include varying pulse widths based on rotational position of the modulator wheel.

At least one of the operational characteristics may be a position of a patient. The example particle therapy system may include a structure on which the patient lies, where the structure corresponds to the patient position. Configuring the position of the patient may include moving the structure relative to one or more coordinate positions.

At least one of the operational characteristics may be field size of a particle beam output by the particle accelerator. The example particle therapy system may include scattering devices having different configurations for changing the field size of the particle beam. Configuring the field size may include selecting one of the scattering devices to move into a path of the particle beam, and moving the selected scattering device into the path of the particle beam.

At least one of the operational characteristics may be depth (into a patient) of a particle beam output by the particle accelerator. The example particle therapy system may include an absorber having different thicknesses for absorbing particle beam. Configuring the depth may include controlling the absorber so as to place a specific thickness in a path of the particle beam.

The example particle therapy system may include one or more modulator wheels. Each modulator wheel may have different thicknesses. Each thickness may extend across a different circumferential length of the modulator wheel. Configuring the depth may include selecting a modulator wheel to move into a path of the particle beam.

The example particle therapy system may include a particle source to provide pulses of ionized plasma to a cavity. Each pulse of the particle source has a pulse width corresponding to a duration of operation of the particle source to produce the corresponding pulse. Configuring the depth may include selecting a file containing instructions for varying pulse width based on a rotational position of a selected modulator wheel. Configuring the extent of the depth of a particle beam may include turning-off the particle source at specific rotational positions of the modulator wheel.

At least one of the operational characteristics includes a shape of a particle beam output by the particle accelerator. The example particle therapy system may include one or more apertures corresponding to different shapes. Configuring the shape of particle beam may include selecting one of the apertures and moving the selected aperture into a path of the particle beam.

At least one of the operational characteristics includes a depth-wise shape of a particle beam output by the particle accelerator. The example particle therapy system may include a range compensating bolus. Configuring the depth-wise shape of particle beam may include moving the range compensating bolus into a path of the particle beam.

The foregoing operational characteristics may be configured individually or in any appropriate combination.

The control system may include one or more computing devices programmed to control elements of the particle therapy system that control the operational characteristics based on machine instructions.

The particle therapy system may include a scanning system, and one or more of the operational characteristics may relate to the scanning system. Configuring one or more operational characteristics of the particle therapy system may be performed using open-loop control or using closed-loop control.

Configuring one or more operational characteristics of the particle therapy system may include adjusting a position of a microabsorber wheel, adjusting a magnetic current of a superconducting magnet in the particle accelerator, and changing a pulse width of particle pulses output from the accelerator.

Two or more of the features described in this disclosure, including those described in this summary section, may be combined to form implementations not specifically described herein.

Control of the various systems described herein, or portions thereof, may be implemented via a computer program product that includes instructions that are stored on one or more non-transitory machine-readable storage media, and that are executable on one or more processing devices. The systems described herein, or portions thereof, may be implemented as an apparatus, method, or electronic system that may include one or more processing devices and memory to store executable instructions to implement control of the stated functions.

The details of one or more implementations are set forth in the accompanying drawings and the description below. Other features, objects, and advantages will be apparent from the description and drawings, and from the claims.

DESCRIPTION OF DRAWINGS

FIGS. 36 and 37 are front and perspective views, respectively, of an example scanning magnet that may be used in the example scanning system.

Like reference symbols in the various drawings indicate like elements.

DETAILED DESCRIPTION

Overview

Figure 1:
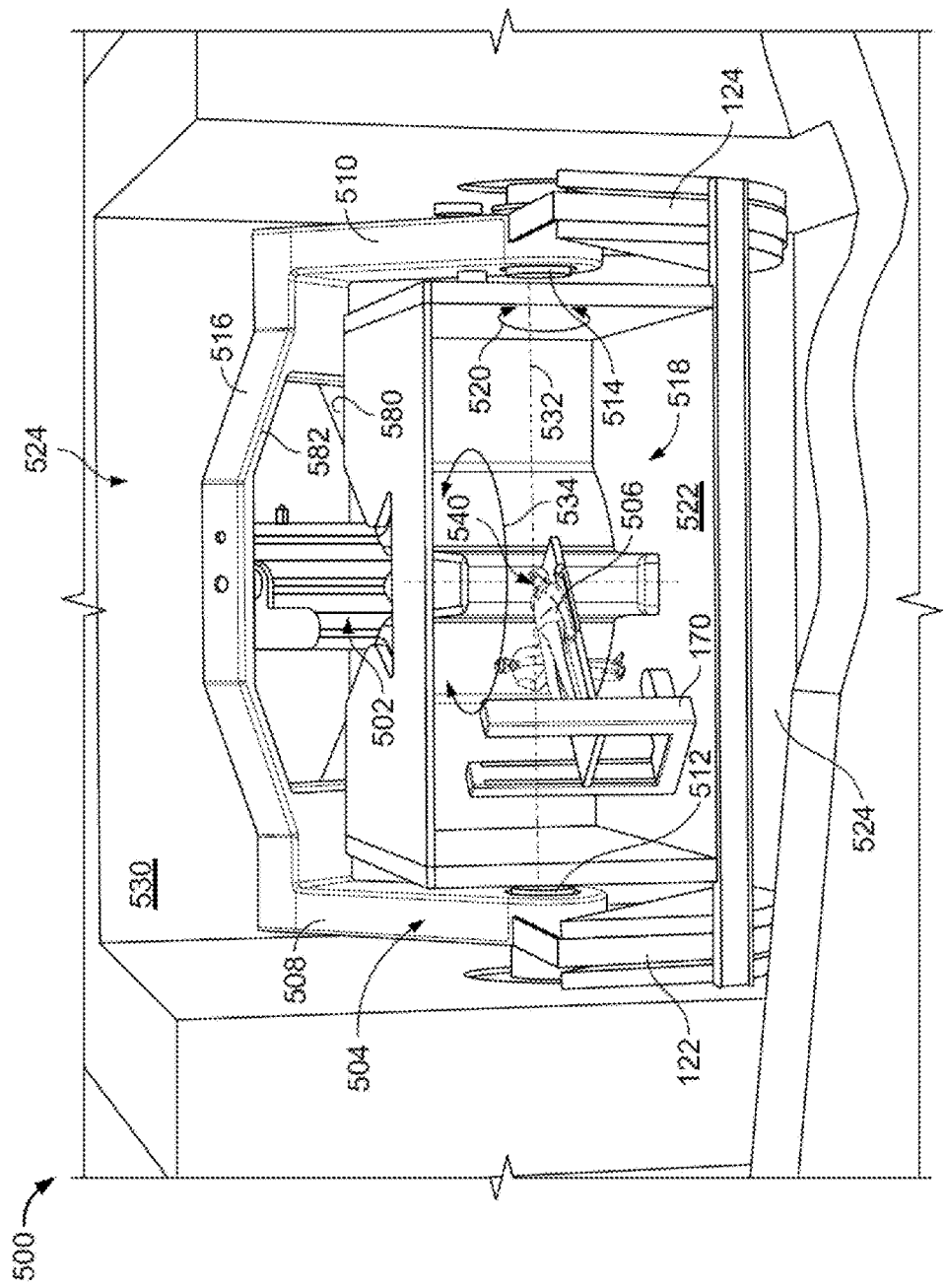
FIG. 1 is a perspective view of an example therapy system.
Figure 2:
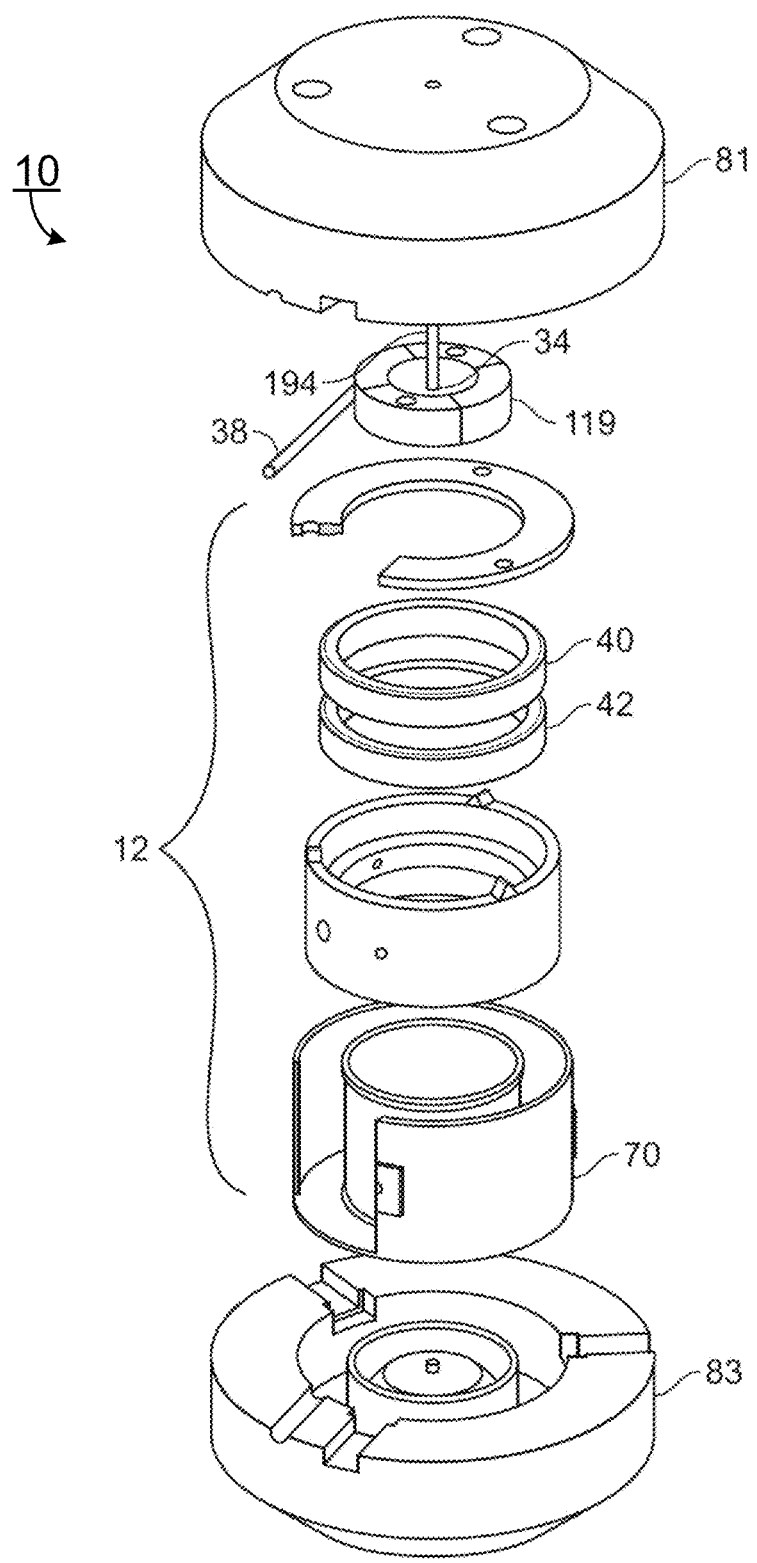
FIG. 2 is an exploded perspective view of components of an example synchrocyclotron.

Described herein is an example of a particle therapy system, such as a proton or ion therapy system. The particle therapy system includes a particle accelerator—in this example, a synchrocyclotron—mounted on a gantry. The gantry enables the accelerator to be rotated around a patient position, as explained in more detail below. In some implementations, the gantry is steel and has two legs mounted for rotation on two respective bearings that lie on opposite sides of a patient. The particle accelerator is supported by a steel truss that is long enough to span a treatment area in which the patient lies and that is attached stably at both ends to the rotating legs of the gantry. As a result of rotation of the gantry around the patient, the particle accelerator also rotates.

In an example implementation, the particle accelerator (e.g., the synchrocyclotron) includes a cryostat that holds a superconducting coil for conducting a current that generates a magnetic field (B). In this example, the cryostat uses liquid helium (He) to maintain the coil at superconducting temperatures, e.g., 4° Kelvin (K). Magnetic yokes are adjacent (e.g., around) the cryostat, and define a cavity in which particles are accelerated. The cryostat is attached to the magnetic yokes through straps or the like.

In this example implementation, the particle accelerator includes a particle source (e.g., a Penning Ion Gauge—PIG source) to provide a plasma column to the cavity. Hydrogen gas is ionized to produce the plasma column. A voltage source provides a radio frequency (RF) voltage to the cavity to accelerate particles from the plasma column. As noted, in this example, the particle accelerator is a synchrocyclotron. Accordingly, the RF voltage is swept across a range of frequencies to account for relativistic effects on the particles (e.g., increasing particle mass) when extracting particles from the column. The magnetic field produced by the coil causes particles accelerated from the plasma column to accelerate orbitally within the cavity. A magnetic field regenerator is positioned in the cavity and may be used to adjust the existing magnetic field inside the cavity to thereby change locations of successive orbits of the particles accelerated from the plasma column so that, eventually, the particles output to an extraction channel that passes through the yokes. The extraction channel receives particles accelerated from the plasma column and outputs the received particles from the cavity. Elements both inside and outside the extraction channel shape and focus the particle beam for application.

The particle beam is applied to a patient in accordance with a particular treatment plan. A prescription defines operational characteristics of the particle therapy system that are used to implement the treatment plan. A control system, which may be part of the particle therapy system, translates the prescription into machine instructions, including, but not limited to, commands, parameters, and/or other machine-usable information.

In this regard, the control system may include one or more computers, processing devices, and the like that are programmed to use the instructions translated from the prescription to control various operational aspects of the particle therapy system. In some implementations, translation is performed using mathematical processes and/or look-up table(s) (LUT), as described below. Although a prescription may specify any number of operational characteristics appropriate to a particular particle therapy system, in an implementation, the prescription specifies one or more of the following: particle dose, particle dose rate, patient position (as defined by a "couch" on which the patient lies), patient couch rotational angle, gantry rotational angle, beam field size, beam depth, an extent of the beam depth, a configuration of an aperture used to limit the area of the particle beam, and a configuration of a range compensating bolus (or, simply, "bolus") used to customize the penetration depth of the particle beam. Each of these operational characteristics is described in more detail below.

Once the control system has obtained the machine instructions, the control system uses those machine instructions to configure the particle therapy system so that it has operational characteristics appropriate for the treatment plan. The particle therapy system is configurable on a case-by-case basis.

The techniques described herein for controlling particle therapy are not limited to use with a particular particle therapy system, but rather may be used in any appropriate particle therapy system. The foregoing techniques also may be used in other appropriate medical treatment or diagnostic systems.

An example of a particle therapy system in which the techniques described herein may be used is provided below.

Example Particle Therapy System

Referring to FIG. 1, a charged particle radiation therapy system 500 includes a beam-producing particle accelerator 502 having a weight and size small enough to permit it to be mounted on a rotating gantry 504 with its output directed straight (that is, essentially directly) from the accelerator housing toward a patient 506.

In some implementations, the steel gantry has two legs 508, 510 mounted for rotation on two respective bearings 512, 514 that lie on opposite sides of the patient. The accelerator is supported by a steel truss 516 that is long enough to span a treatment area 518 in which the patient lies (e.g., twice as long as a tall person, to permit the person to be rotated fully within the space with any desired target area of the patient remaining in the line of the beam) and is attached stably at both ends to the rotating legs of the gantry.

In some examples, the rotation of the gantry is limited to a range 520 of less than 360 degrees, e.g., about 180 degrees, to permit a floor 522 to extend from a wall of the vault 524 that houses the therapy system into the patient treatment area. The limited rotation range of the gantry also reduces the required thickness of some of the walls, which provide radiation shielding of people outside the treatment area. A range of 180 degrees of gantry rotation is enough to cover all treatment approach angles, but providing a larger range of travel can be useful. For example the range of rotation may be between 180 and 330 degrees and still provide clearance for the therapy floor space.

The horizontal rotational axis 532 of the gantry is located nominally one meter above the floor where the patient and therapist interact with the therapy system. This floor is positioned about 3 meters above the bottom floor of the therapy system shielded vault. The accelerator can swing under the raised floor for delivery of treatment beams from below the rotational axis. The patient couch moves and rotates in a substantially horizontal plane parallel to the rotational axis of the gantry. The couch can rotate through a range 534 of about 270 degrees in the horizontal plane with this configuration. This combination of gantry and patient rotational ranges and degrees of freedom allow the therapist to select virtually any approach angle for the beam. If needed, the patient can be placed on the couch in the opposite orientation and then all possible angles can be used.

In some implementations, the accelerator uses a synchrocyclotron configuration having a very high magnetic field superconducting electromagnetic structure. Because the bend radius of a charged particle of a given kinetic energy is reduced in direct proportion to an increase in the magnetic field applied to it, the very high magnetic field superconducting magnetic structure permits the accelerator to be made smaller and lighter. The synchrocyclotron uses a magnetic field that is uniform in rotation angle and falls off in strength with increasing radius. Such a field shape can be achieved regardless of the magnitude of the magnetic field, so in theory there is no upper limit to the magnetic field strength (and therefore the resulting particle energy at a fixed radius) that can be used in a synchrocyclotron.

Superconducting materials lose their superconducting properties in the presence of very high magnetic fields. High performance superconducting wire windings are used to allow very high magnetic fields to be achieved.

Superconducting materials typically need to be cooled to low temperatures for their superconducting properties to be realized. In some examples described here, cryo-coolers are used to bring the superconducting coil windings to temperatures near absolute zero. Using cryo-coolers can reduce complexity and cost.

The synchrocyclotron is supported on the gantry so that the beam is generated directly in line with the patient. The gantry permits rotation of the cyclotron about a horizontal rotational axis that contains a point (isocenter 540) within, or near, the patient. The split truss that is parallel to the rotational axis, supports the cyclotron on both sides.

Because the rotational range of the gantry is limited, a patient support area can be accommodated in a wide area around the isocenter. Because the floor can be extended broadly around the isocenter, a patient support table can be positioned to move relative to and to rotate about a vertical axis 542 through the isocenter so that, by a combination of gantry rotation and table motion and rotation, any angle of beam direction into any part of the patient can be achieved. The two gantry arms are separated by more than twice the height of a tall patient, allowing the couch with patient to rotate and translate in a horizontal plane above the raised floor.

Limiting the gantry rotation angle allows for a reduction in the thickness of at least one of the walls surrounding the treatment room. Thick walls, typically constructed of concrete, provide radiation protection to individuals outside the treatment room. A wall downstream of a stopping proton beam may be about twice as thick as a wall at the opposite end of the room to provide an equivalent level of protection. Limiting the range of gantry rotation enables the treatment room to be sited below earth grade on three sides, while allowing an occupied area adjacent to the thinnest wall reducing the cost of constructing the treatment room.

In the example implementation shown in FIG. 1, the superconducting synchrocyclotron 502 operates with a peak magnetic field in a pole gap of the synchrocyclotron of 8.8 Tesla. The synchrocyclotron produces a beam of protons having an energy of 250 MeV. In other implementations the field strength could be in the range of 4 to 20 Tesla or 6 to 20 Tesla and the proton energy could be in the range of 150 to 300 MeV The radiation therapy system described in this example is used for proton radiation therapy, but the same principles and details can be applied in analogous systems for use in heavy ion (ion) treatment systems.

As shown in FIGS. 2, 3, 4, 5, and 6, an example synchrocyclotron 10 (e.g., 502 in FIG. 1) includes a magnet system 12 that contains an particle source 90, a radiofrequency drive system 91, and a beam extraction system 38. The magnetic field established by the magnet system has a shape appropriate to maintain focus of a contained proton beam using a combination of a split pair of annular superconducting coils 40, 42 and a pair of shaped ferromagnetic (e.g., low carbon steel) pole faces 44, 46.

Figure 7:
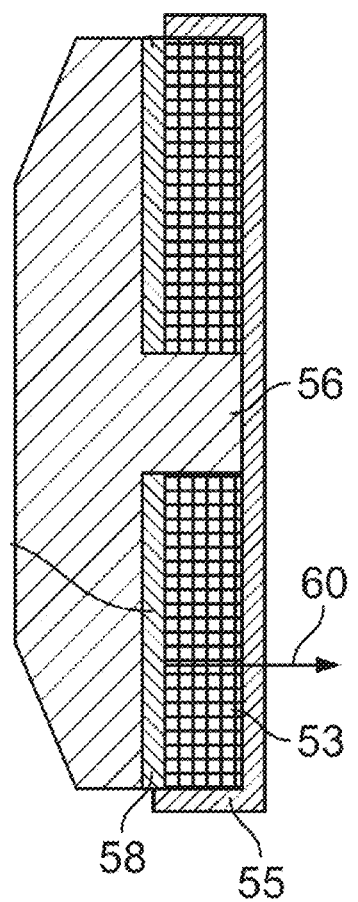
FIG. 7 is a cross-sectional view of a portion of an example reverse bobbin and windings.
Figure 8:
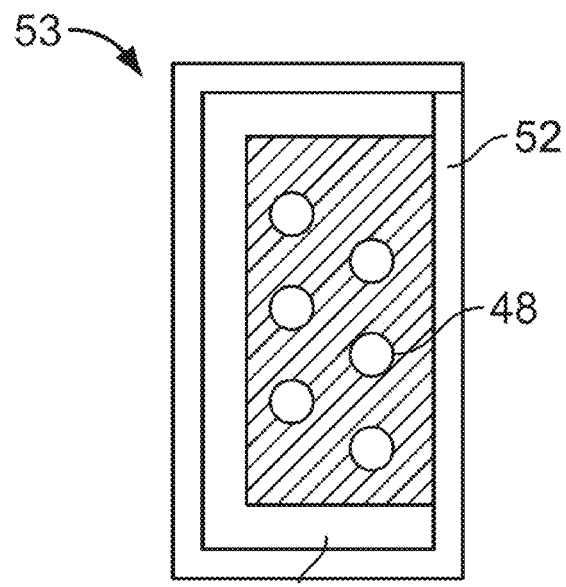
FIG. 8 is a cross sectional view of an example cable-in-channel composite conductor.

The two superconducting magnet coils are centered on a common axis 47 and are spaced apart along the axis. As shown in FIGS. 7 and 8, the coils are formed by of $Nb_3Sn$-based superconducting 0.8 mm diameter strands 48 (that initially comprise a niobium-tin core surrounded by a copper sheath) deployed in a twisted cable-in-channel conductor geometry. After seven individual strands are cabled together, they are heated to cause a reaction that forms the final (brittle) superconducting material of the wire. After the material has been reacted, the wires are soldered into the copper channel (outer dimensions 3.18×2.54 mm and inner dimensions 2.08×2.08 mm) and covered with insulation 52 (in this example, a woven fiberglass material). The copper channel containing the wires 53 is then wound in a coil having a rectangular cross-section of 8.55 cm×19.02 cm, having 26 layers and 49 turns per layer. The wound coil is then vacuum impregnated with an epoxy compound. The finished coils are mounted on an annular stainless steel reverse bobbin 56. Heater blankets 55 are placed at intervals in the layers of the windings to protect the assembly in the event of a magnet quench.

The entire coil can then be covered with copper sheets to provide thermal conductivity and mechanical stability and then contained in an additional layer of epoxy. The precompression of the coil can be provided by heating the stainless steel reverse bobbin and fitting the coils within the reverse bobbin. The reverse bobbin inner diameter is chosen so that when the entire mass is cooled to 4 K, the reverse bobbin stays in contact with the coil and provides some compression. Heating the stainless steel reverse bobbin to approximately 50 degrees C. and fitting coils at a temperature of 100 degrees Kelvin can achieve this.

Figure 5:
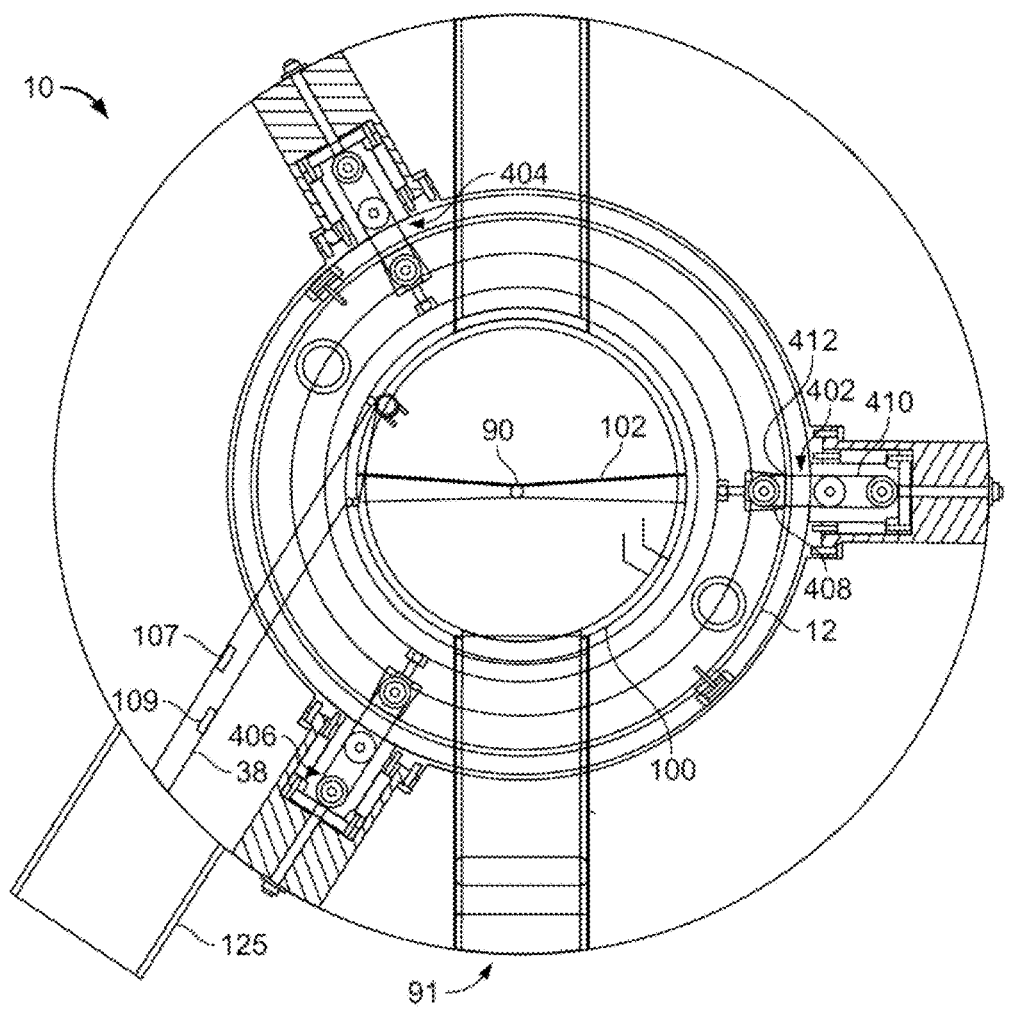
Figure 6:
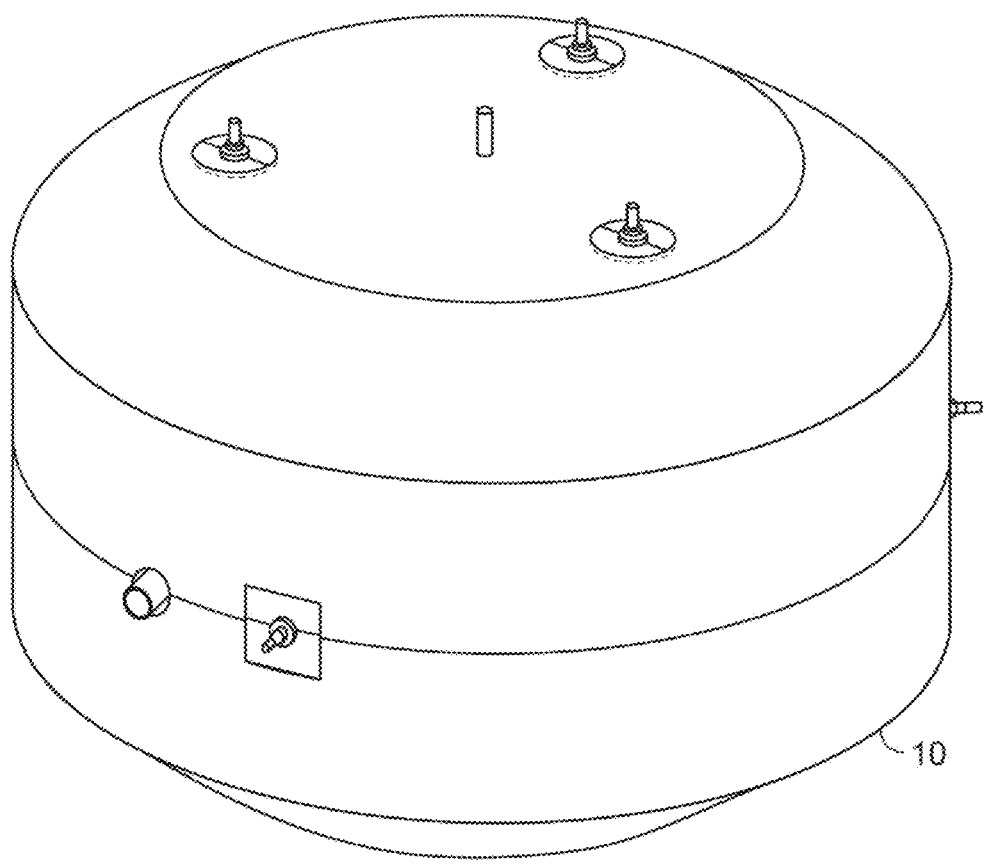
FIG. 6 is a perspective view of an example synchrocyclotron.

The geometry of the coil is maintained by mounting the coils in a reverse rectangular bobbin 56 to exert a restorative force 60 that works against the distorting force produced when the coils are energized. As shown in FIG. 5, the coil position is maintained relative to the magnet yoke and cryostat using a set of warm-to-cold support straps 402, 404, 406. Supporting the cold mass with thin straps reduces the heat leakage imparted to the cold mass by the rigid support system. The straps are arranged to withstand the varying gravitational force on the coil as the magnet rotates on board the gantry. They withstand the combined effects of gravity and the large de-centering force realized by the coil when it is perturbed from a perfectly symmetric position relative to the magnet yoke. Additionally the links act to reduce dynamic forces imparted on the coil as the gantry accelerates and decelerates when its position is changed. Each warm-to-cold support includes one S2 fiberglass link and one carbon fiber link. The carbon fiber link is supported across pins between the warm yoke and an intermediate temperature (50-70 K), and the S2 fiberglass link 408 is supported across the intermediate temperature pin and a pin attached to the cold mass. Each link is 5 cm long (pin center to pin center) and is 17 mm wide. The link thickness is 9 mm. Each pin is made of high strength stainless steel and is 40 mm in diameter.

Figure 3:
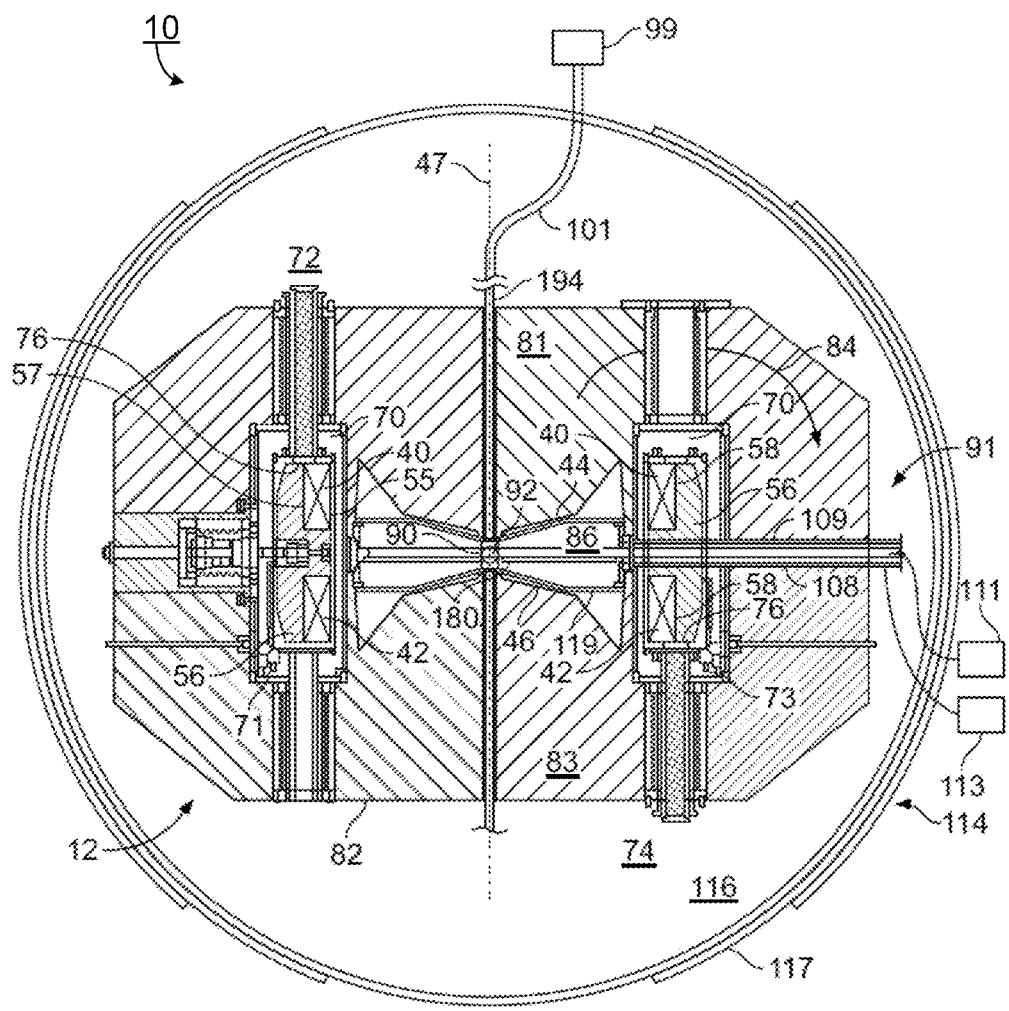
FIGS. 3, 4, and 5 are cross-sectional views of an example synchrocyclotron.
Figure 4:
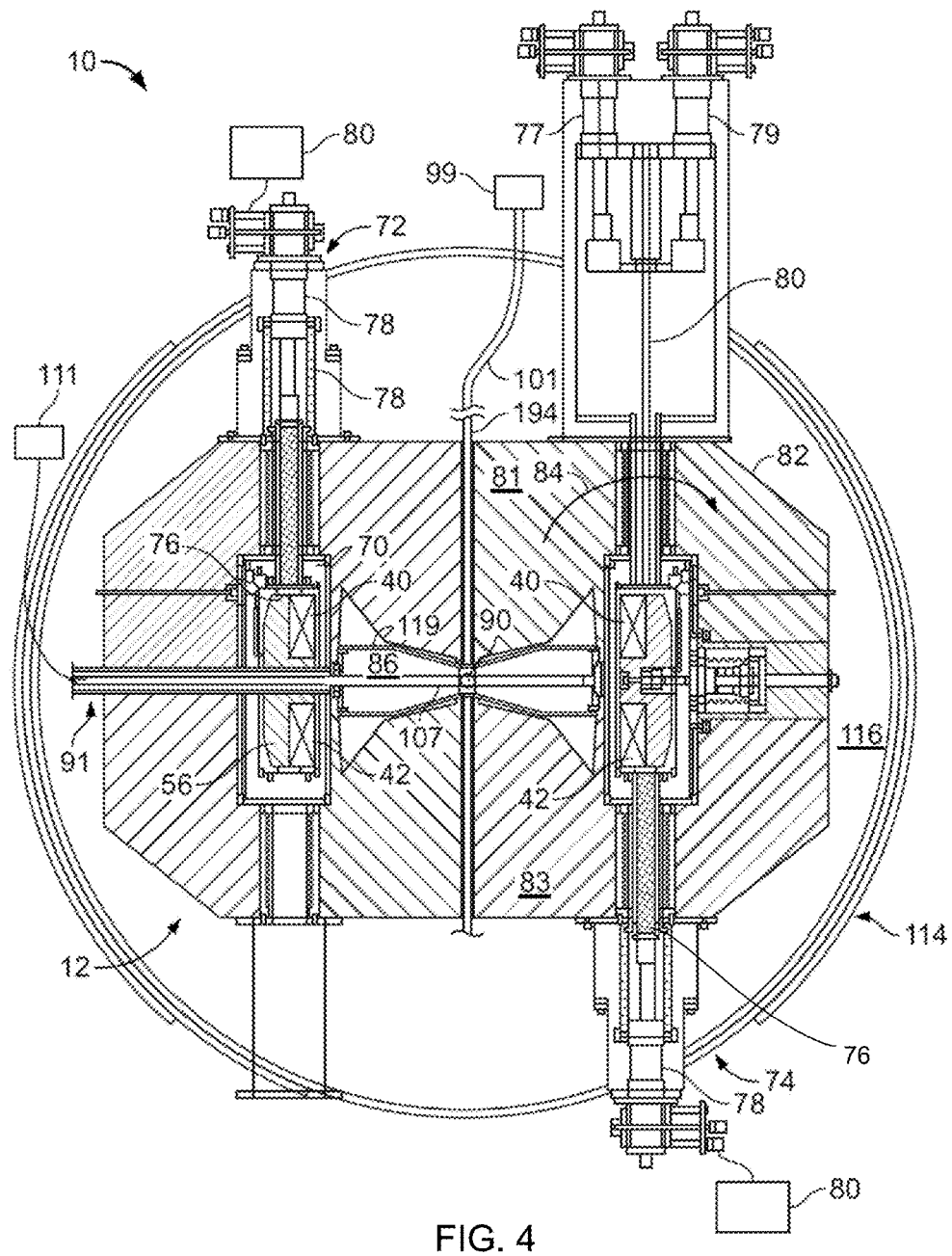

Referring to FIG. 3, the field strength profile as a function of radius is determined largely by choice of coil geometry and pole face shape; the pole faces 44, 46 of the permeable yoke material can be contoured to fine tune the shape of the magnetic field to ensure that the particle beam remains focused during acceleration.

The superconducting coils are maintained at temperatures near absolute zero (e.g., about 4 degrees Kelvin) by enclosing the coil assembly (the coils and the bobbin) inside an evacuated annular aluminum or stainless steel cryostatic chamber 70 that provides a free space around the coil structure, except at a limited set of support points 71, 73. In an alternate version (FIG. 4) the outer wall of the cryostat may be made of low carbon steel to provide an additional return flux path for the magnetic field.

In some implementations, the temperature near absolute zero is achieved and maintained using one single-stage Gifford-McMahon cryo-cooler and three two-stage Gifford McMahon cryo-coolers. Each two stage cryo-cooler has a second stage cold end attached to a condenser that recondenses Helium vapor into liquid Helium. The cryo-cooler heads are supplied with compressed Helium from a compressor. The single-stage Gifford-McMahon cryo-cooler is arranged to cool high temperature (e.g., 50-70 degrees Kelvin) leads that supply current to the superconducting windings.

In some implementations, the temperature near absolute zero is achieved and maintained using two Gifford-McMahon cryo-coolers 72, 74 that are arranged at different positions on the coil assembly. Each cryo-cooler has a cold end 76 in contact with the coil assembly. The cryo-cooler heads

78 are supplied with compressed Helium from a compressor 80. Two other Gifford-McMahon cryo-coolers 77, 79 are arranged to cool high temperature (e.g., 60-80 degrees Kelvin) leads that supply current to the superconducting windings.

The coil assembly and cryostatic chambers are mounted within and fully enclosed by two halves 81, 83 of a pillbox-shaped magnet yoke 82. In this example, the inner diameter of the coil assembly is about 74.6 cm. The iron yoke 82 provides a path for the return magnetic field flux 84 and magnetically shields the volume 86 between the pole faces 44, 46 to prevent external magnetic influences from perturbing the shape of the magnetic field within that volume. The yoke also serves to decrease the stray magnetic field in the vicinity of the accelerator. In some implementations, the synchrocyclotron may have an active return system to reduce stray magnetic fields. An example of an active return system is described in U.S. patent application Ser. No. 13/907,601, which was filed on May 31, 2013, the contents of which are incorporated herein by reference. In the active return system, the relatively large magnetic yokes described herein are replaced by smaller magnetic structures, referred to as pole pieces. Superconducting coils run current opposite to the main coils described herein in order to provide magnetic return and thereby reduce stray magnetic fields.

Figure 9:
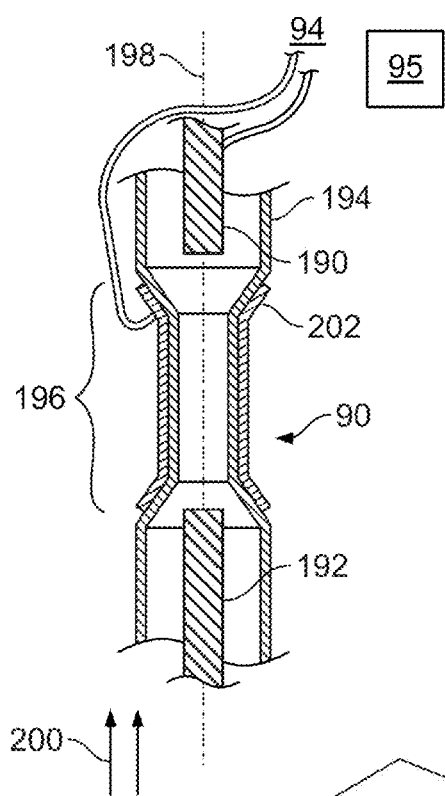
FIG. 9 is a cross-sectional view of an example ion source.

As shown in FIGS. 3 and 9, the synchrocyclotron includes a particle source 90 of a Penning ion gauge geometry located near the geometric center 92 of the magnet structure 82. The particle source may be as described below, or the particle source may be of the type described in U.S. patent application Ser. No. 11/948,662 incorporated herein by reference.

Particle source 90 is fed from a supply 99 of hydrogen through a gas line 101 and tube 194 that delivers gaseous hydrogen. Electric cables 94 carry an electric current from a current source 95 to stimulate electron discharge from cathodes 192, 190 that are aligned with the magnetic field, 200.

In some implementations, the gas in gas tube 101 may include a mixture of hydrogen and one or more other gases. For example, the mixture may contain hydrogen and one or more of the noble gases, e.g., helium, neon, argon, krypton, xenon and/or radon (although the mixture is not limited to use with the noble gases). In some implementations, the mixture may be a mixture of hydrogen and helium. For example, the mixture may contain about 75% or more of hydrogen and about 25% or less of helium (with possible trace gases included). In another example, the mixture may contain about 90% or more of hydrogen and about 10% or less of helium (with possible trace gases included). In examples, the hydrogen/helium mixture may be any of the following: >95%/<5%, >90%/<10%, >85%/<15%, >80%/<20%, >75%/<20%, and so forth.

Possible advantages of using a noble (or other) gas in combination with hydrogen in the particle source may include: increased beam intensity, increased cathode longevity, and increased consistency of beam output.

In this example, the discharged electrons ionize the gas exiting through a small hole from tube 194 to create a supply of positive ions (protons) for acceleration by one semicircular (dee-shaped) radio-frequency plate 100 that spans half of the space enclosed by the magnet structure and one dummy dee plate 102. In the case of an interrupted particle source (an example of which is described in U.S. patent application Ser. No. 11/948,662), all (or a substantial part) of the tube containing plasma is removed at the acceleration region, thereby allowing ions to be more rapidly accelerated in a relatively high magnetic field.

Figure 10:
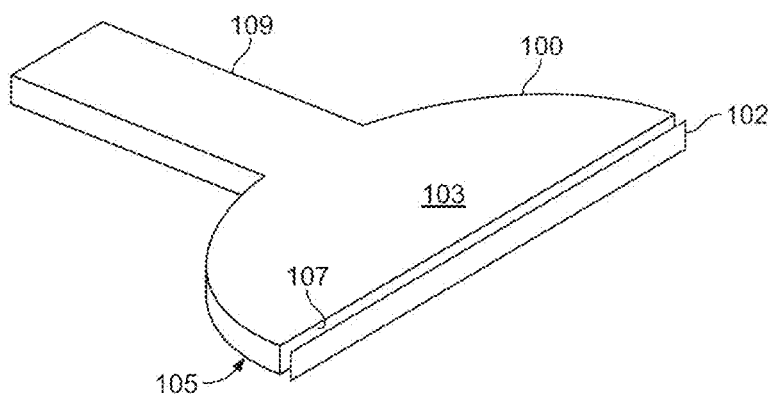
FIG. 10 is a perspective view of an example dee plate and an example dummy dee.

As shown in FIG. 10, the dee plate 100 is a hollow metal structure that has two semicircular surfaces 103, 105 that enclose a space 107 in which the protons are accelerated during half of their rotation around the space enclosed by the magnet structure. A duct 109 opening into the space 107 extends through the yoke to an external location from which a vacuum pump 111 can be attached to evacuate the space 107 and the rest of the space within a vacuum chamber 119 in which the acceleration takes place. The dummy dee 102 comprises a rectangular metal ring that is spaced near to the exposed rim of the dee plate. The dummy dee is grounded to the vacuum chamber and magnet yoke. The dee plate 100 is driven by a radio-frequency signal that is applied at the end of a radio-frequency transmission line to impart an electric field in the space 107. The radio frequency electric field is made to vary in time as the accelerated particle beam increases in distance from the geometric center. The radio frequency electric field may be controlled in the manner described in U.S. patent application Ser. No. 11/948,359, entitled "Matching A Resonant Frequency Of A Resonant Cavity To A Frequency Of A" Input Voltage", the contents of which are incorporated herein by reference.

For the beam emerging from the centrally located particle source to clear the particle source structure as it begins to spiral outward, a large voltage difference is required across the radio frequency plates. 20,000 Volts is applied across the radio frequency plates. In some versions from 8,000 to 20,000 Volts may be applied across the radio frequency plates. To reduce the power required to drive this large voltage, the magnet structure is arranged to reduce the capacitance between the radio frequency plates and ground. This is done by forming holes with sufficient clearance from the radio frequency structures through the outer yoke and the cryostat housing and making sufficient space between the magnet pole faces.

The high voltage alternating potential that drives the dee plate has a frequency that is swept downward during the accelerating cycle to account for the increasing relativistic mass of the protons and the decreasing magnetic field. The dummy dee does not require a hollow semi-cylindrical structure as it is at ground potential along with the vacuum chamber walls. Other plate arrangements could be used such as more than one pair of accelerating electrodes driven with different electrical phases or multiples of the fundamental frequency. The RF structure can be tuned to keep the Q high during the required frequency sweep by using, for example, a rotating capacitor having intermeshing rotating and stationary blades. During each meshing of the blades, the capacitance increases, thus lowering the resonant frequency of the RF structure. The blades can be shaped to create a precise frequency sweep required. A drive motor for the rotating condenser can be phase locked to the RF generator for precise control. One bunch of particles is accelerated during each meshing of the blades of the rotating condenser.

The vacuum chamber 119 in which the acceleration occurs is a generally cylindrical container that is thinner in the center and thicker at the rim. The vacuum chamber encloses the RF plates and the particle source and is evacuated by the vacuum pump 111. Maintaining a high vacuum insures that accelerating ions are not lost to collisions with gas molecules and enables the RF voltage to be kept at a higher level without arcing to ground.

Protons traverse a generally spiral orbital path beginning at the particle source. In half of each loop of the spiral path, the protons gain energy as they pass through the RF electric field in space 107. As the ions gain energy, the radius of the central orbit of each successive loop of their spiral path is larger than the prior loop until the loop radius reaches the maximum radius of the pole face. At that location a magnetic and electric field perturbation directs ions into an area where the magnetic field rapidly decreases, and the ions depart the area of the high magnetic field and are directed through an evacuated tube 38, referred to herein as the extraction channel, to exit the yoke of the cyclotron. A magnetic regenerator may be used to change the magnetic field perturbation to direct the ions. The ions exiting the cyclotron will tend to disperse as they enter the area of markedly decreased magnetic field that exists in the room around the cyclotron. Beam shaping elements 107, 109 in the extraction channel 38 redirect the ions so that they stay in a straight beam of limited spatial extent.

The magnetic field within the pole gap needs to have certain properties to maintain the beam within the evacuated chamber as it accelerates. The magnetic field index n, which is shown below, $$n=-(r/B)dB/dr,$$

should be kept positive to maintain this "weak" focusing. Here r is the radius of the beam and B is the magnetic field. Additionally, in some implementations, the field index needs to be maintained below 0.2, because at this value the periodicity of radial oscillations and vertical oscillations of the beam coincide in a $v_r=2 v_z$ resonance. The betatron frequencies are defined by $v_r=(1-n)^{1/2}$ and $v_z=n^{1/2}$. The ferromagnetic pole face is designed to shape the magnetic field generated by the coils so that the field index n is maintained positive and less than 0.2 in the smallest diameter consistent with a 250 MeV beam in the given magnetic field.

As the beam exits the extraction channel it is passed through a beam formation system 125 (FIG. 5) that can be programmably controlled to create a desired combination of scanning, scattering, and/or range modulation for the beam. Examples of beam forming systems useful for that purpose are described in U.S. Beam formation system 125 may be used in conjunction with an inner gantry 601 (FIG. 14) to direct a beam to the patient.

During operation, the plates absorb energy from the applied radio frequency field as a result of conductive resistance along the surfaces of the plates. This energy appears as heat and is removed from the plates using water cooling lines 108 that release the heat in a heat exchanger 113 (FIG. 3).

Stray magnetic fields exiting from the cyclotron are limited by both the pillbox magnet yoke (which also serves as a shield) and a separate magnetic shield 114. The separate magnetic shield includes of a layer 117 of ferromagnetic material (e.g., steel or iron) that encloses the pillbox yoke, separated by a space 116. This configuration that includes a sandwich of a yoke, a space, and a shield achieves adequate shielding for a given leakage magnetic field at lower weight.

As mentioned, the gantry allows the synchrocyclotron to be rotated about the horizontal rotational axis 532. The truss structure 516 has two generally parallel spans 580, 582. The synchrocyclotron is cradled between the spans about midway between the legs. The gantry is balanced for rotation about the bearings using counterweights 122, 124 mounted on ends of the legs opposite the truss.

The gantry is driven to rotate by an electric motor mounted to one or both of the gantry legs and connected to the bearing housings by drive gears. The rotational position of the gantry is derived from signals provided by shaft angle encoders incorporated into the gantry drive motors and the drive gears.

At the location at which the ion beam exits the cyclotron, the beam formation system 125 acts on the ion beam to give it properties suitable for patient treatment. For example, the beam may be spread and its depth of penetration varied to provide uniform radiation across a given target volume. The beam formation system can include passive scattering elements as well as active scanning elements.

All of the active systems of the synchrocyclotron (the current driven superconducting coils, the RF-driven plates, the vacuum pumps for the vacuum acceleration chamber and for the superconducting coil cooling chamber, the current driven particle source, the hydrogen gas source, and the RF plate coolers, for example), may be controlled by appropriate synchrocyclotron control electronics (not shown), which may include, e.g., one or more computers programmed with appropriate programs to effect control.

The control of the gantry, the patient support, the active beam shaping elements, and the synchrocyclotron to perform a therapy session is achieved by appropriate therapy control electronics (not shown).

Figure 11:
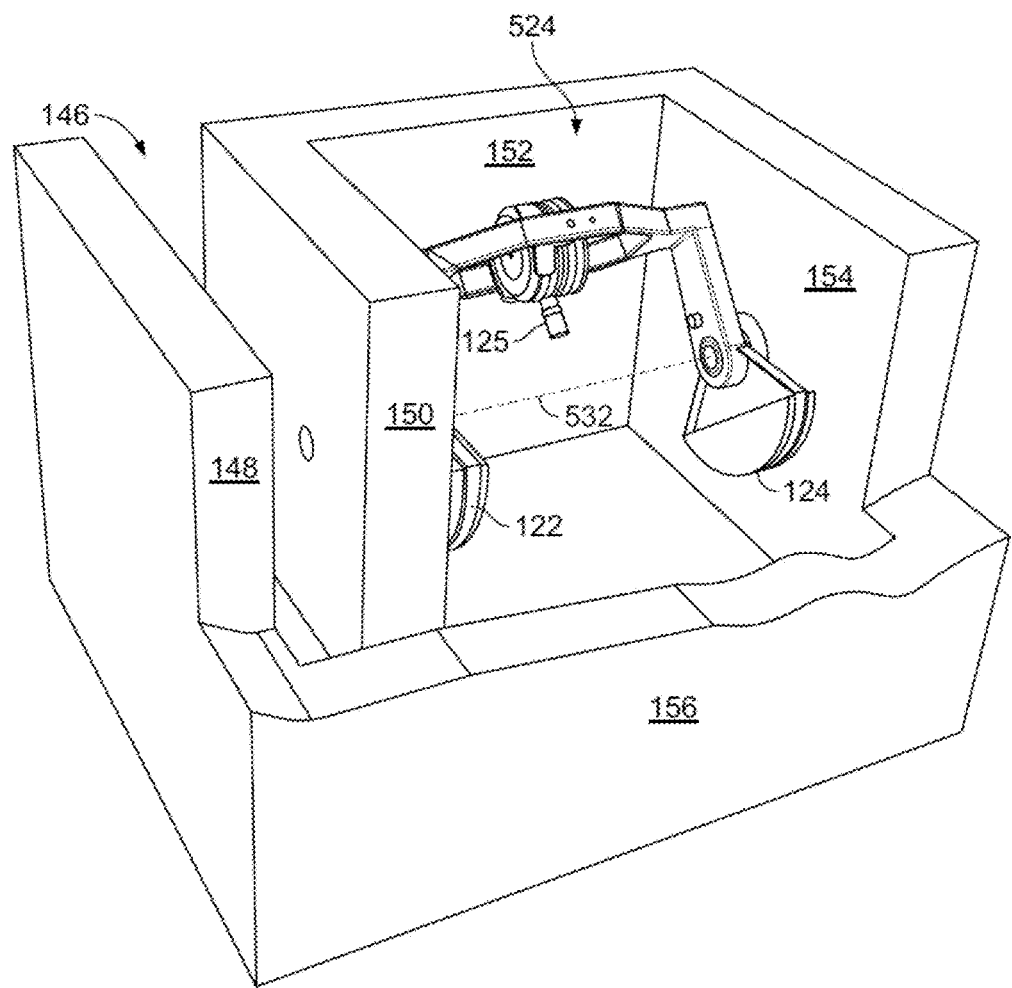
FIG. 11 is a perspective view of an example vault.
Figure 12:
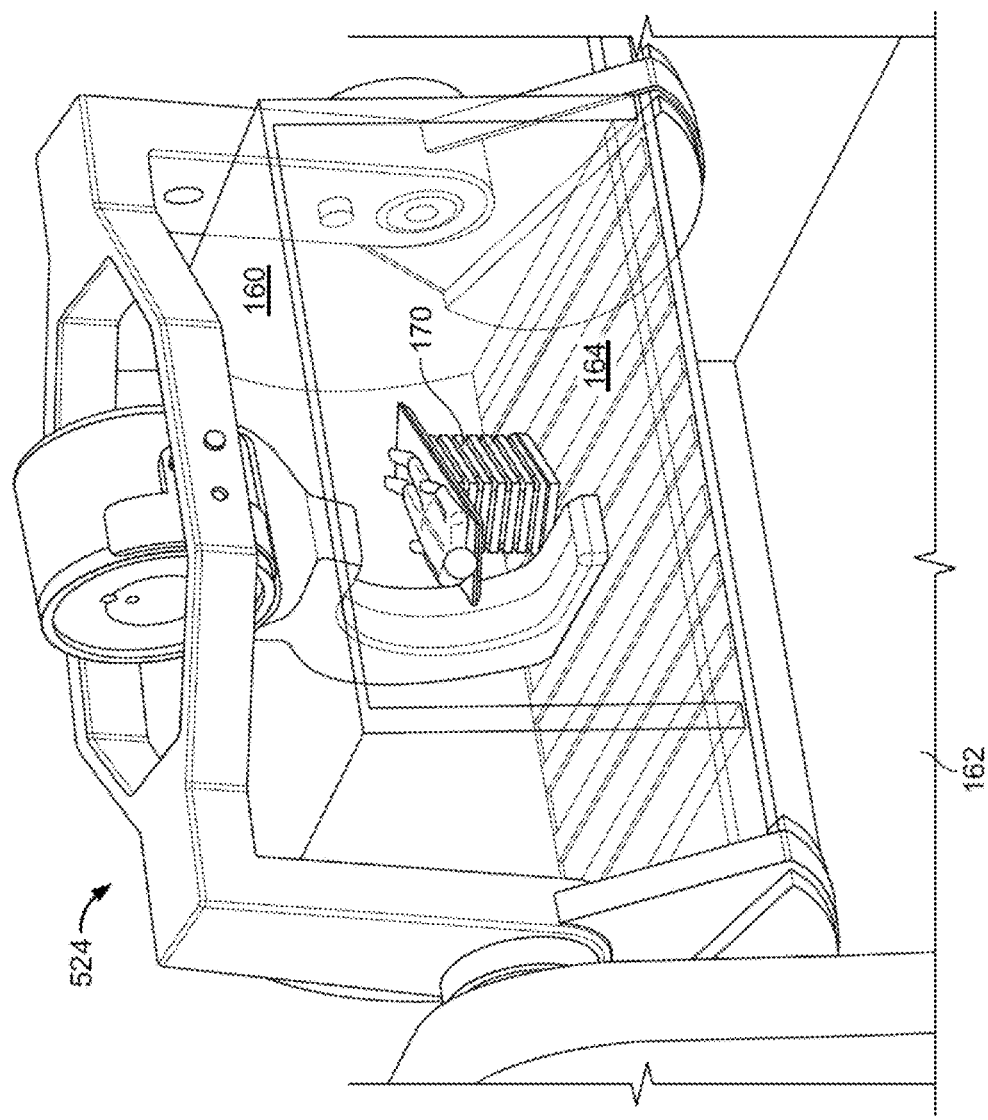
FIG. 12 is a perspective view of an example treatment room with a vault.

As shown in FIGS. 1, 11, and 12, the gantry bearings are supported by the walls of a cyclotron vault 524. The gantry enables the cyclotron to be swung through a range 520 of 180 degrees (or more) including positions above, to the side of, and below the patient. The vault is tall enough to clear the gantry at the top and bottom extremes of its motion. A maze 146 sided by walls 148, 150 provides an entry and exit route for therapists and patients. Because at least one wall 152 is not in line with the proton beam directly from the cyclotron, it can be made relatively thin and still perform its shielding function. The other three side walls 154, 156, 150/148 of the room, which may need to be more heavily shielded, can be buried within an earthen hill (not shown). The required thickness of walls 154, 156, and 158 can be reduced, because the earth can itself provide some of the needed shielding.

Figure 13:
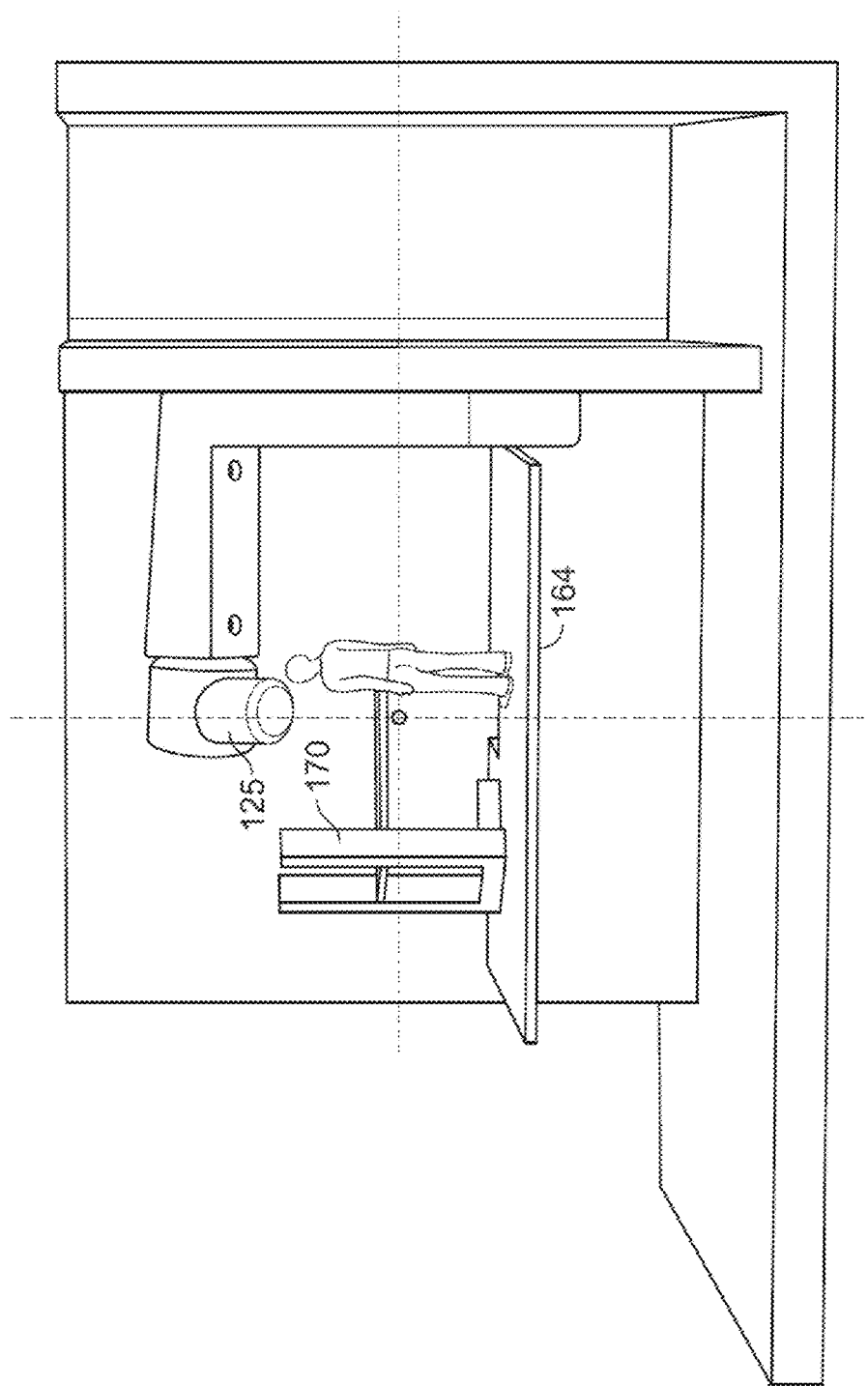
FIG. 13 shows a patient next to a particle accelerator.

Referring to FIGS. 12 and 13, for safety and aesthetic reasons, a therapy room 160 may be constructed within the vault. The therapy room is cantilevered from walls 154, 156, 150 and the base 162 of the containing room into the space between the gantry legs in a manner that clears the swinging gantry and also maximizes the extent of the floor space 164 of the therapy room. Periodic servicing of the accelerator can be accomplished in the space below the raised floor. When the accelerator is rotated to the down position on the gantry, full access to the accelerator is possible in a space separate from the treatment area. Power supplies, cooling equipment, vacuum pumps and other support equipment can be located under the raised floor in this separate space. Within the treatment room, the patient support 170 can be mounted in a variety of ways that permit the support to be raised and lowered and the patient to be rotated and moved to a variety of positions and orientations.

Figure 14:
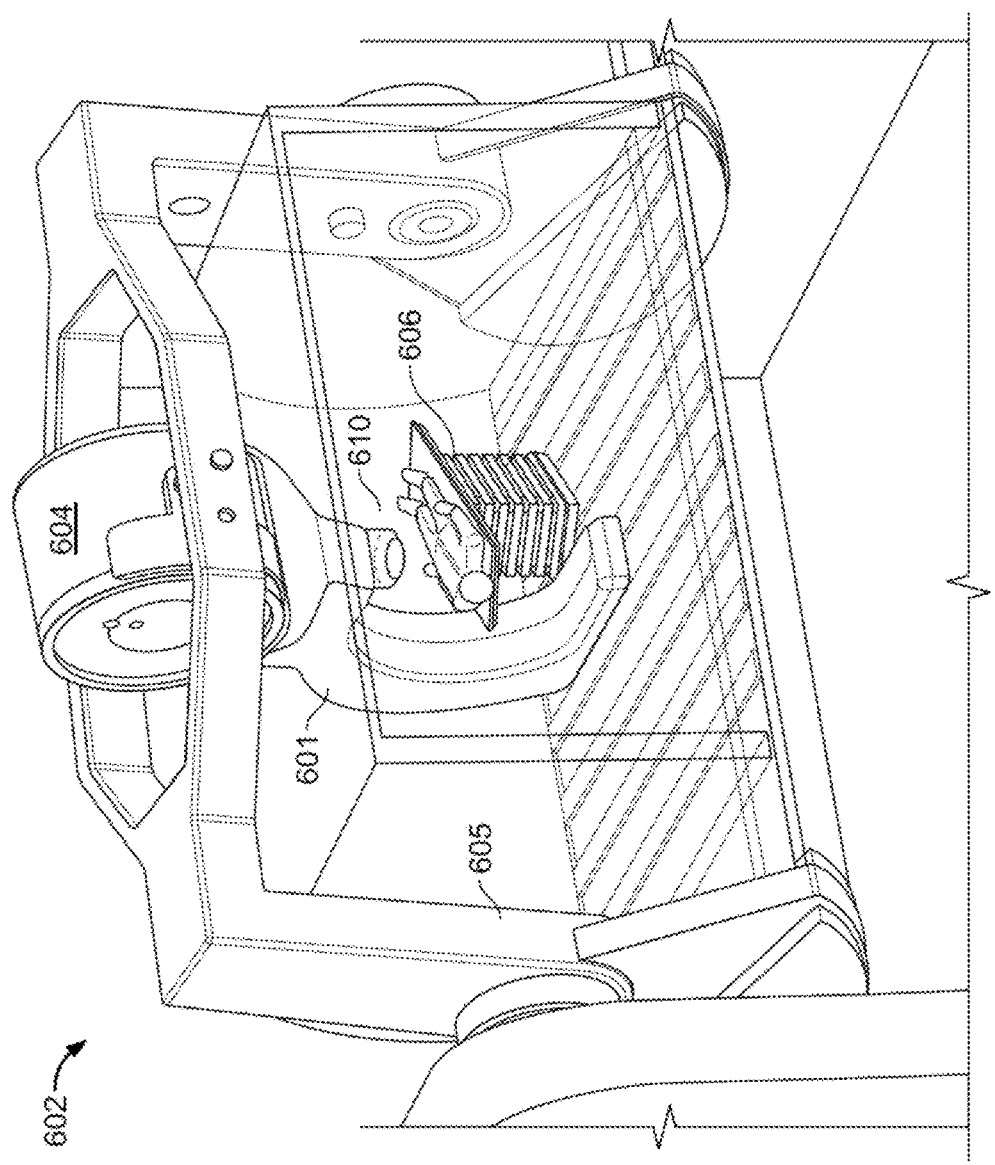
FIG. 14 shows a patient positioned within an example inner gantry in an example treatment room.

In system 602 of FIG. 14, a beam-producing particle accelerator of the type described herein, in this case synchrocyclotron 604, is mounted on rotating gantry 605. Rotating gantry 605 is of the type described herein, and can angularly rotate around patient support 606. This feature enables synchrocyclotron 604 to provide a particle beam directly to the patient from various angles. For example, as in FIG. 14, if synchrocyclotron 604 is above patient support 606, the particle beam may be directed downwards toward the patient. Alternatively, if synchrocyclotron 604 is below patient support 606, the particle beam may be directed upwards toward the patient. The particle beam is applied directly to the patient in the sense that an intermediary beam routing mechanism is not required. A routing mechanism, in this context, is different from a shaping or sizing mechanism in that a shaping or sizing mechanism does not re-route the beam, but rather sizes and/or shapes the beam while maintaining the same general trajectory of the beam.

Figure 15:
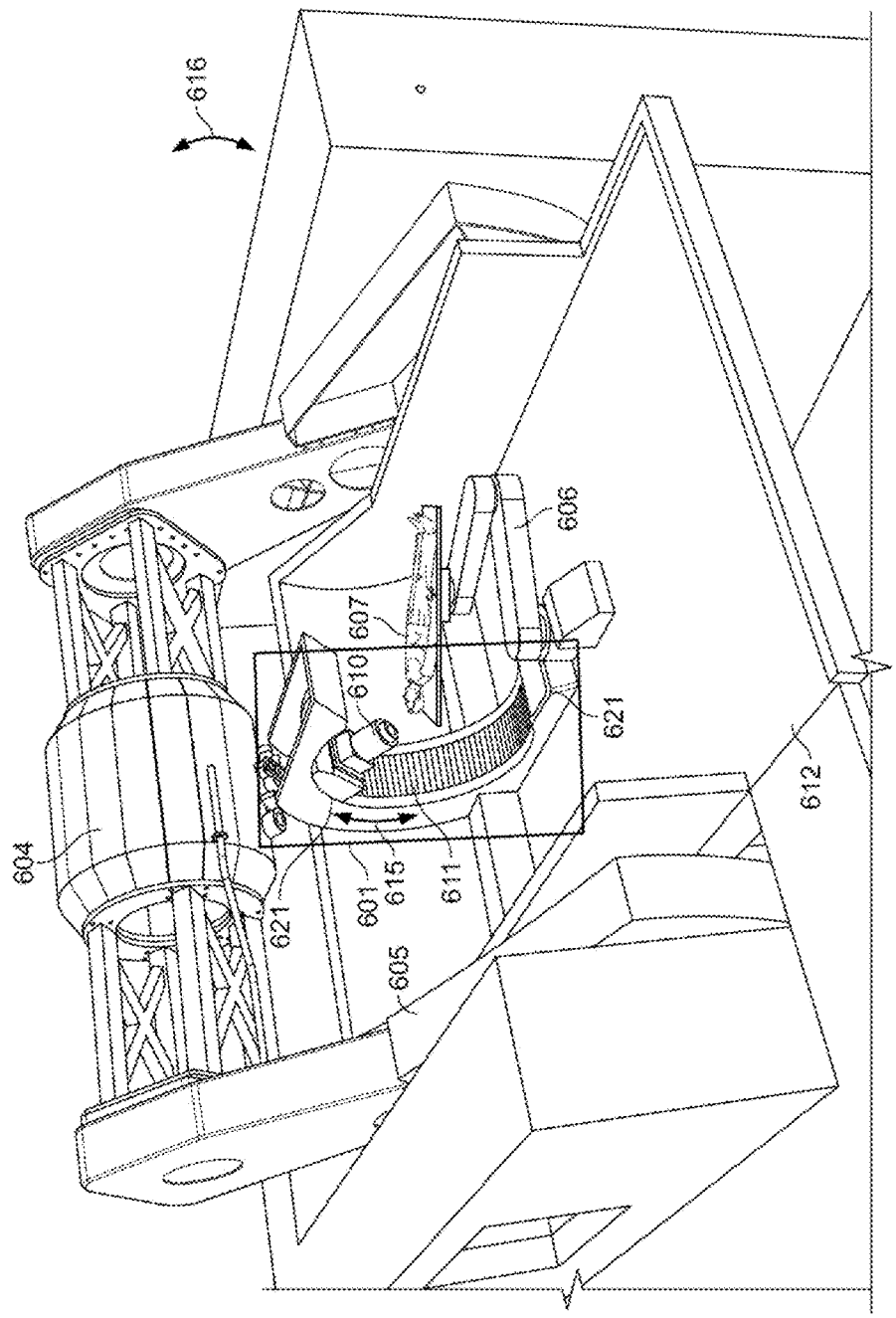
FIG. 15 is a perspective view showing example outer and inner gantries positioned to apply a proton or ion beam from above the patient.
Figure 16:
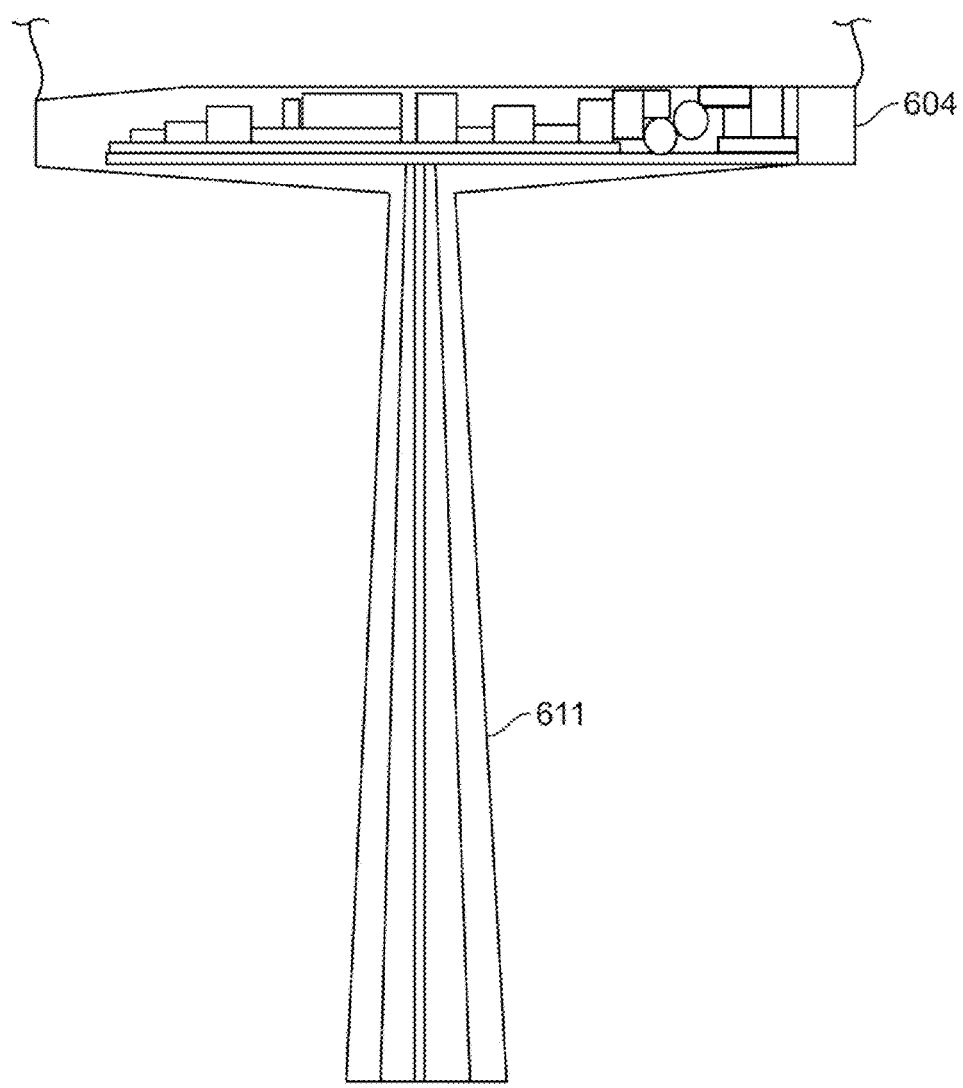
FIG. 16 shows the shape of a particle beam provided by an example accelerator.

Referring also to FIG. 15, an inner gantry 601 may be included system 602. In this example, inner gantry 601 is roughly C-shaped, as shown. Inner gantry 601 includes an applicator 610. Applicator 610 is mounted in a manner that permits applicator 610 to move along the surface 611 of inner gantry 601 relative to patient support 606 (which is a different type of support than that depicted in FIG. 12). This enables the applicator to be positioned anywhere within, e.g., a half-circle around the patient, e.g., anywhere above, alongside, or below the patient 607. Applicator 610 may alter the particle beam provided by synchrocyclotron 604. More specifically, as shown in FIG. 16, the particle beam 611 provided by the beam shaping system of synchrocyclotron 604 may diverge the further the particle beam gets from the output of synchrocyclotron 604. Applicator 610 may receive the particle beam from the output of synchrocyclotron 604 and alter characteristics of the particle beam. For example, applicator 610 may include an aperture and/or other beam-focusing mechanisms to substantially collimate the particle beam. As a result, the particle beam can be more precisely applied to a target in the patient. For example, the particle beam can be sized and/or shaped to treat tumors of specific sizes and/or shapes. In this regard, applicator 610 is not limited to collimating the particle beam. For example, applicator 610 may reduce the size of the particle beam while also collimating the beam. The applicator may be a multi-leaf collimator for sizing and/or shaping the particle beam. Applicator 610 may also simply allow the particle beam to pass without alteration. Applicator 610 may be computer controlled to affect the size and/or shape of the beam, as desired.

Figure 17:
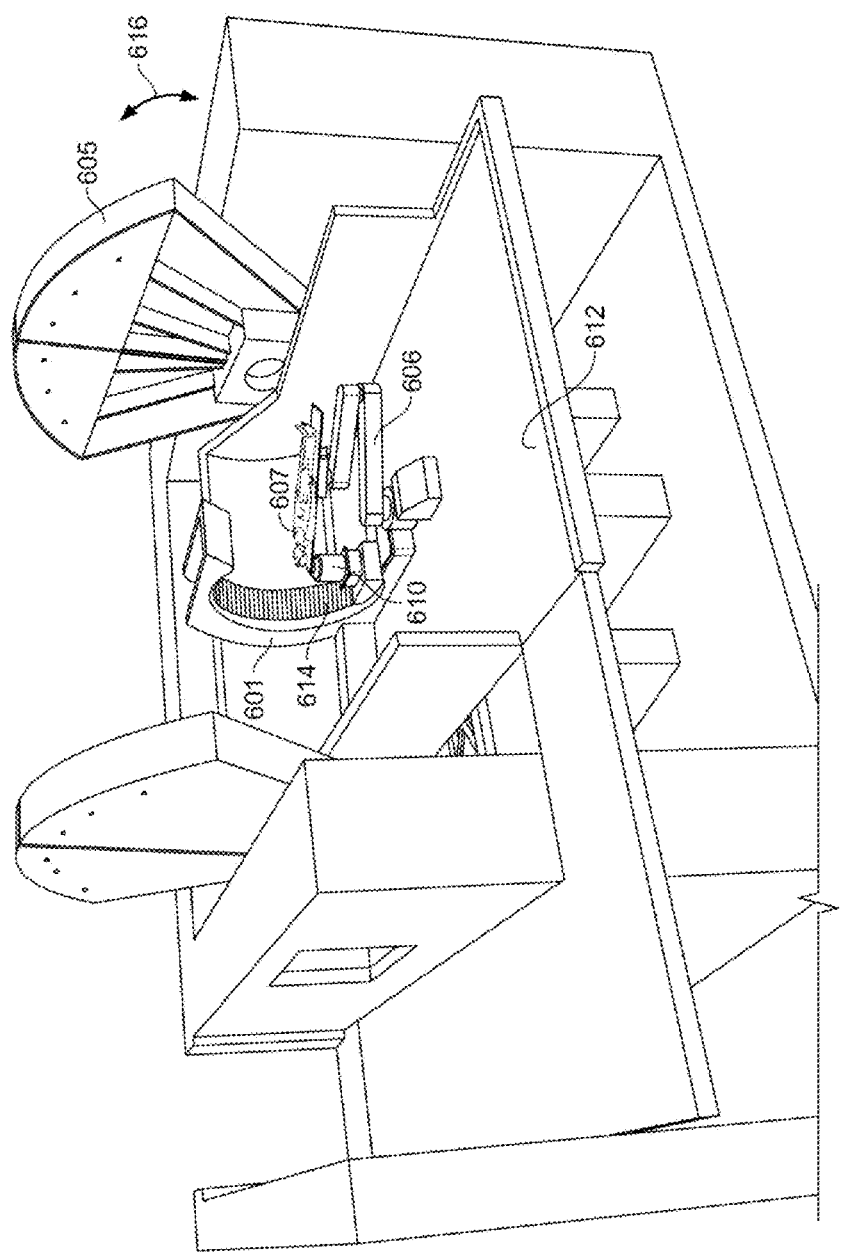
FIG. 17 is a perspective view showing example outer and inner gantries positioned to apply a proton or ion beam from above below the patient.

Applicator 610 and synchrocyclotron 604 may move relative to patient support 606 (and thus the patient) and relative to one another. For example, movement of applicator 610 may substantially coincide with rotation of gantry 605, or one may follow the other, so that the output of synchrocyclotron 604 aligns to the input of applicator 610. FIGS. 15 and 17 illustrate movement of gantry 605 and movement of applicator 610 along inner gantry 601. More specifically, FIG. 17 shows a case where gantry 605 is rotated such that synchrocyclotron 604 is in a vault below patient support 606. In FIG. 17, synchrocyclotron 604 is below the floor 612 of the treatment room, which floor may be made of concrete. Therefore, synchrocyclotron 604 is not visible in FIG. 17. In this case, applicator 610 is moved along inner gantry 601 so that applicator 610 aligns to the output of synchrocyclotron 604. Because synchrocyclotron 604 is not shown in FIG. 17, this alignment is not visible. Nevertheless, a particle beam output from synchrocyclotron 604 passes through cover 614 of inner gantry 601 and a corresponding hole in the floor (not shown) and is thereafter is received by applicator 610. Applicator 610 performs any alteration on the particle beam, and passes the particle beam to patient 607.

Gantry 605 (and thus synchrocyclotron 604) is rotatable relative to the patient in the directions of arrow 615. Applicator 610 is movable along inner gantry 601 in the directions of arrow 616. FIG. 15 shows the locations of synchrocyclotron 604 and applicator 610 after the movements depicted by arrows 615 and 616, respectively. In FIG. 15, both synchrocyclotron 604 and applicator 610 are above patient support 606 (and thus above patient 607). In this configuration, synchrocyclotron 604 directs its particle beam downward, toward the patient. Applicator 610 receives the particle beam, alters (e.g., collimates) the particle beam, and passes the resulting particle beam to the patient.

Patient support 606 is movable relative to inner gantry 601, thereby enabling the patient to be moved such that a top part 621 of inner gantry 601 is above the patient, and such that a bottom part 622 of inner gantry 601 is below the patient. Movement of patient support 606, along with movement of gantry 605 and applicator 610, enables relatively precise targeting of tumors and/or other treatment areas on the patient.

Figure 18:
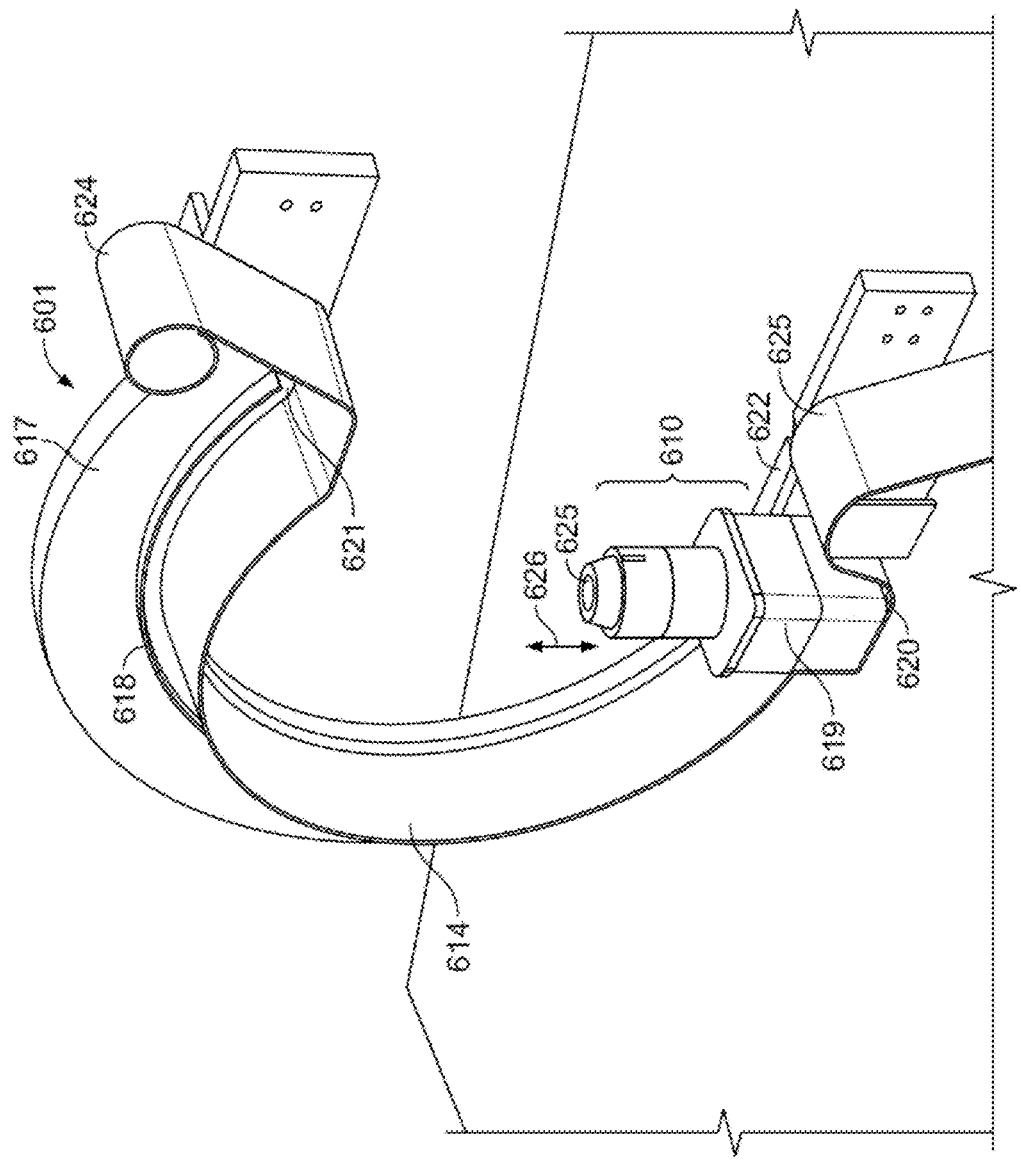
FIG. 18 shows components of an example inner gantry.

FIG. 18 shows an example construction of inner gantry 601. In this example, inner gantry includes a structural weldment 617, a precision linear bearing rail 618 (e.g., a THK rail), cover 614, and applicator 610 that includes an extension drive 619, and a theta drive 620. Inner gantry 601 may include features in addition to those show, substitutions for the features that are shown, or both.

Structural weldment 617 may be constructed of any rigid material, such as metal, plastic, or the like, which is capable of supporting the weight of applicator 610. In this example, structural weldment 617 is substantially C-shaped (thereby defining the shape of inner gantry 601). It is noted, however, that structural weldment 617 may have other shapes. For example, it may be elongated or compressed. Basically, structural weldment may have any shape that enables relatively unobstructed, continuous travel of applicator 610 between positions that are above and below the patient.

Structural weldment 617 includes one or more bearing rails 618. The number of rails that may be used depends upon the connection required to applicator 610. Applicator 610 moves along bearing rail 618 between a top part 621 of structural weldment 617 and a bottom part 622 of structural weldment 617. The movement may be continuous or in discrete increments and may be stopped at any point along bearing rail 618 in order to obtain a desired position of applicator 610 relative to the position of the patient.

Cover 614 covers what would otherwise be an open hole to the area below floor 612 (see FIG. 17). The hole and cover allow a particle beam to pass from the synchrocyclotron to the applicator. Cover 614, however, prevents objects and/or other material from falling through that hole and possibly damaging sensitive equipment, such as the synchrocyclotron. Cover 614 may assist in, or control, movement of applicator 610 along bearing rail 618. That is, cover 614 may roll along a path between the top part 621 and the bottom part 622 of structural weldment 617. Cover 614 may roll-up at its ends 624 and/or 625, as shown in FIG. 18.

Applicator 610 includes extension drive 619 and theta drive 620. Extension drive 619 moves aperture 625 towards, and away from, the patent, e.g., along arrow 626. By virtue of this movement, extension drive may modify the projection of the aperture 625 on the patient. For example, the size of the aperture may be increased or decreased. The shape of the aperture may be altered as well, e.g., between a circular shape, an oval shape, a polygonal shape, etc. Theta drive 620 moves applicator 610 along rail 618 between top part 621 and bottom part 622 of structural weldment 617. Cover 614 may travel along with applicator 610.

All or part of extension drive 619 and theta drive 620 may be computer-controlled. For example, extension drive 619 and/or theta drive 620 may be controlled by the same hardware and/or software that is used to control gantry 605.

The aperture described herein may be controlled so that its size and/or shape is modified. For example, the size of the aperture may be increased or decreased. The shape of the aperture may be altered as well, e.g., between a circular shape, an oval shape, a polygonal shape, etc.

An aperture, such as those described above, may be positioned and/or controlled manually. For example, a stand (not shown) may be used to hold the aperture. The aperture may be sized and/or shaped and placed on the stand. Both the stand and the aperture may be positioned relative to the patent and in line with the particle beam provided by the synchrocyclotron. Any mechanism to hold the aperture may be used. In some implementations, the aperture and/or device used to hold the aperture may be mounted to the synchrocyclotron itself.

The inner gantry is advantageous in that it reduces the precision with which the outer gantry must rotate. For example, the inner gantry allows sub-millimeter beam positioning. Because of the additional precision added by the inner gantry, the outer gantry need not provide sub-millimeter precision, but rather its precision may be at, or greater than, a millimeter. The outer gantry also need not be as large as would otherwise be required in order to obtain high levels of precision.

Additional information concerning the design of the particle accelerator described herein can be found in U.S. Provisional Application No. 60/760,788, entitled "High-Field Superconducting Synchrocyclotron" and filed Jan. 20, 2006; U.S. patent application Ser. No. 11/463,402, entitled "Magnet Structure For Particle Acceleration" and filed Aug. 9, 2006; and U.S. Provisional Application No. 60/850,565, entitled "Cryogenic Vacuum Break Pneumatic Thermal Coupler" and filed Oct. 10, 2006, all of which are incorporated herein by reference.

Further details regarding an example implementation of the foregoing system may be found in U.S. Pat. No. 7,728,311, filed on Nov. 16, 2006 and entitled "Charged Particle Radiation Therapy". The contents of U.S. Pat. No. 7,728,311 are hereby incorporated by reference into this disclosure. In some implementations, the synchrocyclotron may be a variable-energy device, such as that described in U.S. patent application Ser. No. 13/916,401, filed on Jun. 12, 2013, the contents of which are incorporated herein by reference.

Example Implementations

Referring to FIG. 3, particle source 90 is deployed near to the magnetic center of synchrocyclotron 10 so that particles are present at the synchrocyclotron mid-plane, where they can be acted upon by the RF voltage field. As noted above, the particle source may have a Penning ion gauge (PIG) geometry. In the PIG geometry, two high voltage cathodes are placed about opposite each other so that they are aligned linearly. For example, one cathode may be on one side of the acceleration region and one cathode may be on the other side of the acceleration region and in line with the magnetic field lines. A gas tube 101 extends toward the acceleration region proximate to the particle source. When a relatively small amount of a gas (e.g., hydrogen/$H_2$) occupies a region in the tube between the cathodes, a plasma column may be formed from the gas by applying a voltage to the cathodes. The applied voltage causes electrons to stream along the magnetic field lines, essentially parallel to the tube walls, and to ionize gas molecules that are concentrated inside the tube. The background magnetic field reduces scattering of the ionized gas particles and creates a plasma column between the cathodes.

Figure 19:
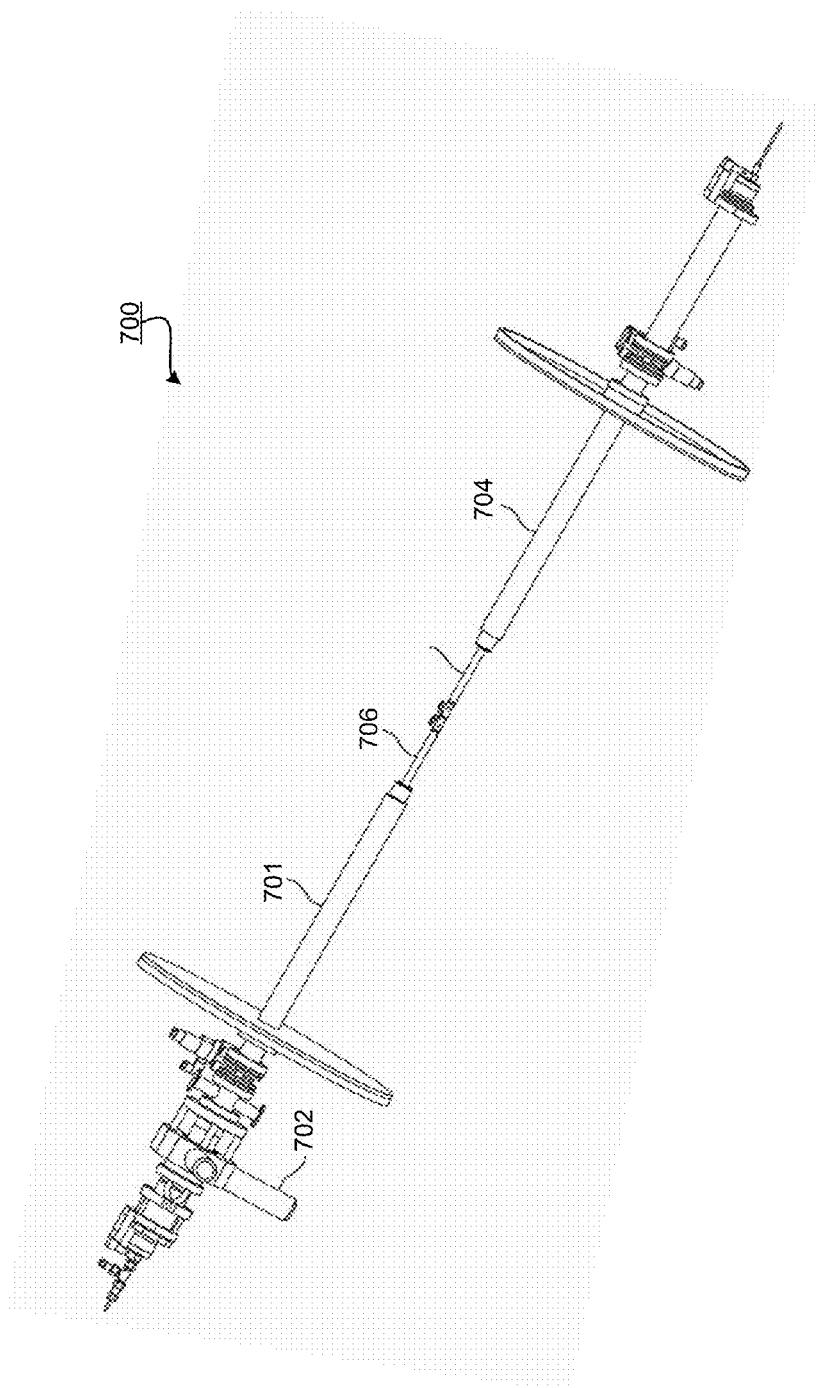
FIG. 19 is a side view of an example particle source.
Figure 20:
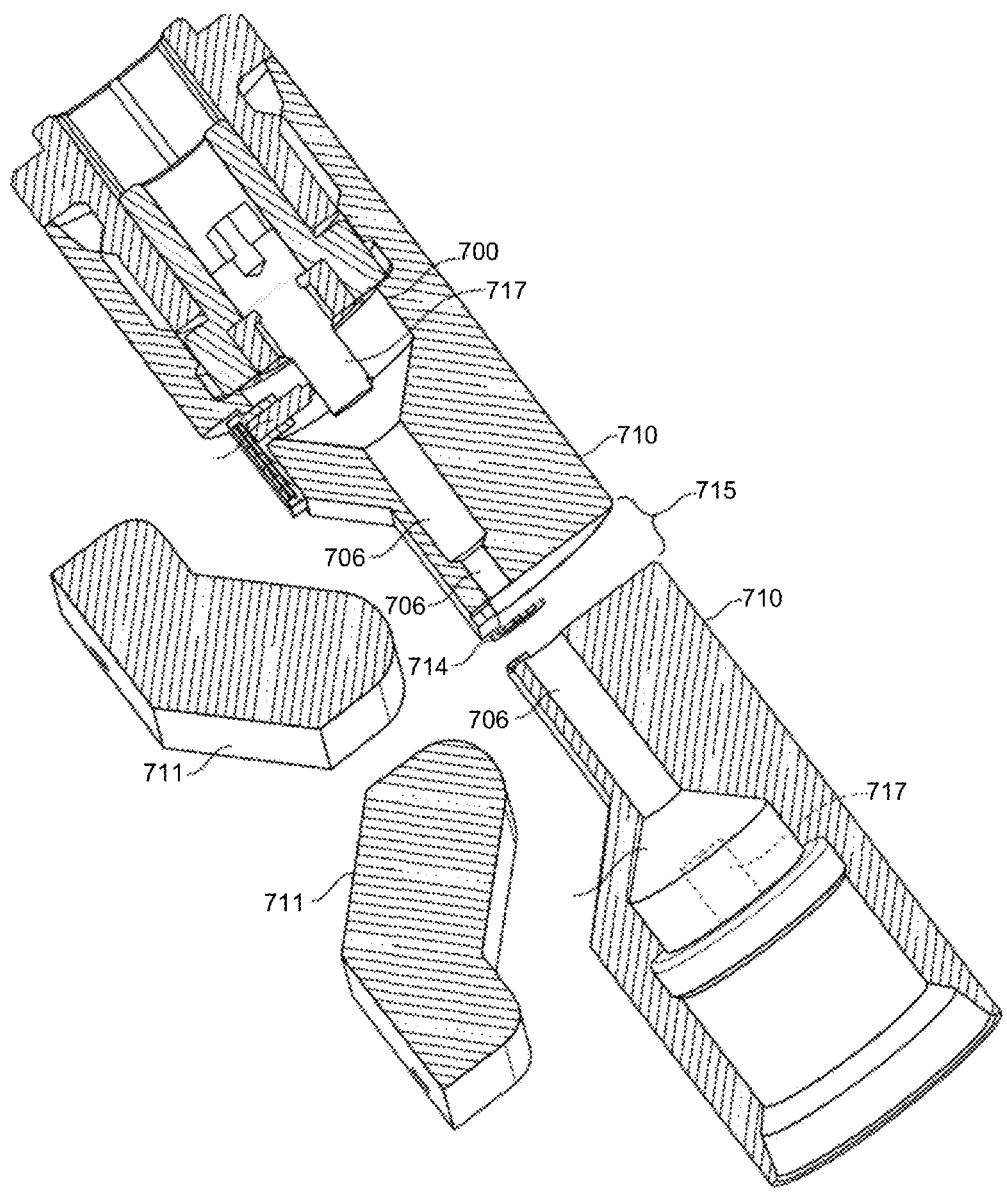
FIG. 20 is a cut-away side view of an example particle source shown relative to a dummy dee.

An example of a PIG geometry particle source 700 that may be used in synchrocyclotron 10 is shown in FIGS. 19 and 20. Referring to FIG. 20, particle source 700 includes an emitter side 701 containing a gas feed 702 for receiving gas (e.g., hydrogen ($H_2$), and a reflector side 704. A housing, or tube, 706 holds the gas. FIG. 16 shows particle source 700 passing through dummy dee 710 and adjacent to active (RF) dee 711. In operation, the magnetic field between active dee 711 and dummy dee 710 causes particles (e.g., protons) to accelerate outwardly. The acceleration is spiral to create orbits about the plasma column, with the particle-to-plasma-column radius progressively increasing. The radii of curvature of the spirals depend on a particle's mass, energy imparted to the particle by the RF field, and a strength of the magnetic field.

When the magnetic field is high, it can become difficult to impart enough energy to a particle so that it has a large enough radius of curvature to clear the physical housing of the particle source on its initial turn(s) during acceleration. The magnetic field is relatively high in the region of the particle source, e.g., on the order of 2 Tesla (T) or more (e.g., 4 T, 5 T, 6 T, 8 T, 8.8 T, 8.9 T, 9 T, 10.5 T, or more). As a result of this relatively high magnetic field, the initial particle-to-ion-source radius is relatively small for low energy particles, where low energy particles include particles that are first drawn from the plasma column. For example, such a radius may be on the order of 1 mm. Because the radii are so small, at least initially, some particles may come into contact with the particle source's housing area, thereby preventing further outward acceleration of such particles. Accordingly, the housing of particle source 700 is interrupted, or separated to form two parts, as shown in FIG. 20. That is, a portion of the particle source's housing may be entirely removed at the acceleration region 714, e.g., at about the point where the particles are to be drawn from the particle source. This interruption is labeled 715 in FIG. 20. The housing may also be removed for distances above, and below, the acceleration region. In an alternative implementation, a substantial portion (e.g., 30%, 40%, 50% or more), but not all, of the PIG source housing is removed, leaving the plasma beam partly exposed. Thus, portions of the PIG housing are separated from their counterpart portions, but there is not complete separation as was the case above.

In the synchrocyclotron described herein, a particle beam is extracted using a resonant extraction system. That is, the amplitude of radial oscillations of the beam are increased by a magnetic perturbation inside the accelerator, which is in resonance with these oscillations. When a resonant extraction system is used, extraction efficiency is improved by limiting the phase space extent of the internal beam. With attention to the design of the magnetic and RF field generating structures, the phase space extent of the beam at extraction is determined by the phase space extent at the beginning of acceleration (e.g., at emergence from the particle source). As a result, relatively little beam may be lost at the entrance to the extraction channel and background radiation from the accelerator can be reduced.

Cathodes 717 may be "cold" cathodes. A cold cathode may be a cathode that is not heated by an external heat source. Also, the cathodes may be pulsed, meaning that they output plasma burst(s) periodically rather than continuously. The duration during which a plasma burst is output is referred to herein as the ion (or particle) source pulse width. When the cathodes are cold, and are pulsed, the cathodes are less subject to wear and can therefore last relatively long. Furthermore, pulsing the cathodes can eliminate the need to water-cool the cathodes. In one implementation, cathodes 717 pulse at a relatively high voltage, e.g., about 1 kV to about 4 kV, and moderate peak cathode discharge currents of about 50 mA to about 200 mA at a duty cycle between about 0.1% and about 1% or 2% at repetition rates between about 200 Hz to about 1 KHz. However, the particle source is not limited to these values.

Figure 21:
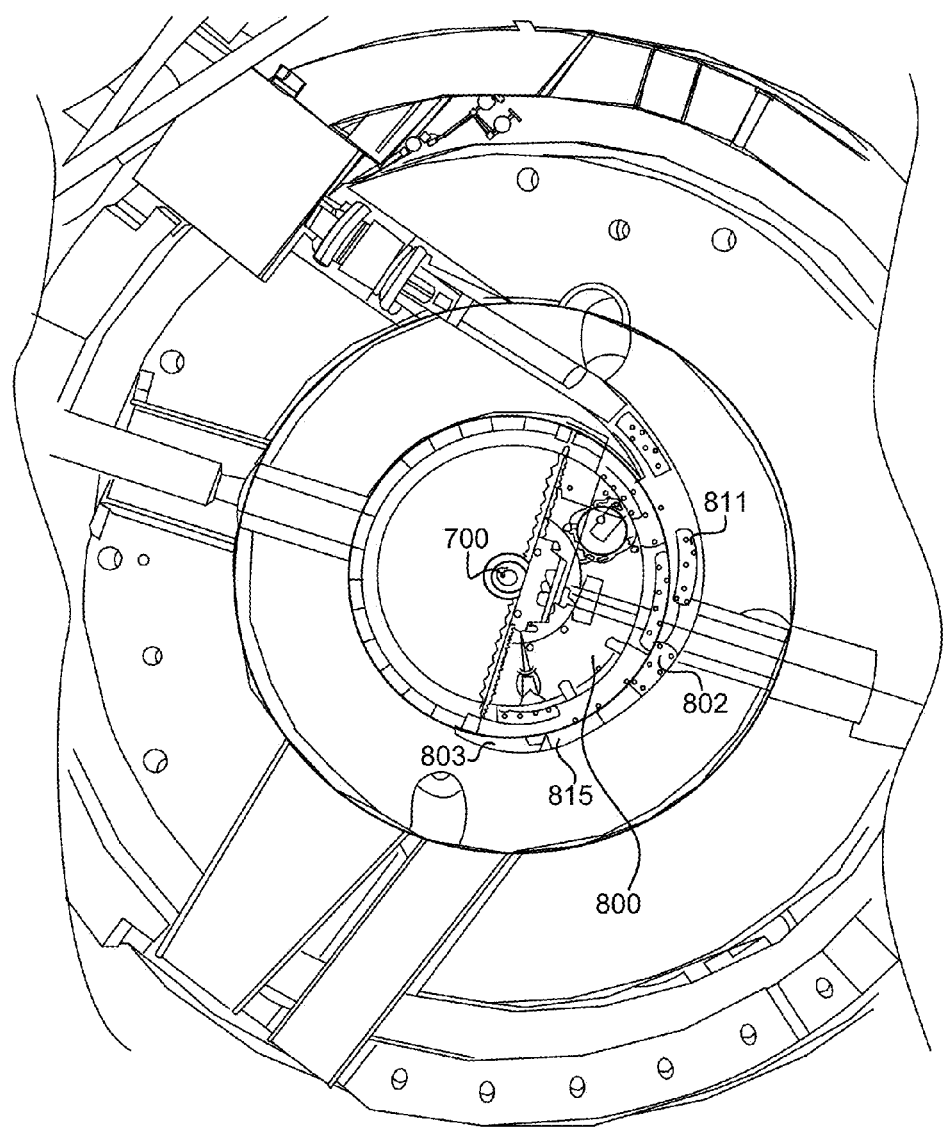
FIG. 21 is a top view of an acceleration cavity and extraction channel

FIG. 21 shows a top view of a portion of a cavity 800 in which particles are accelerated orbitally (e.g., in outward spiral orbits) from particle source 700, which may be as described above. The charged particles accelerate outwardly in orbits toward, and eventually reaching, magnetic regenerator 802. In this example implementation, regenerator 802 is a ferromagnetic structure made, e.g., of steel, iron, or any other type of ferromagnetic material. Regenerator 802 alters the background magnetic field that causes the outward orbital acceleration. In this example, regenerator 802 augments that magnetic field (e.g., it provides a bump in the field). The bump in the background magnetic field affects the particle orbits in a way that causes the orbits to move outwardly towards extraction channel 803. Eventually, the orbits enter extraction channel 803, from which they exit.

Figure 22:
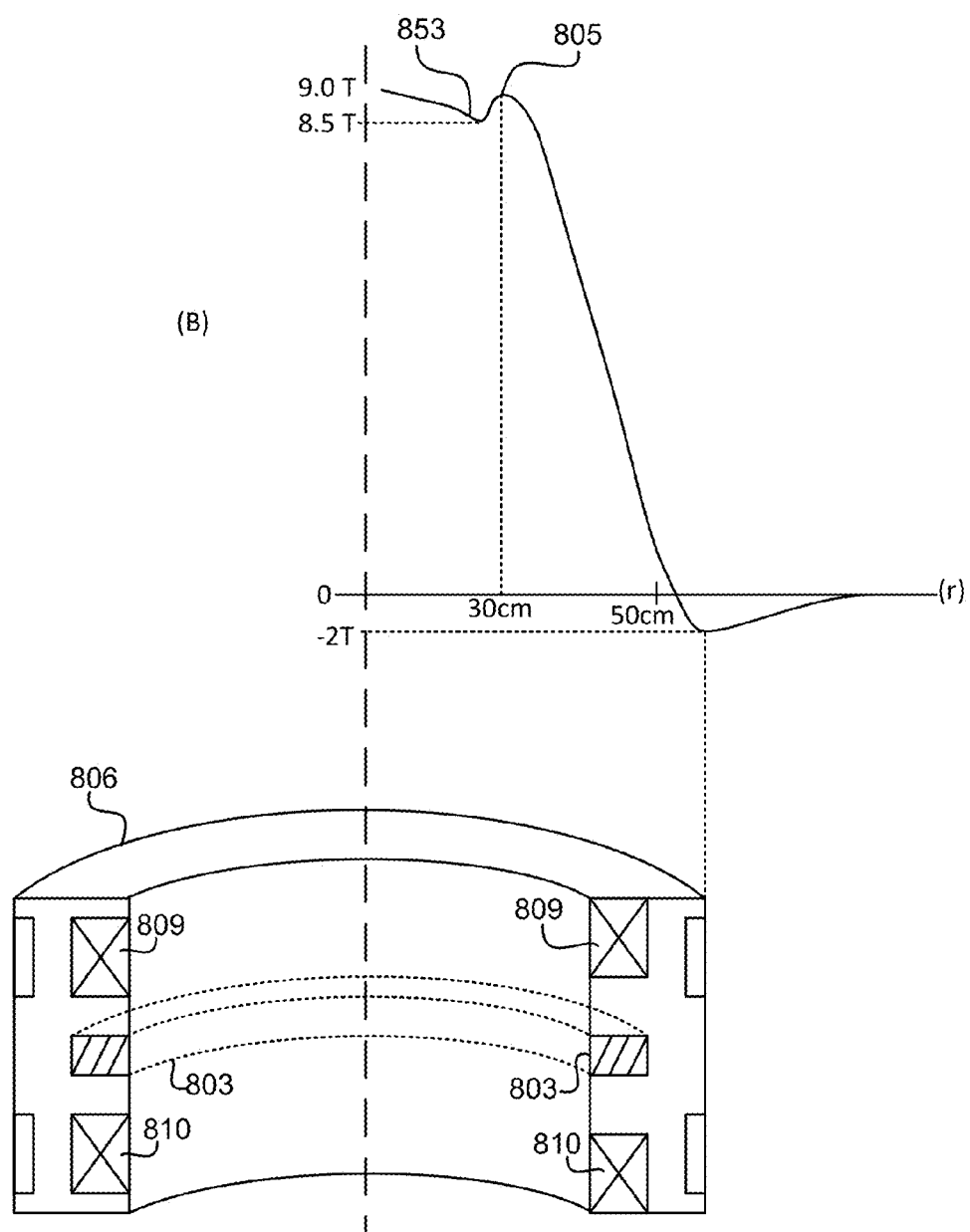
FIG. 22 is a graph showing magnetic field strength versus radial distance from a plasma column, along with a cross-section of an example part of a cryostat of a superconducting magnet.

In more detail, a particle beam orbit approaches and interacts with regenerator 802. As a result of the increased magnetic field, the particle beam turns a bit more there and, instead of being circular, it precesses to the extraction channel. FIG. 22 shows the magnetic field (B) plotted against the radius (r) relative to the particle source 700. As shown in FIG. 22, in this example, B varies from about 9 Tesla (T) to about −2 T. The 9 T occurs at about the center of cavity 800. The polarity of the magnetic field changes after the magnetic field crosses the superconducting coil, resulting in about −2 T on the exterior of the coil, eventually fading to about zero. The magnetic field bump 805 occurs at the point of the regenerator. FIG. 22 also shows the magnetic field plot relative to a cross-section of a bobbin 806 having extraction channel 803 between two superconducting coils 809, 810.

Figure 23:
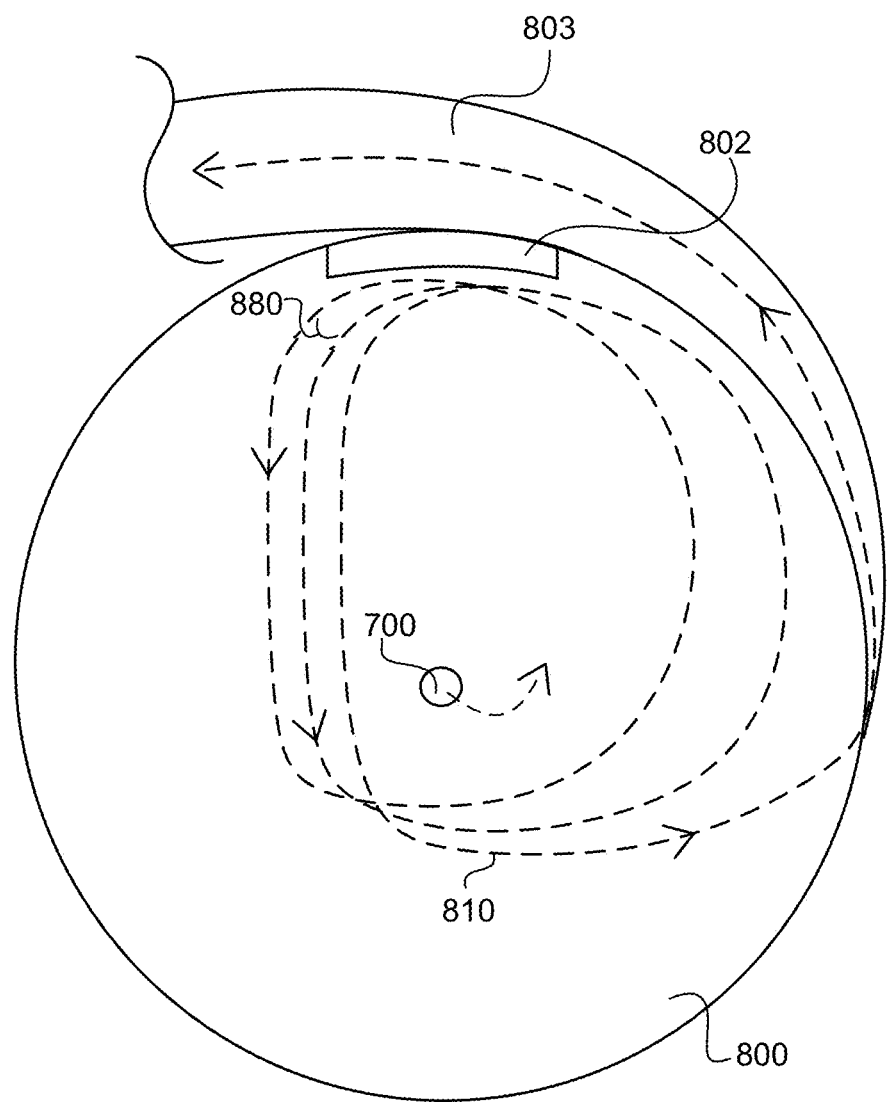
FIG. 23 is a top view of an example acceleration cavity and extraction channel, which depicts orbits moving to enter the extraction channel.

Referring to FIG. 23, regenerator 802 causes changes in the angle and pitch of orbits 810 so that they move toward extraction channel 803. At the point of the extraction channel, the magnetic field strength is sufficiently low to enable the particle beam to enter the extraction channel and to proceed therethrough. Referring back to FIG. 21, extraction channel 803 contains various magnetic structures 811 for adding and/or subtracting dipole fields to direct the entering particle beam through extraction channel 803, to beam shaping elements.

In order to reach the exit point, the particle beam should have the appropriate amount of energy. The amount of energy required to reach that point may vary based, e.g., on the size of the accelerator and the length of the extraction channel (in this example, the extraction channel is about 1.7 or 2 meters in length). In this regard, at least part of extraction channel 803 is above the superconducting coil. As such, the magnetic field in the extraction channel changes little in response to accelerator rotation. Accordingly, the amount of energy needed for a particle beam to traverse the extraction channel does not change appreciably in response to the rotation of the particle accelerator.

Figure 24:
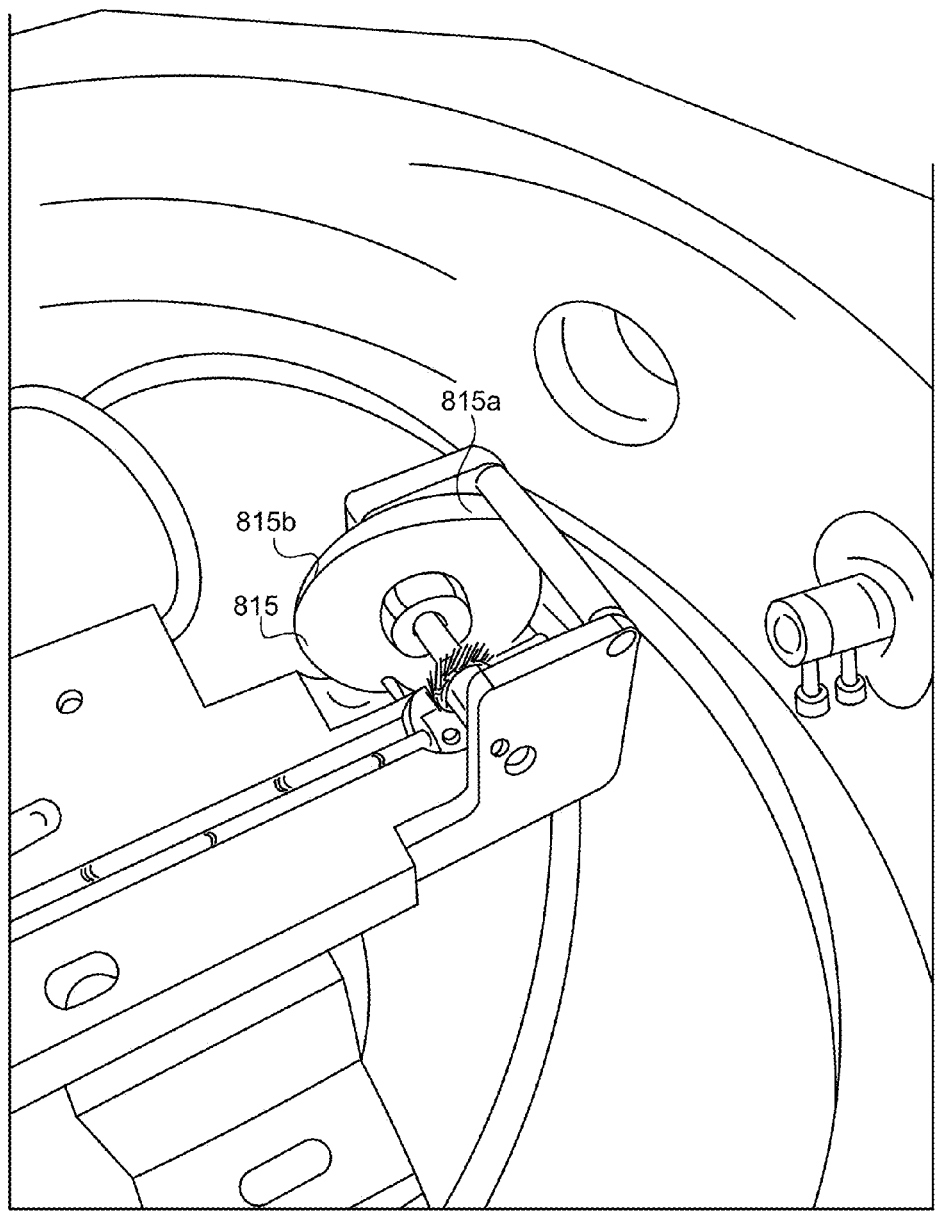
FIG. 24 is a perspective view of an example structure used to change the energy of a particle beam in the extraction channel.
Figure 25:
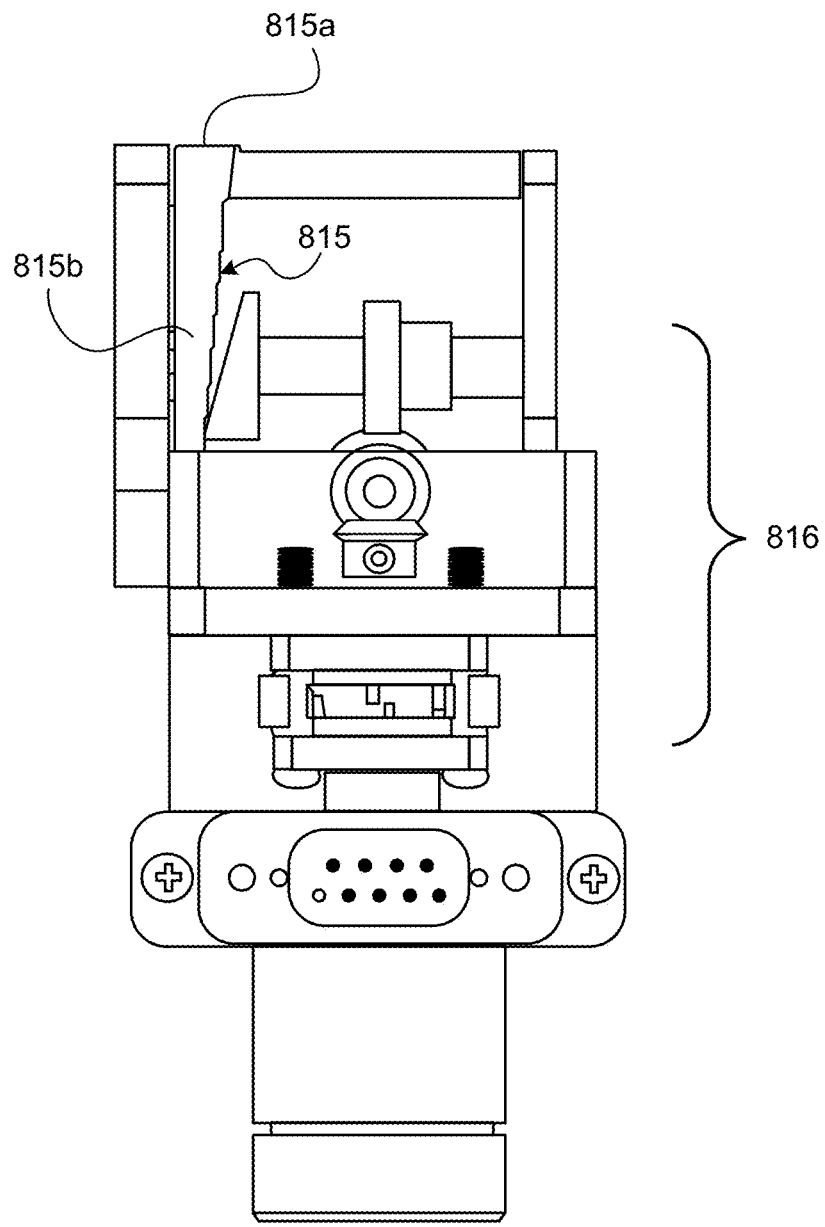
FIG. 25 is a side view of the structure of FIG. 24.

The superconducting coil moves during rotation of the gantry. Orbits that are affected by regenerator 802 change due to gravitational movement of the coil. This movement can be as little as tenths of millimeters. Nevertheless, as a result, the energy of the particle beam that enters the extraction channel may be different from the energy required to traverse the entire channel. To adjust for this change in the energy of particles entering the extraction channel, a structure 815 may be placed inside, or at the entry point to, extraction channel 803. The structure may be used to absorb excess energy in the particle beam. In this example, structure 815 is a rotatable, variable-thickness wedge, which may have a wheel-like shape. An example of structure 815 is shown in FIGS. 24 and 25. As shown in these figures, structure 815 may have continuously varying thickness. Alternatively, the thicknesses may vary step-wise.

The structure may be moved (e.g., rotated) to absorb an appropriate amount of energy from a particle beam in/entering the extraction channel. In this implementation, thicker parts 815a of the structure absorb more energy than thinner parts 815b. Accordingly, the structure may be moved (e.g., rotated) to absorb different amounts of energy in a particle beam. In some implementations, the structure may have a part containing no material (e.g., a "zero" thickness), which allows the particle beam to pass unaltered. Alternatively, in such cases, the structure may be moved entirely or partly out of the beam path. In some implementations, the maximum thickness may be on the order of centimeters; however, the maximum thickness will vary from system-to-system based, e.g., on energy absorbing requirements. FIG. 25 also shows a motor 816 that controls an axle to rotate structure 815, e.g., in response to a detected gantry position.

The structure may be made of any appropriate material that is capable of absorbing energy in a particle beam. As noted above, ideally, the structure minimizes scattering of the particle beam in the extraction channel; however, in practice, there may be amounts of scatter that are present and that are tolerable. As described in more detail below, in some implementations, adjustments may be made to elements of the particle therapy system that account for this scatter. Examples of materials that may be used for the structure include, but are not limited to, beryllium, plastic containing hydrogen, and carbon. These materials may be used alone, in combination, or in combination with other materials.

The movement (e.g., rotation) of the structure may be computer-controlled using a control system that is part of the broader particle therapy system. Computer control may include generating one or more control signals to control movement of mechanical devices, such as actuators and motors that produce the motion. The rotation of structure 815 may be controlled based on a rotational position of the particle accelerator, as measured by the rotational position of the gantry (see, e.g., FIGS. 1, 11 and 12 showing gantry rotation) on which the particle accelerator is mounted. The various parameters used to set the rotational position of the structure vis-à-vis the position of the gantry may be measured empirically, and programmed into the control system computer.

Downstream from (e.g., after) the extraction channel, various devices are used to affect the particle beam output. One such device is configured to spread-out Bragg peaks of the particle beam to achieve a substantially uniform particle beam dose at a range of depths within the patient. As described in wikipedia.org, "[w]hen a fast charged particle moves through matter, it ionizes atoms of the material and deposits a dose along its path. A peak occurs because the interaction cross section increases as the charged particle's energy decreases." "The Bragg peak is a pronounced peak on the Bragg curve which plots the energy loss of ionizing radiation during its travel through matter. For protons . . . the peak occurs immediately before the particles come to rest." FIG. 26 is an example Bragg curve showing a Bragg peak 900 for a particular dose of proton therapy and depth.

Figure 26:
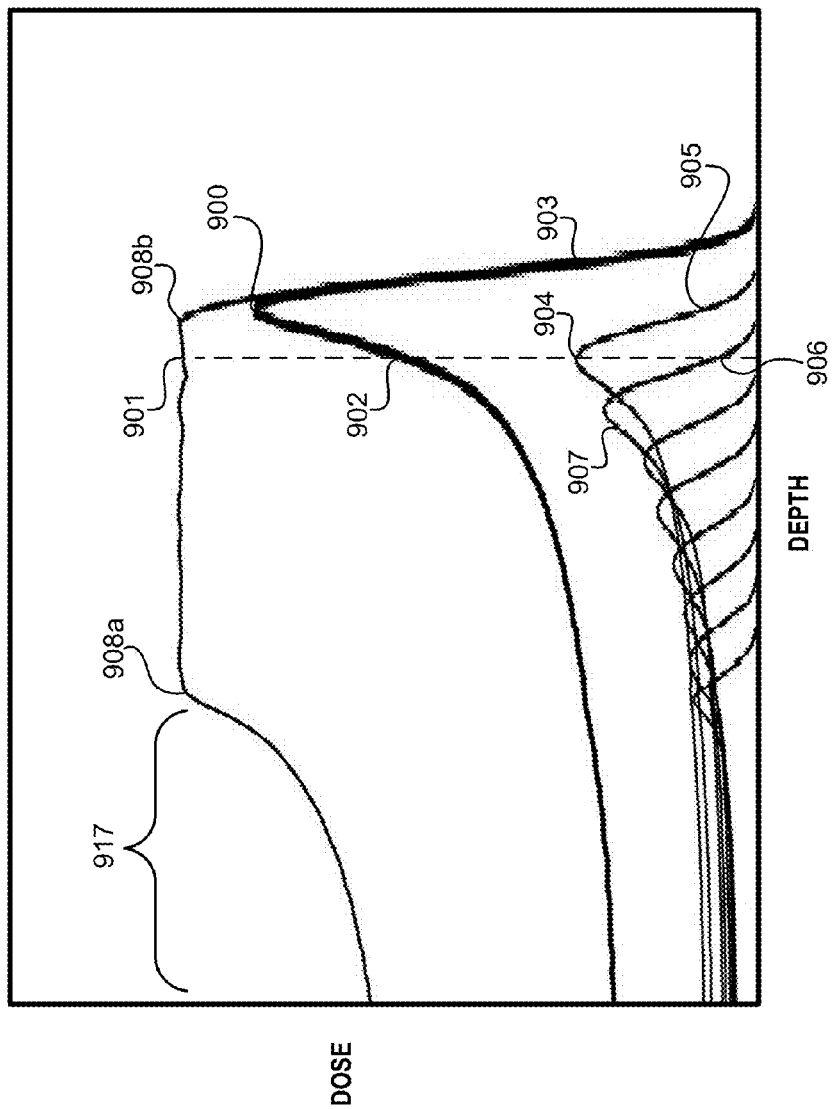
FIG. 26 is a graph showing various Bragg peaks and the cumulative effect that produces a spread-out Bragg peak.

To achieve a relatively uniform dose of particle therapy at a range of depths, a modulator device is configured to move Bragg peaks of the particle beam along the graph of FIG. 26 and to change the intensity of the Bragg peaks at the moved locations. Because particle therapy is cumulative, the resulting dosages may be added to obtain a substantially uniform dose. For example, referring to FIG. 26, the dosage at point 901 is the sum of doses at point 902 on Bragg curve 903, at point 904 on Bragg curve 905, and at point 906 on Bragg curve 907. Ideally, the result is a substantially uniform dose from depths 908a to 908b. This is referred to as a "spread-out Bragg peak", which extends depth-wise into a patient.

In some implementations, the modulator device used to spread-out the Bragg peaks is a structure, such as a modulator wheel, having different thicknesses at different locations along its circumference. Accordingly, the modulator wheel is rotatable relative to the particle beam in order to provide the appropriate particle intensity for a particular depth and area.

Figure 27:
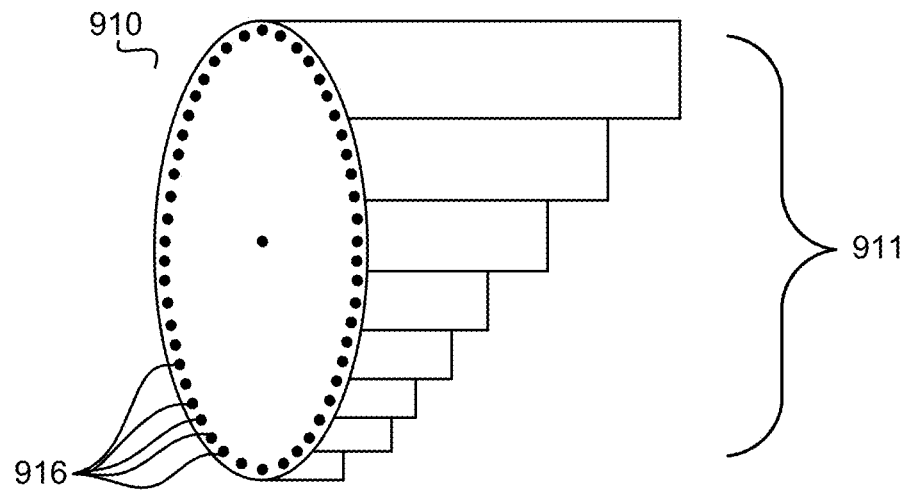
FIG. 27 is a side view of a modulator wheel for producing Bragg peaks at different depths and intensity levels.
Figure 28:
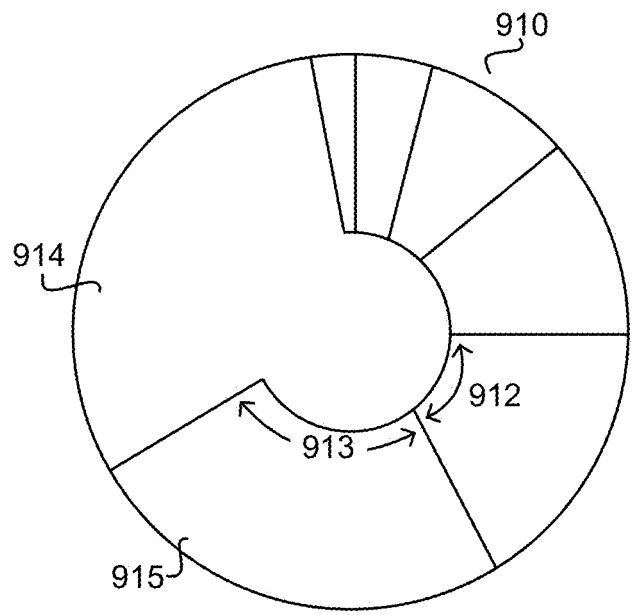
FIG. 28 is a top view of the modulator wheel of FIG. 27.

FIG. 27 shows a perspective view of an example modulator wheel 910 and FIG. 28 shows a top view of modulator wheel 910. As shown in the figures, the modulator wheel has numerous steps 911, each with a different thickness (e.g., varying from zero or substantially zero thickness to a thickness on the order of centimeters or more). The thicknesses are used vary the depth of corresponding Bragg peaks. For example, the least amount of thickness produces a Bragg peak with the most depth, the greatest amount of thickness produces a Bragg peak with the least depth, and so forth. As shown in FIG. 28 the angles (e.g., 912, 913, etc.) of the various steps also vary, resulting in different circumferential lengths for at least some of, and in some cases all of, the steps. The angle of each step adjusts how much the corresponding Bragg peak subtends within the patient. For example, the Bragg peak with the most intensity (e.g., Bragg peak 900 of FIG. 26) is the one that subtends the most. Accordingly, its corresponding step 914 has the largest angular extent. The Bragg peak with the next most intensity (e.g., Bragg peak 904 of FIG. 26) is the one that subtends the next most. Accordingly, its corresponding step 915 has the next largest angular extent; and so forth.

The modulator wheel may have constant, substantially constant, or variable rotation in order to provide the appropriate Bragg peak spreading for a prescription. In some implementations, the particle therapy system may include more than one modulator wheel of the type shown in FIGS. 27 and 28. The modulator wheels may be switchable into, and out of, the beam path in order to achieve a desired particle beam dose at a particular patient depth. For example, a first modulator wheel may be used for a first depth or range of depths (e.g., 10 cm to 15 cm); a second modulator wheel may be used for a second depth or range of depths (e.g., 15 cm to 20 cm); a third modulator wheel may be used for a third depth or range of depths (e.g., 20 cm to 25 cm); and so forth. In some implementations, there may be twelve modulator wheels; however, in other implementations, more or less than twelve modulator wheels may be used. Treatment depth is also dependent upon the particle beam intensity, which is a function of the ion (or particle) source pulse width, as described below.

The modulator wheels may be switchable into, or out of, the beam path, as noted above. For example, the modulator wheels may be movable along a rail, and motor-controlled so that they can be moved into, or out of, the beam path. In other implementations, the rail may be below the beam path, and an appropriate modulator wheel may be positioned proximate the beam path, and thereafter moved into the beam path through another motor or other control system.

The modulator wheels may be designed to provide uniform spread-out Bragg peaks from a maximum depth to the surface of a patient (e.g., to the outer layer of the patient's skin). To customize the depth of dosage, Bragg peaks in undesired locations (e.g., in area 917 in FIG. 26) may be "turned-off". This may be done by turning-off the RF source, turning-off the ion source, or turning-off both at an appropriate time during each rotation of the modulator wheel.

Ion source pulse width also has an effect on spread-out Bragg peak uniformity. As background, the amount of time that a particle source is intermittently (e.g., periodically) activated is varied, thereby providing the plasma column for different periods of time and enabling extraction of different numbers of particles. For example, if the pulse width is increased, the number of particles extracted increases and, if the pulse width decreases, the number of particles extracted decreases. In some implementations, there is a linear relationship between the time that the particle source is on and the intensity of the particle beam. For example, the relationship may be one-to-one plus an offset. In an example implementation, the particle source may be pulsed within a frequency window that occurs during a frequency sweep between a maximum frequency of about 135 MHz and a minimum frequency of about 95 MHz or 90 MHz. For example, the particle source may be pulsed between 132 MHz and 131 MHz for a period of time. In an implementation, this period of time is about 40 μs; however, these values may vary or be different in other implementations. Failing to pulse the particle source outside of the frequency window can inhibit extraction of particles from the plasma column.

Figure 29:
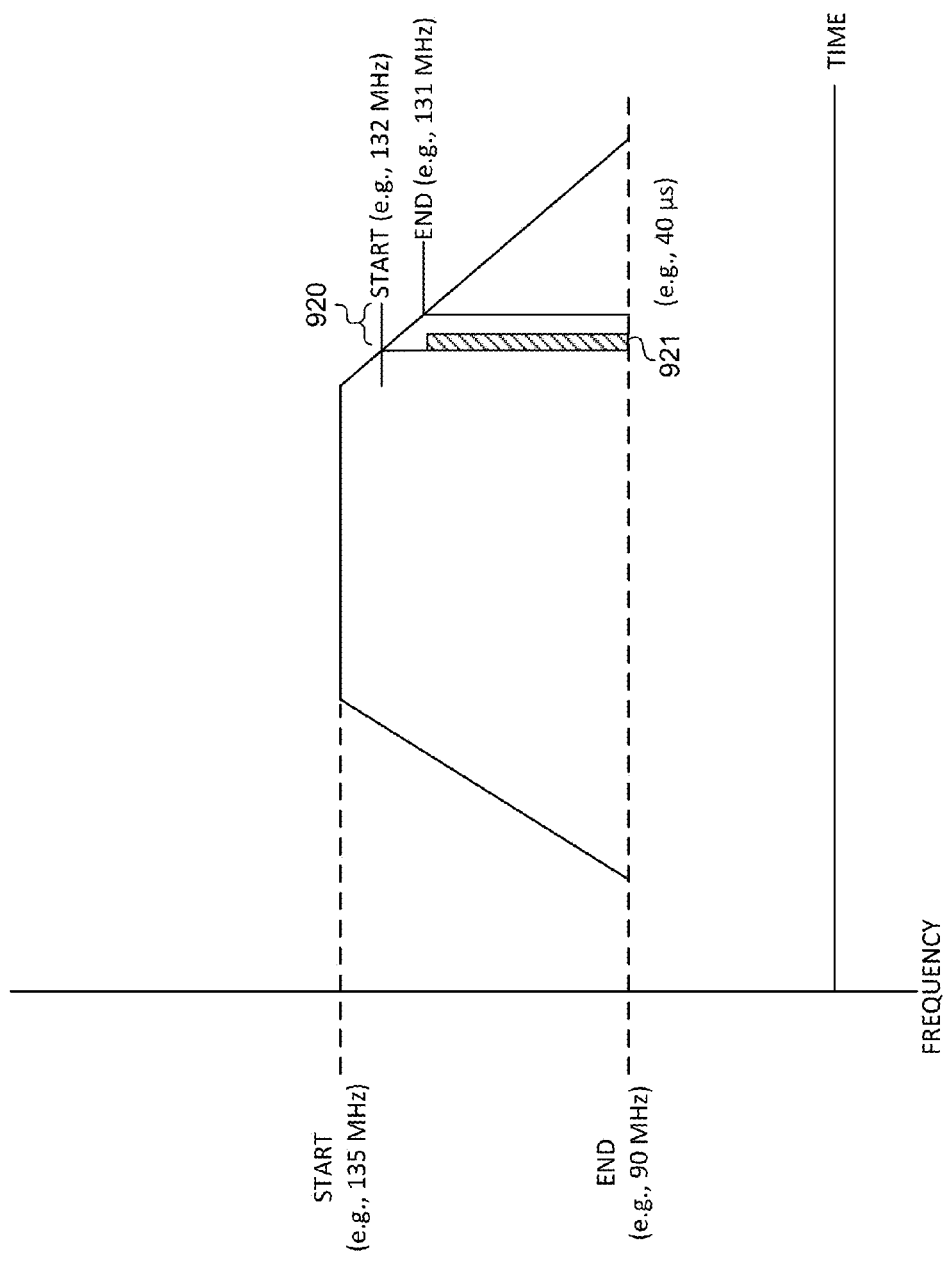
FIG. 29 is a graph showing a frequency sweep and an ion source pulse width output during a period of the frequency sweep.

FIG. 29 is a graph showing the voltage sweep in the resonant cavity over time from a maximum frequency (e.g., 135 MHz) to a minimum frequency (e.g., 90 MHz or 95 MHz). The extraction window 920 occurs, in this example, between 132 MHz and 131 MHz. The width of pulse 921 (the ion source pulse width) may be varied to control the intensity of the particle beam output by the particle accelerator.

Figure 30:
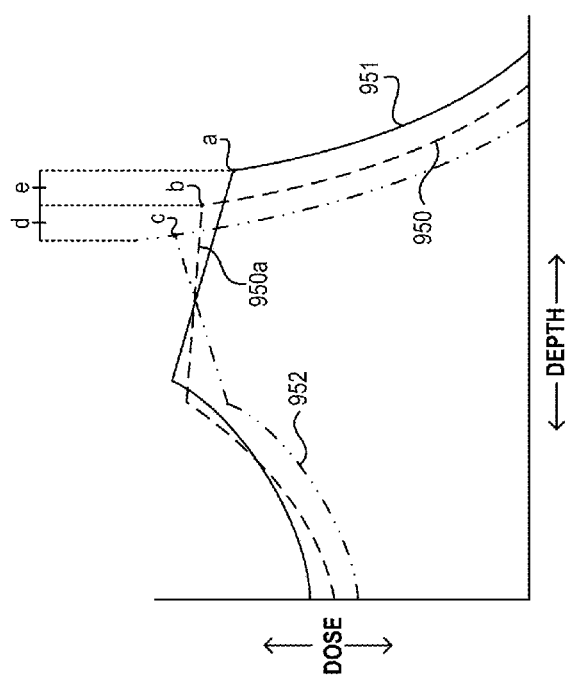
FIG. 30 is a graph showing spread-out Bragg peaks at different depths within a patient.

Ion source pulse widths may be adjustable in order to achieve substantial uniformity in spread-out Bragg peaks. In this regard, various factors, such as particle beam intensity, may contribute to the depth at which Bragg peaks penetrate a patient. A selected modulator wheel can produce different Bragg curves for different depths. For example, FIG. 30 shows Bragg curves for three different depths. Bragg curve 950 is for the nominal (or predefined) depth for a modulator wheel; Bragg curve 951 is for the maximum depth for the modulator wheel; and Bragg curve 952 is for the minimum depth for the modulator wheel. Ideally, the spread-out Bragg peaks should be at about the nominal level regardless of depth.

Figure 31:
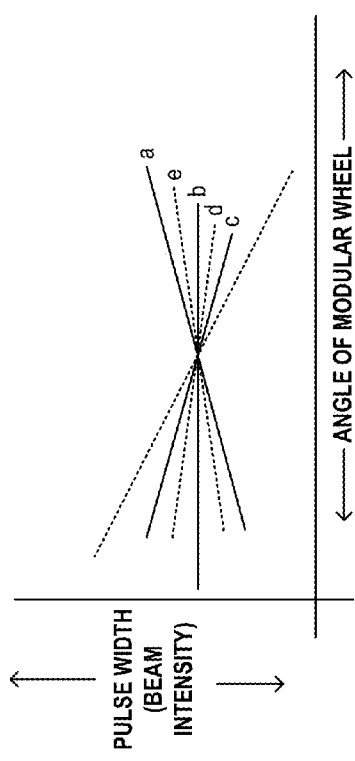
FIG. 31 is a graph showing ion source pulse width relative to the angle of the modulation wheel for the spread-out Bragg peaks of FIG. 30.

As shown in FIG. 30, Bragg curves 951 and 952 have spread-out Bragg peaks that are sloped. For Bragg curve 952, the slope is positive; and for Bragg curve 951 the slope is negative. To more closely approximate the nominal Bragg peak level at point b, the intensity of the particle beam is be increased at point a (to raise the Bragg peak at point a to the level at point b), and the intensity of the particle beam is be decreased at point c (to lower the Bragg peak at point c to the level of point b). The intensity of the particle beam is also be adjusted at points preceding a and c to either raise or lower the Bragg peaks at those points so that they coincide, at least to some degree, with the corresponding level of the nominal Bragg peak. The intensity of the particle beam may be changed by changing the ion source pulse width. However, different points along Bragg curves 951 and 952 require different amounts of adjustment in order to approximate the nominal spread-out Bragg peak of curve 950. Accordingly, in each instance, the pulse widths may be varied based on rotation of the modulator wheel. For example, at a point a when the modulator wheel impacts the particle beam, the pulse width may be increased more than at points preceding a along Bragg curve 951. Similarly, at a point c when the modulator wheel impacts the particle beam, the pulse width may be decreased more than at points preceding c along Bragg curve 952. For example, FIG. 31 is a plot showing the relationship between pulse width and rotational angle of the modulator wheel for Bragg curves 950, 951 and 952. Values have been omitted, since they are case specific.

Variations in pulse-width can be determined by obtaining the appropriate pulse widths at the beginning and ending of a Bragg peak, and linearly interpolating between the two to obtain variations in between. Other processes also may be used, as described below. To increase or decrease an overall dose, all pulse widths may be increased or decreased by a specified factor.

Figure 32:
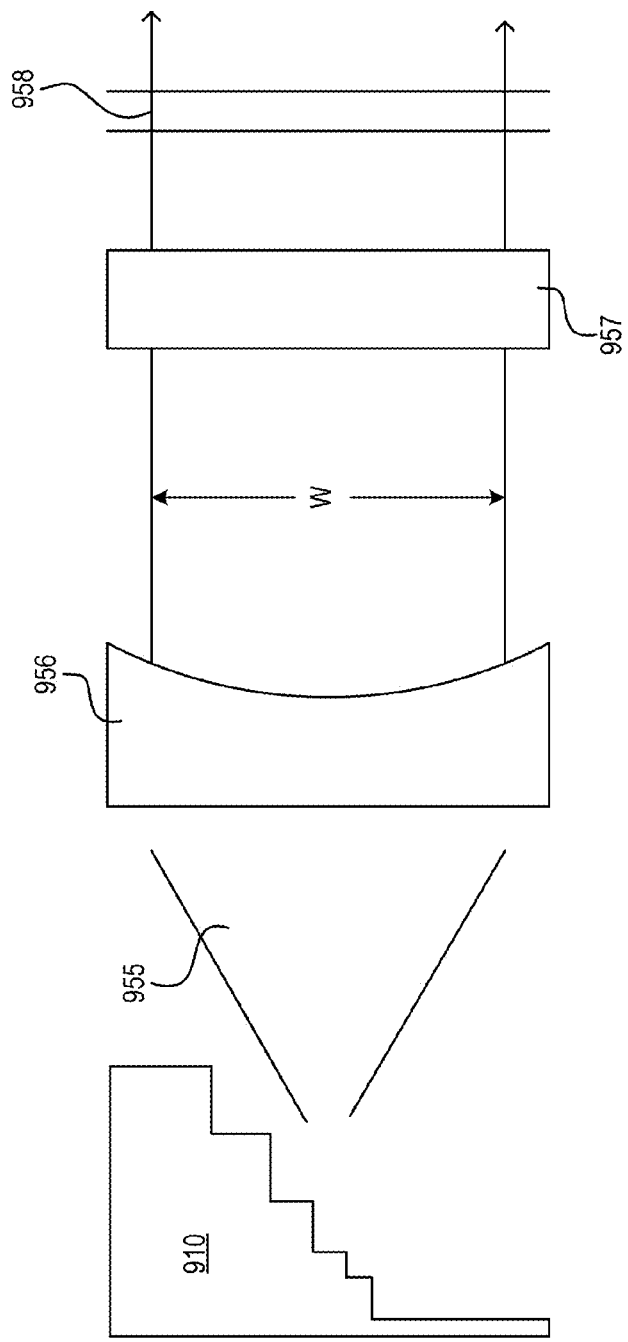
FIG. 32 is a side view showing a beam path that includes the modulator wheel, a scatterer, an absorber and an ionization chamber.

Referring to FIG. 32, the output 955 of modulator wheel 910 is a scattered particle beam having a Gaussian profile (with a majority of particles at the center of the beam). A scatterer 956 is downstream of modulator wheel (e.g., between modulator wheel 910 and the patient position). Scatterer 956 reshapes the particle beam so that the particle beam has a substantially constant width (w). For example, the particle beam may have a circular cross-section. In this implementation, scatterer 956 is a scattering foil, all or part of which may be made of a metal, such as lead. As shown, scatterer 956 has a side that is convex in shape, and includes more lead at its edges than at its center. To achieve a larger field beam size, thicker lead may be used, and vice versa. In this regard, the particle therapy system may include multiple scatterers, which may be switched into, or out of, the path of the particle beam in order to achieve a particle beam field size (cross-sectional area). The scatterers may be switched into, or out of, the path of the particle beam using mechanism such as those described above for switching modulator wheels into, or out of, the path of the particle beam.

An absorber 957 may be arranged proximate to the scatterer and may be used to absorb beam energy, e.g., so as to reduce its penetration depth. The absorber may be made of plastic or other material. For example, if the beam is to penetrate 10 cm less, then 10 cm of plastic may be used. The absorber may be a wheel having different thicknesses. The appropriate thickness can be dialed into the particle beam path based on the depth specified in the prescription. A motor or other mechanism may control the wheel. In other implementations, the particle therapy system may include multiple absorbers, which may be switched into, or out of, the path of the particle beam. The absorbers may be switched into, or out of, the path of the particle beam using mechanism such as those described above for switching modulator wheels into, or out of, the path of the particle beam.

Downstream of absorber 957 is an ionization chamber 958 used for determining a total dose of particles provided during a treatment. In some implementations, the ionization chamber includes parallel planes of conductive material (e.g., gold vapor deposited on Kapton film). In operation, a voltage is applied to the parallel planes. Protons ionize the air between the parallel plates and, as a result, charge accumulates on the parallel plates. The amount of charge is proportional to the amount of protons. When the amount of charge exceeds a certain level, current is output, which triggers a counter. The ionization chamber and counter are calibrated so that a click of the counter corresponds to a specified dose (in grays) of particle beam. A control mechanism (e.g., circuitry, a computing device, or the like) keeps track of the dose based on clicks from the counter. When that dose exceeds a prescribed amount, the particle beam is turned-off (e.g., by turning-off the RF source, turning-off the ion source, or turning-off both).

Figure 33:
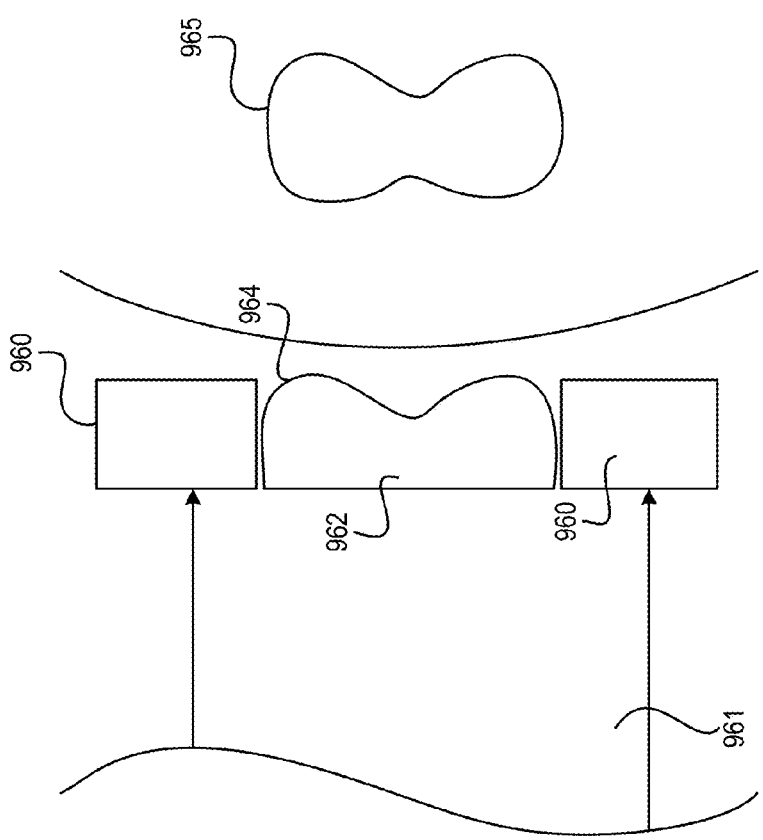
FIG. 33 is a side view of an aperture, a range compensating bolus, and a tumor being treated by a particle beam.

Downstream of ionization chamber 958 is an aperture 960, such as aperture 635 described above. As shown in FIG. 33, aperture 960 limits the extent of the cross-sectional area of particle beam 961 applied to the patient by blocking portions of particle beam outside of a desired area. The area may be regular (e.g., circular) or irregular. A bolus 962 is mounted proximate to the aperture, as shown in FIG. 33. Bolus 962 has a three-dimensional (3D) surface shape 964 that corresponds to a 3D surface shape of the distal surface 965 of a tumor being treated. The bolus is made of beam energy-absorbing material, such as plastic, and ideally restricts the maximum penetration of the particle beam within the patent to the distal surface of the tumor. Typically, the shape of the bolus is determined based on information provided about a tumor from a prescription. The control system outputs a file identifying the bolus' shape to a milling machine that produces the bolus.

In the example implementations described herein, a prescription specifies the following: particle dose, particle dose rate, patient position, patient couch rotational angle, gantry rotational angle, beam field size, beam depth, an extent of the beam depth, a configuration of an aperture used to limit the area of the particle beam, and a configuration of a bolus. In other implementations, a prescription need not include all of these characteristics and may include other or different operational characteristics of a treatment or diagnostic system.

The prescription may be transmitted in DICOM RT ION format. A control system, which may be part of the particle therapy system described herein, receives a file containing the prescription, interprets the contents of the file, and configures the particle therapy system in accordance with the prescription. The control system may include one or more processing devices and/or other electronics, programmable logic, etc. that is configured to provide input/output (I/O) to various subsystems of the particle therapy system to perform configuration processes. The following explains example configuration processes for the various operational characteristics specified in the foregoing example prescription.

The prescription may specify the dose of particles to be provided to the patient. The dose may be may controlled using ionization chamber 958 described above. That is, the particle beam is initially turned-on. A control mechanism (e.g., circuitry or a computing device) keeps track of the dose based on clicks from the counter that is triggered by output from the ionization chamber. When the dose exceeds the prescribed amount, the particle beam is turned-off (e.g., by turning-off the RF source, turning-off the ion source, or turning-off both). The particle beam may be turned-on or turned-off to increase or decrease the dose, respectively.

In some cases, the dose may be dependent on the beam field size (cross-sectional area). In an implementation, there may be three different scatterers to produce three different beam field sizes. In other implementations, this may not be the case or there may be a different number of scatterers. Each scatterer may be associated with a different coefficient A, B, C, which is multiplied by the number of clicks registered by a particle beam produced with a corresponding scatterer. For example, the coefficient for A may be 10,000, the coefficient for B may be 40,000, and the coefficient for C may be 7500. When the number of clicks times the appropriate coefficient reaches an appropriate threshold, the beam is turned-off. Values for scatterer coefficients other than those noted above may be used.

The prescription may specify the dose rate for particles to be provided to the patient. The dose rate, in this context, corresponds to the dose provided across a range of depths within the patient (e.g., to the shape of a spread-out Bragg peak). In this regard, the particle therapy system sets a nominal ion source pulse width for a nominal dose rate having a given beam field size. As described above with respect to FIG. 30, the shape of the Bragg curves may vary for different depths within the patient. Accordingly, a LUT may be used to determine how to vary the ion source pulse widths as the modulator wheel rotates in order to approximate a dose level having a uniform Bragg peak for different depths. The system also monitors the dose rate using the output of the ionization chamber and adjusts the ion source pulse width to maintain or vary a dose rate level. For example, if it is determined that a dosage is too low, all pulse widths may be increased by a certain amount in order to increase the dose level. This is in addition to varying pulse widths with wheel modulator rotation to change the shape of a spread-out Bragg peak.

In some implementations, structure 815 (FIGS. 24 and 25) scatters the particle beam. This scattering can affect the dose rate. As explained above, the rotation of structure 815 is dependent upon the rotation of the gantry. Accordingly, to compensate for the scatter introduced by structure 815, a multiplier may be selected, which is based on the rotational angle of the gantry. The multiplier may be applied to the ion source pulse width to increase or decrease the pulse width and thereby increase or decrease the intensity of the particle beam. In an example implementation, the multiplier may be a value of "2" and that multiplier may be applied to the ion source pulse width (to thereby double the pulse width) when the gantry is at an angle of 90°. In other implementations, a different multiplier (including a fractional multiplier) may be used, no multiplier may be used, or numerous different multipliers may be used for different gantry rotational angles.

The prescription may specify the patient position, as defined by the location of the couch on which the patient lies. In some implementations, the couch position is specified in terms of Cartesian X, Y and Z coordinates. The control system may receive these coordinates, and control one or more motors or other movement mechanisms to put the couch in the appropriate XYZ position. The prescription may also specify the rotational position ($\phi$) of the couch. In this regard, the couch is rotatable relative to a predefined plane (e.g., the XY plane). $\phi$ indicates the amount of the rotation for the couch relative to that plane.

The prescription may specify the rotational position of the gantry. This is specified in the prescription via an angle $\theta$. In this regard, the gantry (on which the particle accelerator is mounted) may be rotated around an axis to a point at which treatment is to be applied, as described above. The control system identifies this rotational position ($\theta$) in the prescription, and moves the gantry accordingly.

The prescription may specify the beam field size (e.g., the cross-sectional area of the particle beam to be applied to the patient). In some implementations, the cross-sectional area of the particle beam is circular. In other implementations, the cross-sectional area of the particle beam may have other shapes, e.g., oval, rectangular, and so forth. In any case, the beam field size may be specified in terms of XY coordinates. The control system receives these XY coordinates and controls the beam field size by selecting an appropriate scatterer (e.g., 956) to place in the beam's path. As described above, different scatterers produce different beam field sizes. In this regard, various scatterers may be positioned on a tray that is movable relative to a beam path so as to position a particular scatterer in the beam path. In an implementation, the tray includes three separate scatterers and a hole (which can be filled with another device). In other implementations, there may be more or less selectable scatterers.

In some implementations, the particle beam may hit the scatterer off-center depending upon the gantry angle. This may be caused by scattering produced by structure 815. Accordingly, the position of the scatterer may be controlled, e.g., in accordance with the prescription, so that the particle beam hits the center of, close to the center of, or any other appropriate location on the scatterer. Moving the scatterer in this manner can reduce unexpected disparities in beam field size.

The prescription may specify a depth to which the particle beam is to penetrate the patient. The depth may be controlled, at least in part, by incorporating one or more beam absorbers into the beam path (e.g., as part of the scatterer). For example, as described above, an absorber 957 may be plastic, and may have a thickness that is linearly related to the amount by which the penetration depth is to be decreased. For example, if the penetration depth is to be decreased by 10 cm, then the absorber may have a uniform 10 cm thickness. As noted above, the absorber may be a wheel having different thicknesses. The appropriate thickness can be dialed into the particle beam path based on the depth specified in the prescription. A motor or other mechanism may control the wheel. In other implementations, a different structure and movement mechanism may be used.

The specified depth may also require selection of an appropriate modulator wheel. More specifically, as explained above, each modulator wheel is configured to provide a range of Bragg peak depths. As described above, linear interpolation may be used to determine the variations in pulse widths that may be used to correct spread-out Bragg peaks at different depths. In other implementations, pulse widths may be adjusted as follows. As noted above, FIG. 31 shows pulse width plotted against rotation angles relative to the different Bragg peaks a, b and c. As shown in FIG. 31, at point a, the pulse width is greatest (and increased), since additional particle beam intensity is needed to bring point a to the nominal level. At point c the pulse width is least (and decreased) since decreased particle beam intensity is needed to bring point c to the nominal level.

In some implementations, the pulse width and corresponding rotation angle of the modulator wheel is determined for Bragg peaks half-way (at e) between a deepest depth at a and a design depth at b, and half-way (at d) between a shallowest depth c and a design depth b. Relationships between pulse width and rotation angle are determined for those half-way points. And, an appropriate pulse-width adjustment curve b, d or e (FIG. 31) is selected based on the location of a Bragg peak relative to a, b or c. For example, if the Bragg peak is between c and d, curve c is selected; if the Bragg peak is between b and d, curve b is selected; if the Bragg peak is between e and a, curve a is selected; and if the Bragg peak is between b and e, curve b is selected. The curves used to specify the pulse width for different rotation angles may be part of a beam current modulation (BCM) file. In an implementation, there are two BCM files per modulator wheel and 12 modulator wheels; however, different implementations may include different numbers of BCM files and modulator wheels.

Accordingly, to summarize, LUTs that specify a depth to which the particle beam is to penetrate the patient may provide information indicating which modulator wheel to select, which absorber to use, and which BCM file to use.

The prescription may specify the extent of the depth into the patient (e.g., the length of the spread-out Bragg peak within the patient). More specifically, as indicated above, each modulator wheel may be designed to provide uniform spread-out Bragg peaks from a maximum depth to the surface of a patient (e.g., to the outer layer of the patient's skin). To customize the depth of dosage, Bragg peaks in undesired locations (e.g., in area 917 in FIG. 26) may be "turned-off". This may be done by turning-off the RF source, turning-off the ion source, or turning-off both at an appropriate time during each rotation of the modulator wheel. As a result, it is possible to customize the length of the Bragg peak based on the prescription.

The prescription may specify a particular shape of the particle beam. The shape may be controlled by selecting an appropriate aperture, through which the particle beam is to pass. The aperture may be selected and mounted automatically (e.g., using motors, robots, or the like) or manually.

The prescription may specify a distal shape of a tumor to be treated with particle therapy. The shape may be irregular, and may inherently specify a variable depth of the particle beam. As described above, a bolus may be manufactured and installed, either manually or automatically, to provide maximum particle beam depths that correspond to the distal shape of the tumor.

As described above, the movement (e.g., rotation) of the structure may be computer-controlled using a control system that is part of the broader particle therapy system. Computer control may include generating one or more control signals to control movement of mechanical devices, such as actuators and motors that produce the motion. The rotation of structure 815 may be controlled based on a rotational position of the particle accelerator, as measured by the rotational position of the gantry (see, e.g., FIGS. 1, 11 and 12 showing gantry rotation) on which the particle accelerator is mounted. The various parameters used to set the rotational position of the structure vis-à-vis the position of the gantry may be measured empirically, and programmed into the control system computer.

In this regard, the effects of gravity can affect the consistency of the particle beam across different angles. For example, the gantry rotates the particle accelerator around the patient. As a result, the accelerator must deliver the particle beam from different angles. The different effects of gravity at these angles can cause the particle beam to have different properties at the different angles. In the example systems described herein, the control system computer may be programmed to account for the effects of gravity, and to make adjustments to the system to counteract these effects. For example, in an implementation, a set of parameters may be set (e.g., in a look-up table that is part of, or not part of, the prescription) that are specified for each rotational angle of the gantry. The control system computer may determine a current angle of the gantry, read parameters from the table corresponding to that angle, and make appropriate adjustments based on those parameters.

In an example implementation, the look-up table includes parameters for angular increments of ten degrees, e.g., for gantry angles of 10°, 20°, 30°, 40°, and so forth. For gantry angles in between these ten-degree increments, the control computer system may interpolate between parameters values for angles above and below the in-between gantry angle. In some implementations, the angular increments may be less than ten degrees, e.g., the angular increments may be one degree, two degrees, five degrees, and so forth.

In some implementations, the parameters that are gantry dependent, and that may be included in one or more look-up tables (or other constructs) to vary with gantry angle include, but are not limited to: the rotation of structure 815 (a "microaborber wheel"), a magnet current offset appropriate for a given angle, an ion (beam) current offset appropriate for a given angle, a particle pulse-width for a given angle (e.g., the width/duration of a pulse of particles from the ion source), a frequency amplitude modulation table for a given angle, position values for a steering coil at the output of the accelerator to direct the particle beam to the patient, and coil positions, including main coils and any active return coils.

In some implementations, the control system computer uses an open-loop correction process and, in other implementations, the control system computer uses a closed-loop correction process. In an example open-loop correction process, the control system computer obtains a parameter from the look-up table for a particular angle, and performs operations to set the system at the obtained parameter. For example, the system may obtain a magnet current for a given gantry angle, and output a signal to send the appropriate amount of current to the magnet. In an example closed-loop correction process, the control system computer obtains a parameter for the look-up table, determines a current value corresponding to the parameter, and makes appropriate adjustments until the current value reaches the obtained value. For example, a feedback system and/or feedback circuitry may be used to measure the current value and adjustments to that value, and the control system computer may continue making adjustments until the appropriate value for the parameter is achieved.

Figure 34:
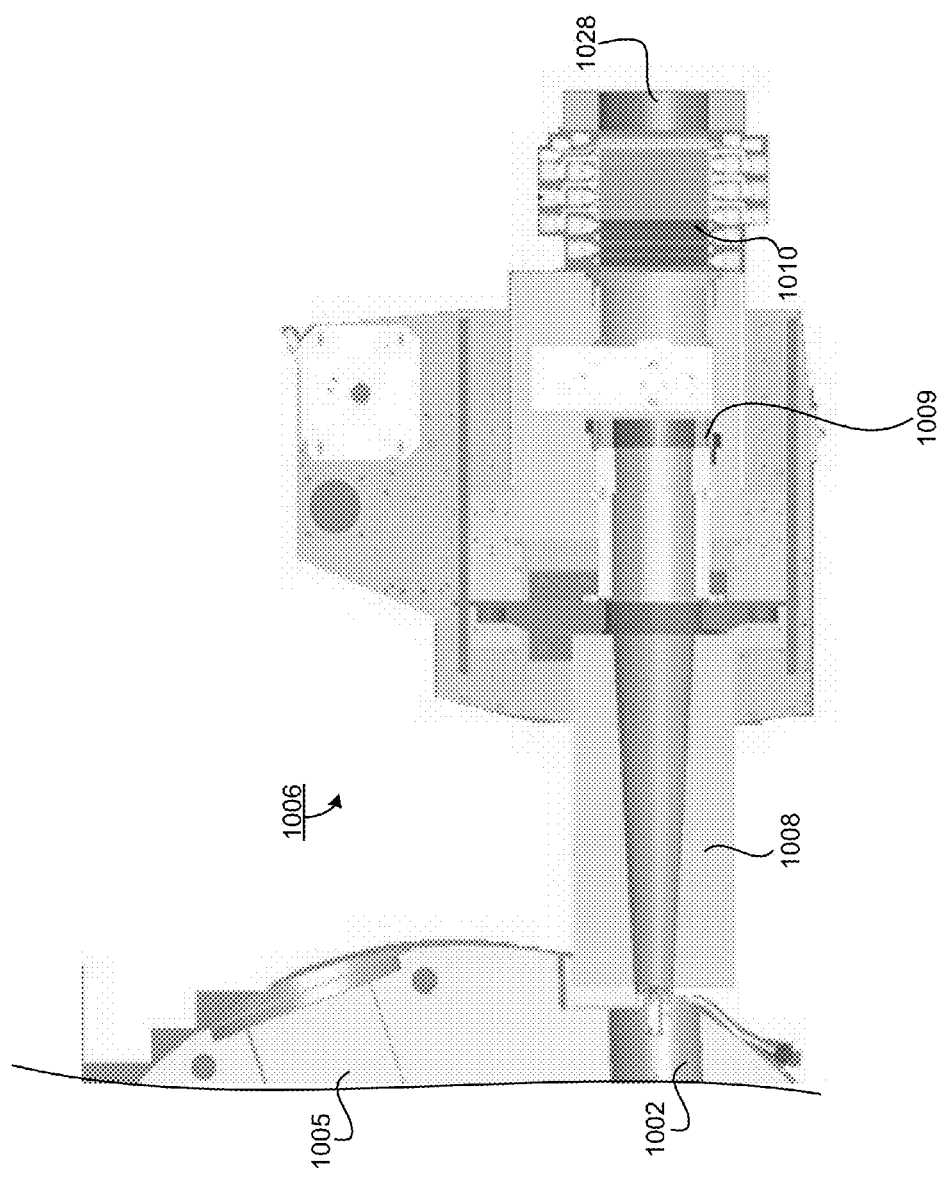
FIG. 34 is a side view of an example scanning system.
Figure 35:
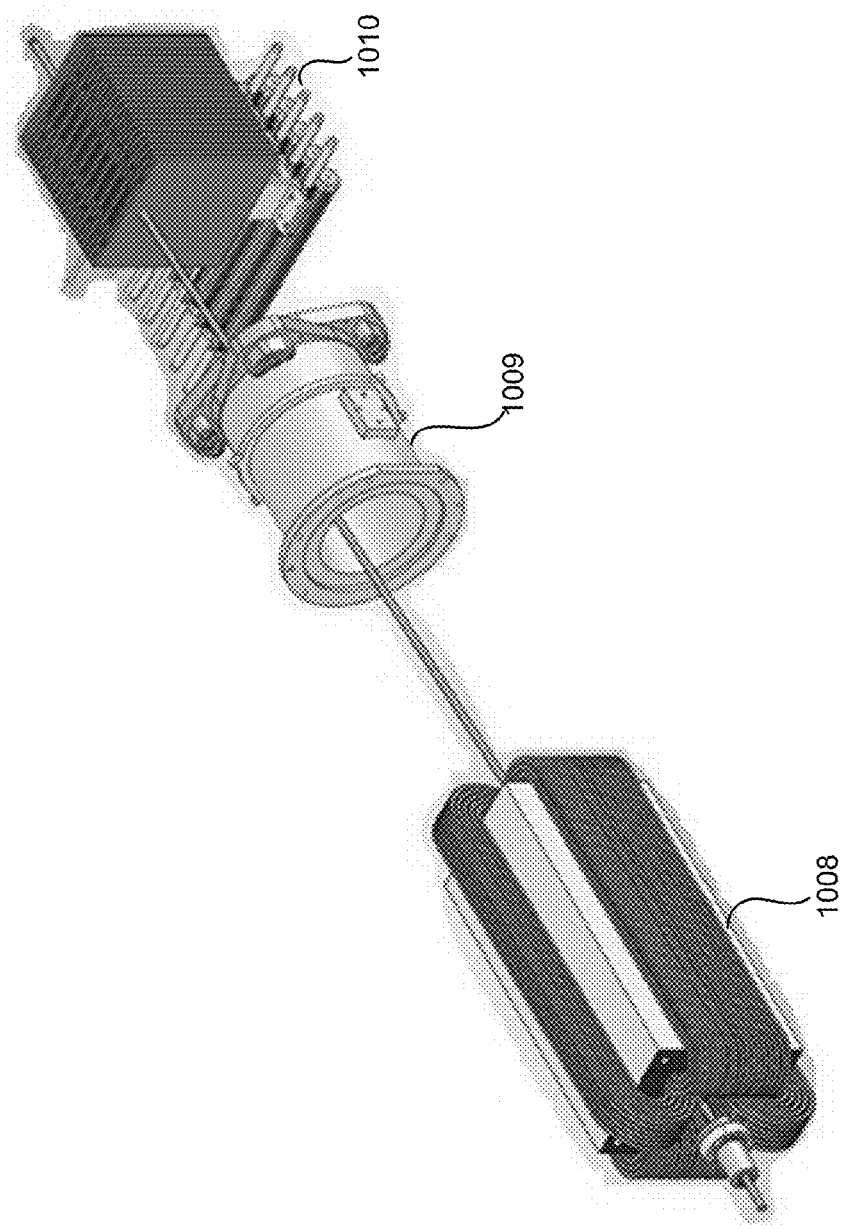
FIG. 35 is a perspective view of the example scanning system.

In some implementations, the particle therapy system includes a scanning system at the output of the particle accelerator. In this regard, referring to FIG. 34, at the output of extraction channel 1002 of a particle accelerator (which may have the configuration shown in FIGS. 1 and 2) is a beam formation system, such as beam formation system 125. The beam formation system may be a scanning system. An example scanning system 1006 is shown in FIG. 34, which may be used to scan the particle beam across at least part of an irradiation target. FIG. 35 shows examples of the components of the scanning system include a scanning magnet 1008, an ion chamber 1009, and an energy degrader 1010. Other components of the scanning system are not shown in FIG. 35.

In an example operation, scanning magnet 1008 is controllable in two dimensions (e.g., Cartesian XY dimensions) to direct the particle beam across a part (e.g., a cross-section) of an irradiation target. Ion chamber 1009 detects the dosage of the beam and feeds-back that information to a control system. Energy degrader 1010 is controllable to move material into, and out of, the path of the particle beam to change the energy of the particle beam and therefore the depth to which the particle beam will penetrate the irradiation target.

FIGS. 36 and 37 shows views of an example scanning magnet 1008. Scanning magnet 1008 includes two coils 1011, which control particle beam movement in the X direction, and two coils 1012, which control particle beam movement in the Y direction. Control is achieved, in some implementations, by varying current through one or both sets of coils to thereby vary the magnetic field(s) produced thereby. By varying the magnetic field(s) appropriately, the particle beam can be moved in the X and/or Y direction across the irradiation target. In some implementations, the scanning magnet is not movable physically relative to the particle accelerator. In other implementations, the scanning magnet may be movable relative to the accelerator (e.g., in addition to the movement provided by the gantry).

In this example, ion chamber 1009 detects dosage applied by the particle beam by detecting the numbers of ion pairs created within a gas caused by incident radiation. The numbers of ion pairs correspond to the dosage provided by the particle beam. That information is fed-back to a computer system that controls operation of the particle therapy system. The computer system (not shown), which may include memory and one or more processing devices, determines if the dosage detected by ion chamber is the intended dose. If the dosage is not as intended, the computer system may control the accelerator to interrupt production and/or output of the particle beam, and/or control the scanning magnet to prevent output of the particle beam to the irradiation target.

Figure 38:
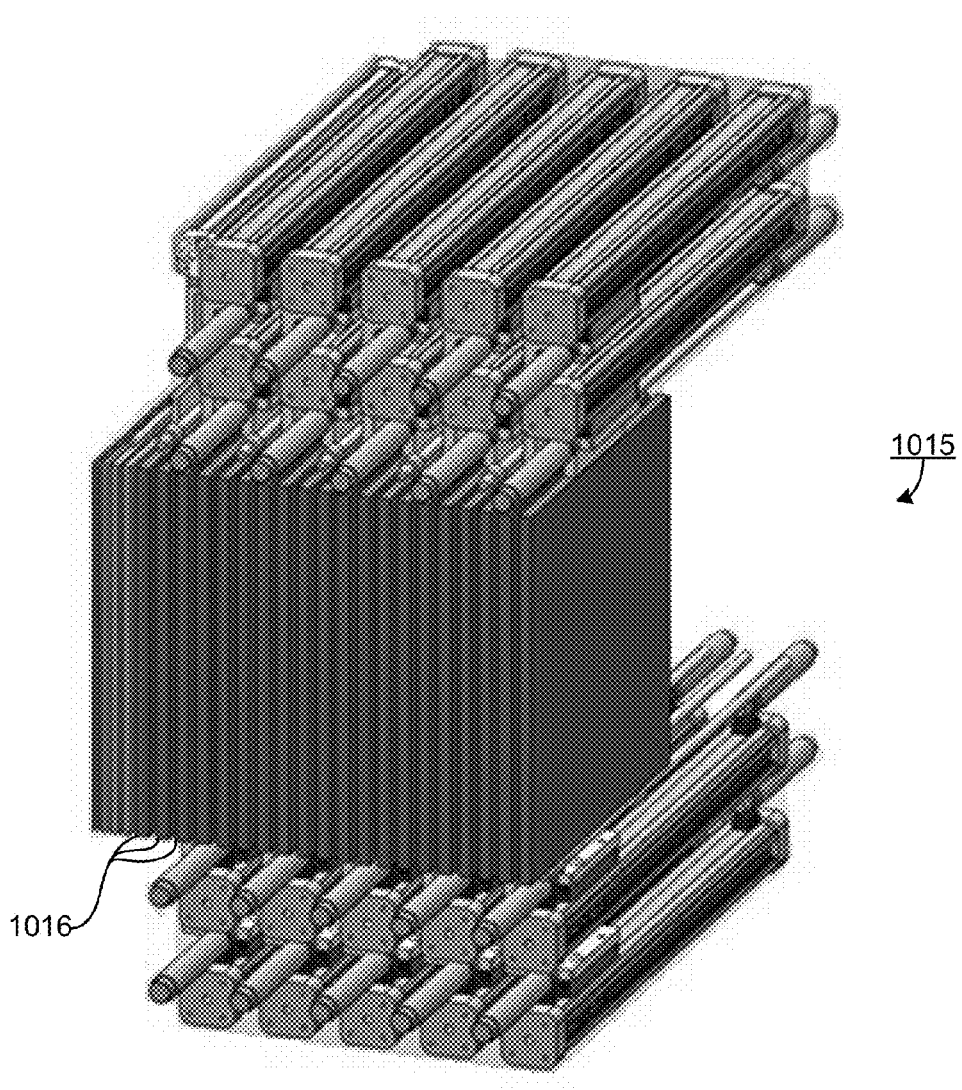
FIG. 38 is a perspective view of an example range modulator that may be used in the example scanning system.

FIG. 38 shows a range modulator 1015, which is an example implementation of energy degrader 1010. In some implementations, such as that shown in FIG. 38, range modulator includes a series of plates 1016. The plates may be made of one or more energy absorbing materials.

One or more of the plates is movable into, or out of, the beam path to thereby affect the energy of the particle beam and, thus, the depth of penetration of the particle beam within the irradiation target. For example, the more plates that are moved into the path of the particle beam, the more energy that will be absorbed by the plates, and the less energy the particle beam will have. Conversely, the fewer plates that are moved into the path of the particle beam, the less energy that will be absorbed by the plates, and the more energy the particle beam will have. Higher energy particle beams penetrate deeper into the irradiation target than do lower energy particle beams. In this context, "higher" and "lower" are meant as relative terms, and do not have any specific numeric connotations.

Figure 39:
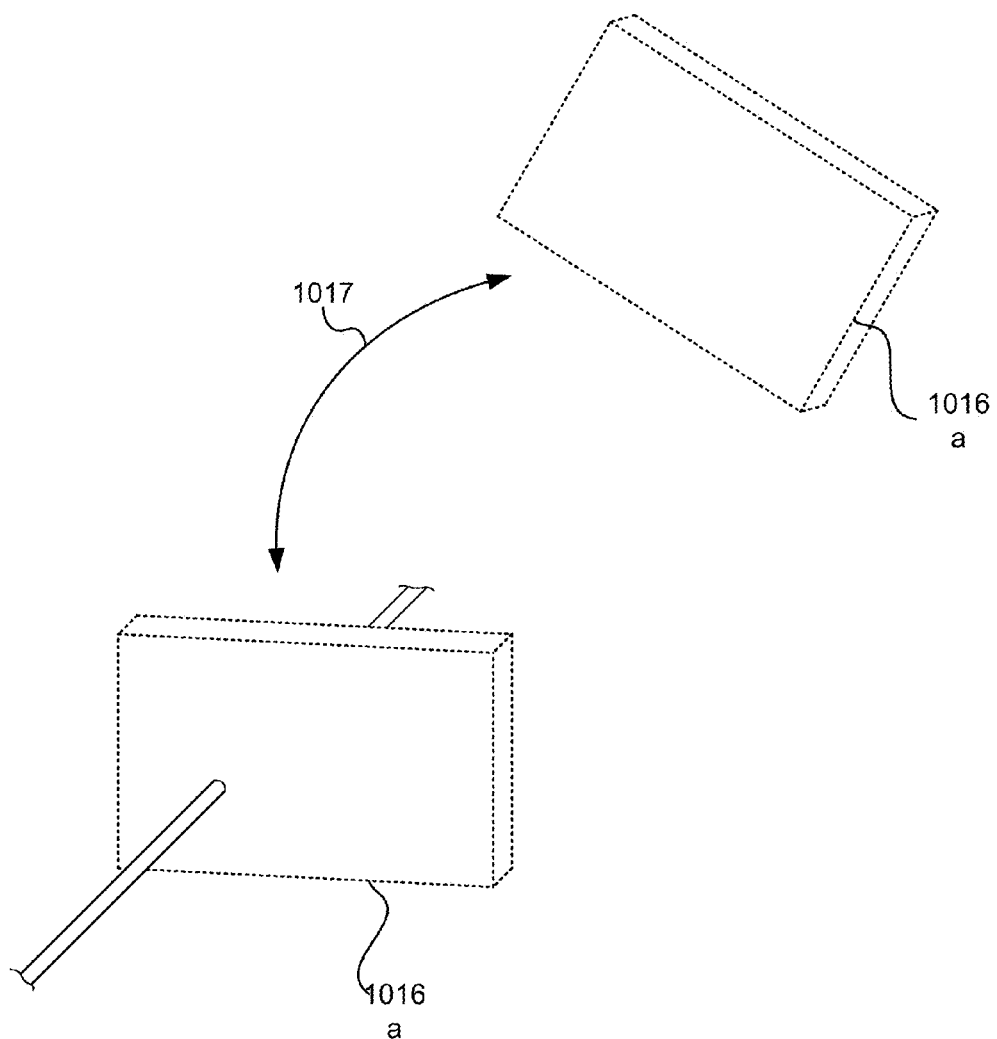
FIG. 39 is a perspective view of motion of a plate from the range modulator into/out of the beam path.

Plates are moved physically into, and out of, the path of the particle beam. For example, as shown in FIG. 39, a plate 1016a moves along the direction of arrow 1017 between positions in the path of the particle beam and outside the path of the particle beam. The plates are computer-controlled. Generally, the number of plates that are moved into the path of the particle beam corresponds to the depth at which scanning of an irradiation target is to take place. For example, the irradiation target can be divided into cross-sections, each of which corresponds to an irradiation depth. One or more plates of the range modulator can be moved into, or out of, the beam path to the irradiation target in order to achieve the appropriate energy to irradiate each of these cross-sections of the irradiation target.

In some implementations, a treatment plan is established prior to treating the irradiation target using scanning. The treatment plan may specify how scanning is to be performed for a particular irradiation target. In some implementations, the treatment plan specifies the following information: a type of scanning (e.g., spot scanning or raster scanning); scan locations (e.g., locations of spots to be scanned); magnet current per scan location; dosage-per-spot; locations (e.g., depths) of irradiation target cross-sections; particle beam energy per cross-section; plates or other types of pieces to move into the beam path for each particle beam energy; and so forth. Generally, spot scanning involves applying irradiation at discrete spots on an irradiation target and raster scanning involves moving a radiation spot across the radiation target. The concept of spot size therefore applies for both raster and spot scanning.

Any components of the scanning system, including those described above, may be affected by gravity resulting from movement of the accelerator. Accordingly, any or all of the foregoing components of the scanning system may be controlled to compensate for the effects of gravity. In this regard, the range modulator does not typically rotate with the accelerator; however, in systems where it does, the range modulator may be controlled as well. Both open-loop and closed-loop control may be used to compensate for the effects of gravity on the scanning system. Parameters associated with the scanning system may be incorporated into the look-up table and obtained by the control computer as described above.

Configuration of the particle therapy system in accordance with a prescription may be computer-controlled. Computer controls may be effected through one or more signals output from one or more computers to various electronics on, or associated with, the particle therapy system. In this regard, all or part of the configuration processes implemented by the control system and their various modifications (hereinafter referred to as "the processes") can be implemented, at least in part, via a computer program product, i.e., a computer program tangibly embodied in one or more information carriers, e.g., in one or more tangible, non-transitory machine-readable storage media, for execution by, or to control the operation of, data processing apparatus, e.g., a programmable processor, a computer, or multiple computers A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a network.

Actions associated with implementing the processes can be performed by one or more programmable processors executing one or more computer programs to perform the functions of the calibration process. All or part of the processes can be implemented as, special purpose logic circuitry, e.g., an FPGA (field programmable gate array) and/or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only storage area or a random access storage area or both. Elements of a computer (including a server) include one or more processors for executing instructions and one or more storage area devices for storing instructions and data. Generally, a computer will also include, or be operatively coupled to receive data from, or transfer data to, or both, one or more machine-readable storage media, such as mass storage devices for storing data, e.g., magnetic, magneto-optical disks, or optical disks. Machine-readable storage media suitable for embodying computer program instructions and data include all forms of non-volatile storage area, including by way of example, semiconductor storage area devices, e.g., EPROM, EEPROM, and flash storage area devices; magnetic disks, e.g., internal hard disks or removable disks; magneto-optical disks; and CD-ROM and DVD-ROM disks.

Any two more of the foregoing implementations may be used in an appropriate combination to affect the energy of a particle beam in the extraction channel. Likewise, individual features of any two more of the foregoing implementations may be used in an appropriate combination for the same purpose.

Elements of different implementations described herein may be combined to form other implementations not specifically set forth above. Elements may be left out of the processes, systems, apparatus, etc., described herein without adversely affecting their operation. Various separate elements may be combined into one or more individual elements to perform the functions described herein.

The example implementations described herein are not limited to use with a particle therapy system or to use with the example particle therapy systems described herein.

Additional information concerning the design of an example implementation of a particle accelerator that may be used in a system as described herein can be found in U.S. Provisional Application No. 60/760,788, entitled "High-Field Superconducting Synchrocyclotron" and filed Jan. 20, 2006; U.S. patent application Ser. No. 11/463,402, entitled "Magnet Structure For Particle Acceleration" and filed Aug. 9, 2006; and U.S. Provisional Application No. 60/850,565, entitled "Cryogenic Vacuum Break Pneumatic Thermal Coupler" and filed Oct. 10, 2006, all of which are incorporated herein by reference.

The following applications are incorporated by reference into the subject application: the U.S. Provisional application entitled "CONTROLLING INTENSITY OF A PARTICLE BEAM" (Application No. 61/707,466), the U.S. Provisional application entitled "ADJUSTING ENERGY OF A PARTICLE BEAM" (Application No. 61/707,515), the U.S. Provisional application entitled "ADJUSTING COIL POSITION" (Application No. 61/707,548), the U.S. Provisional application entitled "FOCUSING A PARTICLE BEAM USING MAGNETIC FIELD FLUTTER" (Application No. 61/707,572), the U.S. Provisional application entitled "MAGNETIC FIELD REGENERATOR" (Application No. 61/707,590), the U.S. Provisional application entitled "FOCUSING A PARTICLE BEAM" (Application No. 61/707,704), the U.S. Provisional application entitled "CONTROLLING PARTICLE THERAPY (Application No. 61/707,624), and the U.S. Provisional application entitled "CONTROL SYSTEM FOR A PARTICLE ACCELERATOR" (Application No. 61/707,645).

The following are also incorporated by reference into the subject application: U.S. Pat. No. 7,728,311 which issued on Jun. 1, 2010, U.S. patent application Ser. No. 11/948,359 which was filed on Nov. 30, 2007, U.S. patent application Ser. No. 12/275,103 which was filed on Nov. 20, 2008, U.S. patent application Ser. No. 11/948,662 which was filed on Nov. 30, 2007, U.S. Provisional Application No. 60/991,454 which was filed on Nov. 30, 2007, U.S. Pat. No. 8,003,964 which issued on Aug. 23, 2011, U.S. Pat. No. 7,208,748 which issued on Apr. 24, 2007, U.S. Pat. No. 7,402,963 which issued on Jul. 22, 2008, U.S. patent application Ser. No. 13/148,000 filed Feb. 9, 2010, U.S. patent application Ser. No. 11/937,573 filed on Nov. 9, 2007, U.S. patent application Ser. No. 11/187,633, titled "A Programmable Radio Frequency Waveform Generator for a Synchrocyclotron," filed Jul. 21, 2005, U.S. Provisional Application No. 60/590,089, filed on Jul. 21, 2004, U.S. patent application Ser. No. 10/949,734, titled "A Programmable Particle Scatterer for Radiation Therapy Beam Formation", filed Sep. 24, 2004, and U.S. Provisional Application No. 60/590,088, filed Jul. 21, 2005.

Any features of the subject application may be combined with one or more appropriate features of the following: the U.S. Provisional application entitled "CONTROLLING INTENSITY OF A PARTICLE BEAM" (Application No. 61/707,466), the U.S. Provisional application entitled "ADJUSTING ENERGY OF A PARTICLE BEAM" (Application No. 61/707,515), the U.S. Provisional application entitled "ADJUSTING COIL POSITION" (Application No. 61/707,548), the U.S. Provisional application entitled "FOCUSING A PARTICLE BEAM USING MAGNETIC FIELD FLUTTER" (Application No. 61/707,572), the U.S. Provisional application entitled "MAGNETIC FIELD REGENERATOR" (Application No. 61/707,590), the U.S. Provisional application entitled "FOCUSING A PARTICLE BEAM" (Application No. 61/707,704), the U.S. Provisional application entitled "CONTROLLING PARTICLE THERAPY (Application No. 61/707,624), and the U.S. Provisional application entitled "CONTROL SYSTEM FOR A PARTICLE ACCELERATOR" (Application No. 61/707,645), U.S. Pat. No. 7,728,311 which issued on Jun. 1, 2010, U.S. patent application Ser. No. 11/948,359 which was filed on Nov. 30, 2007, U.S. patent application Ser. No. 12/275,103 which was filed on Nov. 20, 2008, U.S. patent application Ser. No. 11/948,662 which was filed on Nov. 30, 2007, U.S. Provisional Application No. 60/991,454 which was filed on Nov. 30, 2007, U.S. patent application Ser. No. 13/907,601, which was filed on May 31, 2013, U.S. patent application Ser. No. 13/916,401, filed on Jun. 12, 2013, U.S. Pat. No. 8,003,964 which issued on Aug. 23, 2011, U.S. Pat. No. 7,208,748 which issued on Apr. 24, 2007, U.S. Pat. No. 7,402,963 which issued on Jul. 22, 2008, U.S. patent application Ser. No. 13/148,000 filed Feb. 9, 2010, U.S. patent application Ser. No. 11/937,573 filed on Nov. 9, 2007, U.S. patent application Ser. No. 11/187,633, titled "A Programmable Radio Frequency Waveform Generator for a Synchrocyclotron," filed Jul. 21, 2005, U.S. Provisional Application No. 60/590,089, filed on Jul. 21, 2004, U.S. patent application Ser. No. 10/949,734, titled "A Programmable Particle Scatterer for Radiation Therapy Beam Formation", filed Sep. 24, 2004, and U.S. Provisional Application No. 60/590,088, filed Jul. 21, 2005.

Except for the provisional application from which this patent application claims priority and the documents incorporated by reference above, no other documents are incorporated by reference into this patent application.

Other implementations not specifically described herein are also within the scope of the following claims.

What is claimed is:

1. A particle therapy system comprising:
a gantry that is rotatable relative to a patient position;
a particle accelerator mounted to the gantry, the particle accelerator for outputting a particle beam to the patient position; and
a control system to generate machine instructions for configuring operational characteristics of the particle therapy system, at least one of the operational characteristics relating to, or being affected by, a rotational angle of the gantry relative to the patient position;
wherein configuring the operational characteristics of the particle therapy system comprises adjusting a position of a microabsorber wheel, adjusting a magnetic current of a superconducting magnet in the particle accelerator, and changing a pulse width of particle pulses output from the accelerator.

2. The particle therapy system of claim 1, wherein the at least one of the operational characteristics comprises the rotational angle of the gantry.

3. The particle therapy system of claim 1, further comprising a particle source to provide the particle pulses to a cavity, the particle pulses comprising pulses of ionized plasma, a particle pulse of the particle source having a pulse width corresponding to a duration of operation of the particle source to produce the particle pulse; and wherein changing a pulse width of particle pulses comprises applying a multiplier to the pulse width that is based on the rotational angle of the gantry.

4. The particle therapy system of claim 1, wherein at least one of the operational characteristics comprises a dosage of particles output by the particle accelerator.

5. The particle therapy system of claim 1, wherein at least one of the operational characteristics comprises a dose rate of particles output by the particle accelerator.

6. The particle therapy system of claim 5, further comprising:

a particle source to provide the particle pulses to a cavity, the particle pulses comprising pulses of ionized plasma, each particle pulse having a pulse width corresponding to a duration of operation of the particle source to produce the corresponding particle pulse; and a modulator wheel having different thicknesses, each thickness extending across a different circumferential length of the modulator wheel;

wherein configuring the dose rate comprises varying pulse widths based on rotational position of the modulator wheel.

7. The particle therapy system of claim 1, wherein at least one of the operational characteristics comprises a position of a patient.

8. The particle therapy system of claim 7, further comprising:

a structure on which the patient lies, the structure corresponding to the patient position;

wherein configuring the position of the patient comprises moving the structure relative to one or more coordinate positions.

9. The particle therapy system of claim 1, wherein at least one of the operational characteristics comprises field size of a particle beam output by the particle accelerator.

10. The particle therapy system of claim 9, further comprising:

scattering devices having different configurations for changing the field size of the particle beam;

wherein configuring the field size comprises selecting one of the scattering devices to move into a path of the particle beam, and moving the selected scattering device into the path of the particle beam.

11. The particle therapy system of claim 1, wherein at least one of the operational characteristics comprises depth of a particle beam output by the particle accelerator.

12. The particle therapy system of claim 11, further comprising:

an absorber having different thicknesses for absorbing particle beam;

wherein configuring the depth comprises controlling the absorber so as to place a specific thickness in a path of the particle beam.

13. The particle therapy system of claim 11, further comprising:

modulator wheels, each modulator wheel having different thicknesses, each thickness of a modulator wheel extending across a different circumferential length of the modulator wheel;

wherein configuring the depth comprises selecting a modulator wheel to move into a path of the particle beam.

14. The particle therapy system of claim 13, further comprising:

a particle source to provide the particle pulses to a cavity, the particle pulses comprising pulses of ionized plasma, each particle pulse having a pulse width corresponding to a duration of operation of the particle source to produce the corresponding pulse;

wherein configuring the depth further comprises selecting a file containing instructions for varying the pulse width based on a rotational position of a selected modulator wheel.

15. The particle therapy system of claim 1, wherein at least one of the operational characteristics comprises an extent of a depth of a particle beam output by the particle accelerator.

16. The particle therapy system of claim 15, further comprising:

a particle source to provide the particle pulses to a cavity, the particle pulses comprising pulses of ionized plasma, each particle pulse having a pulse width corresponding to a duration of operation of the particle source to produce the corresponding pulse; and a modulator wheel having different thicknesses, each thickness extending across a different circumferential length of the modulator wheel;

wherein configuring the extent of the depth of a particle beam comprises turning-off the particle source at specific rotational positions of the modulator wheel.

17. The particle therapy system of claim 1, wherein at least one of the operational characteristics comprises a shape of a particle beam output by the particle accelerator.

18. The particle therapy system of claim 17, further comprising one or more apertures corresponding to different shapes;

wherein configuring the shape of particle beam comprises selecting one of the apertures and moving the aperture selected into a path of the particle beam.

19. The particle therapy system of claim 1, wherein at least one of the operational characteristics comprises a depth-wise shape of a particle beam output by the particle accelerator.

20. The particle therapy system of claim 19, further comprising a range compensating bolus;

wherein configuring the depth-wise shape of particle beam comprises moving the range compensating bolus into a path of the particle beam.

21. The particle therapy system of claim 1, wherein the control system comprises one or more computing devices programmed to control elements of the particle therapy system that control the operational characteristics based on the machine instructions.

22. The particle therapy system of claim 1, wherein the particle therapy system comprises a scanning system, and wherein one or more of the operational characteristics relate to the scanning system.

23. The particle therapy system of claim 1, wherein configuring one or more operational characteristics of the particle therapy system is performed using open-loop control.

24. The particle therapy system of claim 1, wherein configuring one or more operational characteristics of the particle therapy system is performed using closed-loop control.

* * * * *